US012097259B2

(12) United States Patent
Xu

(10) Patent No.: US 12,097,259 B2
(45) Date of Patent: Sep. 24, 2024

(54) DENDRITIC CELL TUMOR VACCINE AND USES THEREOF

(71) Applicant: SHENZHEN FRONTIERGATE BIOTECHNOLOGY CO., LTD, Guangdong (CN)

(72) Inventor: Yang Xu, Guangdong (CN)

(73) Assignee: SHENZHEN FRONTIERGATE BIOTECHNOLOGY CO., LTD, Guangdong (CN)

( * ) Notice: Subject to any disclaimer, the term of this patent is extended or adjusted under 35 U.S.C. 154(b) by 0 days.

(21) Appl. No.: 18/169,174

(22) Filed: Feb. 14, 2023

(65) Prior Publication Data

US 2023/0233678 A1 Jul. 27, 2023

Related U.S. Application Data

(63) Continuation of application No. PCT/CN2023/071170, filed on Jan. 9, 2023.

(30) Foreign Application Priority Data

Jan. 11, 2022 (WO) ................ PCT/CN2022/071239
Dec. 12, 2022 (WO) ................ PCT/CN2022/138288

(51) Int. Cl.
*A61K 39/00* (2006.01)
*C07K 14/47* (2006.01)
*C07K 14/705* (2006.01)
*C07K 14/725* (2006.01)

(52) U.S. Cl.
CPC ...... *A61K 39/4615* (2023.05); *A61K 39/0011* (2013.01); *A61K 39/4622* (2023.05); *A61K 39/4631* (2023.05); *A61K 39/4634* (2023.05); *A61K 39/4644* (2023.05); *C07K 14/4746* (2013.01); *C07K 14/4748* (2013.01); *C07K 14/7051* (2013.01); *C07K 14/70517* (2013.01); *A61K 2039/5154* (2013.01); *A61K 2039/5156* (2013.01); *A61K 2239/13* (2023.05); *A61K 2239/21* (2023.05); *A61K 2239/22* (2023.05); *C07K 2317/622* (2013.01); *C07K 2319/02* (2013.01); *C07K 2319/03* (2013.01)

(58) Field of Classification Search
CPC ........ A61K 2039/5156; A61K 2239/13; A61K 2239/5156; A61K 2239/22; A61K 39/4615; A61K 39/4631; A61K 39/4622; A61K 39/4634; A61K 2239/10; A61K 39/46; A61K 39/464401; A61K 39/4644; A61K 39/462; A61K 2039/5154; C07K 2319/03; C07K 2319/33; C07K 2317/622
See application file for complete search history.

(56) References Cited

U.S. PATENT DOCUMENTS

| 2017/0151281 A1 | 6/2017 | Wagner et al. |
| 2019/0100592 A1 | 4/2019 | Hamilton et al. |
| 2020/0255505 A1 | 8/2020 | Staley et al. |

FOREIGN PATENT DOCUMENTS

| CN | 107286246 | * | 10/2017 | .............. A61P 35/00 |
| CN | 107286247 A | | 10/2017 | |
| CN | 111197032 A | | 5/2020 | |
| CN | 112830974 A | | 5/2021 | |
| CN | 113122502 A | | 7/2021 | |
| WO | WO-2017109110 A1 | * | 6/2017 | .............. A61K 35/17 |
| WO | WO-2017120998 A1 | * | 7/2017 | ......... A61K 31/7088 |
| WO | WO-2017177337 A1 | * | 10/2017 | .............. A61K 35/17 |
| WO | WO-2018074978 A1 | * | 4/2018 | .............. A61K 39/00 |
| WO | WO-2018102584 A1 | * | 6/2018 | .............. A61K 35/74 |
| WO | WO-2019177986 A1 | * | 9/2019 | .............. A61K 35/17 |

OTHER PUBLICATIONS

Butterfield et al (Journal for Immuno Therapy of Cancer, 2019, vol. 7, No. 113, 15 pages) (Year: 2019).*
Abstract of Suh et al (Blood, 2018, vol. 132, suppl. 1, abstract No. 3693) (Year: 2018).*
Shuster et al ("Immunotherapy of Renal Cell Carcinoma-From Antigen Identification to Patient Treatment", In: Emerging Research and Treatments in Renal Cell Carcinoma, pp. 193-226, IntechOpen, 2012) (Year: 2012).*
Sasmita et al (Asia-Pac J Clin Oncol., 2018, vol. 14, pp. 40-51) (Year: 2018).*
Liang et al (Gene Therapy, e-Pub: May 6, 2021, vol. 30, pp. 411-420) (Year: 2021).*
Smith et al (Molecular Therapy, 2018, vol. 26, pp. 1447-1456). (Year: 2018).*
Translation of CN-10728624A spec, downloaded from the Web Jun. 11, 2023 (Year: 2023).*
Translation of WO2017120998A1 spec, downloaded from the Web Jun. 12, 2023 (Year: 2023).*
Wilment et al (Journal of Biological Chemistry, 2001, vol. 276, pp. 43818-43823) (Year: 2001).*
Mata-Martinaez et al (Frontiers in Immunology, 2022, vol. 13, Article No. 812148) (Year: 2022).*
Junker et al (Frontiers in Immunology, 2020, vol. 11, article 1393) (Year: 2020).*
Roman-Rosales et al (BMC Cancer, 2018, vol. 18, 12 pages) (Year: 2018).*
Ho et al (European Journal of Cancer, 2021, vol. 159, pp. 16-23) (Year: 2021).*

(Continued)

*Primary Examiner* — Karen A. Canella
(74) *Attorney, Agent, or Firm* — .Jun He Law Offices P.C.; Yi Zhang

(57) ABSTRACT

The present disclosure provides a dendric cell tumor vaccine comprising a chimeric antigen receptor for activating the dendritic cell and a tumor antigen. The present disclosure also provides compositions and methods of making the dendritic cell tumor vaccine, and the methods of using the dendritic cell tumor vaccine to treat cancer.

21 Claims, 16 Drawing Sheets

Specification includes a Sequence Listing.

(56) References Cited

OTHER PUBLICATIONS

Pan et al (Frontiers in Immunology, 2017, vol. 8, Article 1424 (Year: 2017).*
Fu and Jiang (Frontiers in Immunology, 2018, vol. 9, Article 3059, 11 pages) (Year: 2018).*
Nussing et al, Frontiers in Immunology, 2020, vol. 11, Article 589641, 16 pages (Year: 2020).*
"Messenger RNA-Electroporated Dendritic Cells Presenting MAGE-A3 Simultaneously in HLA Class I and Class II Molecules", Aude Bonehill et al., J Immunol J. 2004; 172(11) 6649-6657.
The First Office Action for the corresponding Chinese application 202210140959.X.
Ding L, et al. "Research progress on the development of anticancer drugs targeting mutant p53", Journal of Yangzhou University (Agricultural and Life Science Edition), vol. 41, No. 6, Nov. 30, 2020 (Nov. 30, 2020), 57-63 see p. 58, paragraphs 2 and 3.
International Search Report of PCT Application No. PCT/CN2023/071170, mailed on May 7, 2023.

* cited by examiner

H460: p53WT

gaagactccagtggtaatctactgggacggaacagctttgaggtgcgtgtttgtgcctgtcctgggagagaccggcgcacagaggaagagaat

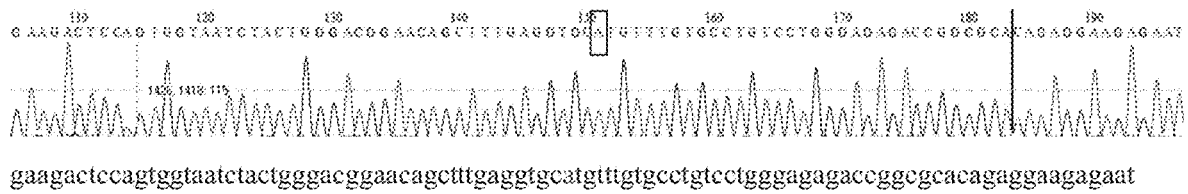

gaagactccagtggtaatctactgggacggaacagctttgaggtgcatgtttgtgcctgtcctgggagagaccggcgcacagaggaagagaat

FIG. 1D

SW837: KRAS G12C

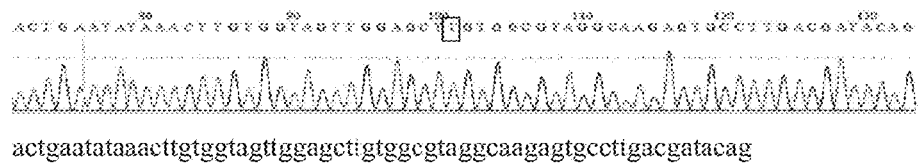

actgaatataaacttgtggtagttggagcttgtggcgtaggcaagagtgccttgacgatacag

FIG. 1E

F
SW480: KRAS G12V

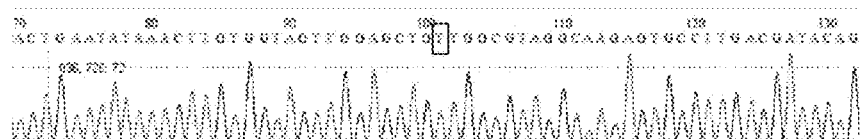

actgaatataaacttgtggtagttggagctgttggcgtaggcaagagtgccttgacgatacag

FIG. 1F

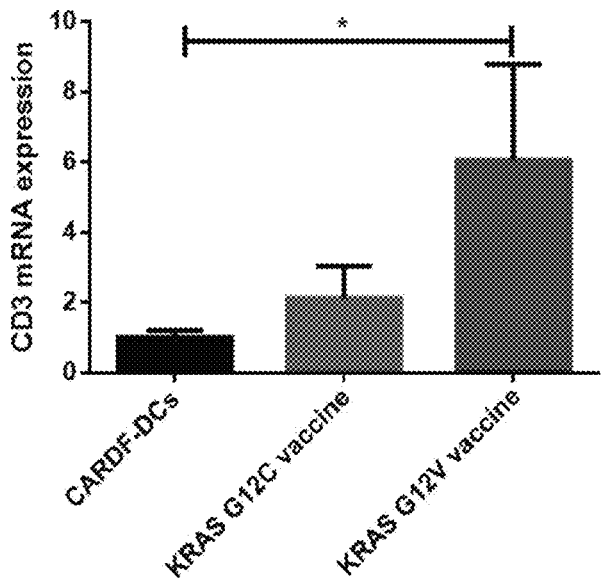
FIG. 5C
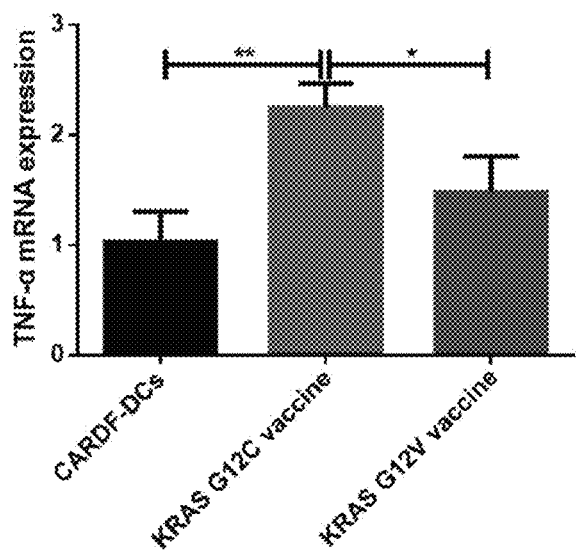
FIG. 5D
| hActin-F | CAGAGCCTCGCCTTTGCCGATC | SEQ ID NO: 19 |
| --- | --- | --- |
| hActin-R | CATCCATGGTGAGCTGGCGGCG | SEQ ID NO: 20 |
| hCD3-F | GGGGCAAGATGGTAATGAAG | SEQ ID NO: 21 |
| hCD3-R | CCAGGATACTGAGGGCATGT | SEQ ID NO: 22 |
| hTNFα-F | GCTGCACTTTGGAGTGATCG | SEQ ID NO: 23 |
| hTNFα-R | TCACTCGGGGTTCGAGAAGA | SEQ ID NO: 24 |
| CAR scfv-F | ATACCATGTCTTGGGTGCGA | SEQ ID NO: 25 |
| CAR scfv-R | AATCGGCCCTTCACACTGTC | SEQ ID NO: 26 |
FIG. 5E

SEQUENCE LISTING

Sequence total quantity: 38
SEQ ID NO: 1          moltype = AA   length = 44
FEATURE               Location/Qualifiers
REGION                1..44
                      note = Synthetic
source                1..44
                      mol_type = protein

```
                               organism = synthetic construct
SEQUENCE: 1
RWPPSAACSG KESVVAIRTN SQSDFHLQTY GDEDLNELDP HYEM                       44

SEQ ID NO: 2              moltype = AA   length = 42
FEATURE                   Location/Qualifiers
REGION                    1..42
                          note = Synthetic
source                    1..42
                          mol_type = protein
                          organism = synthetic construct
SEQUENCE: 2
RLKIQVRKAA ITSYEKSDGV YTGLSTRNQE TYETLKHEKP PQ                         42

SEQ ID NO: 3              moltype = AA   length = 86
FEATURE                   Location/Qualifiers
REGION                    1..86
                          note = Synthetic
source                    1..86
                          mol_type = protein
                          organism = synthetic construct
SEQUENCE: 3
RWPPSAACSG KESVVAIRTN SQSDFHLQTY GDEDLNELDP HYEMRLKIQV RKAAITSYEK      60
SDGVYTGLST RNQETYETLK HEKPPQ                                          86

SEQ ID NO: 4              moltype = DNA   length = 258
FEATURE                   Location/Qualifiers
misc_feature              1..258
                          note = Synthetic
source                    1..258
                          mol_type = other DNA
                          organism = synthetic construct
SEQUENCE: 4
cgctggcctc cttctgcagc ttgttcggga aaagagtcag ttgttgctat aaggaccaat      60
agccaatctg acttccactt acaaacttat ggagatgaag atttgaatga attagatcct     120
cattatgaaa tgcgactgaa gatccaagtc cgaaaggcag ctataaccag ctatgagaaa     180
tcagatggtg tttacacggg cctgagcacc aggaaccagg agacttacga gactctgaag     240
catgagaaac caccacag                                                   258

SEQ ID NO: 5              moltype = AA   length = 21
FEATURE                   Location/Qualifiers
REGION                    1..21
                          note = Synthetic
source                    1..21
                          mol_type = protein
                          organism = synthetic construct
SEQUENCE: 5
MALPVTALLL PLALLLHAAR P                                               21

SEQ ID NO: 6              moltype = AA   length = 24
FEATURE                   Location/Qualifiers
REGION                    1..24
                          note = Synthetic
source                    1..24
                          mol_type = protein
                          organism = synthetic construct
SEQUENCE: 6
IYIWAPLAGT CGVLLLSLVI TLYC                                            24

SEQ ID NO: 7              moltype = AA   length = 45
FEATURE                   Location/Qualifiers
REGION                    1..45
                          note = Synthetic
source                    1..45
                          mol_type = protein
                          organism = synthetic construct
SEQUENCE: 7
TTTPAPRPPT PAPTIASQPL SLRPEACRPA AGGAVHTRGL DFACD                     45

SEQ ID NO: 8              moltype = AA   length = 383
FEATURE                   Location/Qualifiers
REGION                    1..383
                          note = Synthetic
source                    1..383
                          mol_type = protein
                          organism = synthetic construct
SEQUENCE: 8
MGVLLTQRTL LSLVLALLFP SMASMAMHVA QPAVVLASSR GIASFVCEYA SPGKATEVRV      60
TVLRQADSQV TEVCAATYMM GNELTFLDDS ICTGTSSGNQ VNLTIQGLRA MDTGLYICKV     120
```

```
ELMYPPPYYL GIGNGTQIYV IDPEPCPDSD QEPKSSDKTH TSPPSPAPEL LGGSSVFLFP    180
PKPKDTLMIS RTPEVTCVVV DVSHEDPEVK FNWYVDGVEV HNAKTKPREE QYNSTYRVVS    240
VLTVLHQDWL NGKEYKCKVS NKALPAPIEK TISKAKGQPR EPQVYTLPPS RDELTKNQVS    300
LTCLVKGFYP SDIAVEWESN GQPENNYKTT PPVLDSDGSF FLYSKLTVDK SRWQQGNVFS    360
CSVMHEALHN HYTQKSLSLS PGK                                           383

SEQ ID NO: 9              moltype = AA   length = 290
FEATURE                   Location/Qualifiers
REGION                    1..290
                          note = Synthetic
source                    1..290
                          mol_type = protein
                          organism = synthetic construct
SEQUENCE: 9
MRIFAVFIFM TYWHLLNAFT VTVPKDLYVV EYGSNMTIEC KFPVEKQLDL AALIVYWEME     60
DKNIIQFVHG EEDLKVQHSS YRQRARLLKD QLSLGNAALQ ITDVKLQDAG VYRCMISYGG    120
ADYKRITVKV NAPYNKINQR ILVVDPVTSE HELTCQAEGY PKAEVIWTSS DHQVLSGKTT    180
TTNSKREEKL FNVTSTLRIN TTTNEIFYCT FRRLDPEENH TAELVIPELP LAHPPNERTH    240
LVILGAILLC LGVALTFIFR LRKGRMMDVK KCGIQDTNSK KQSDTHLEET               290

SEQ ID NO: 10             moltype = AA   length = 10
FEATURE                   Location/Qualifiers
REGION                    1..10
                          note = Synthetic
source                    1..10
                          mol_type = protein
                          organism = synthetic construct
SEQUENCE: 10
GFTFSSYTMS                                                           10

SEQ ID NO: 11             moltype = AA   length = 17
FEATURE                   Location/Qualifiers
REGION                    1..17
                          note = Synthetic
source                    1..17
                          mol_type = protein
                          organism = synthetic construct
SEQUENCE: 11
TISSRGTYTY YPDSVKG                                                   17

SEQ ID NO: 12             moltype = AA   length = 6
FEATURE                   Location/Qualifiers
REGION                    1..6
                          note = Synthetic
source                    1..6
                          mol_type = protein
                          organism = synthetic construct
SEQUENCE: 12
EAIFTH                                                                6

SEQ ID NO: 13             moltype = AA   length = 11
FEATURE                   Location/Qualifiers
REGION                    1..11
                          note = Synthetic
source                    1..11
                          mol_type = protein
                          organism = synthetic construct
SEQUENCE: 13
KASQDINNYH S                                                         11

SEQ ID NO: 14             moltype = AA   length = 7
FEATURE                   Location/Qualifiers
REGION                    1..7
                          note = Synthetic
source                    1..7
                          mol_type = protein
                          organism = synthetic construct
SEQUENCE: 14
RANRLVD                                                               7

SEQ ID NO: 15             moltype = AA   length = 9
FEATURE                   Location/Qualifiers
REGION                    1..9
                          note = Synthetic
source                    1..9
                          mol_type = protein
                          organism = synthetic construct
SEQUENCE: 15
LKYNVFPYT                                                             9
```

```
SEQ ID NO: 16           moltype = AA   length = 115
FEATURE                 Location/Qualifiers
REGION                  1..115
                        note = Synthetic
source                  1..115
                        mol_type = protein
                        organism = synthetic construct
SEQUENCE: 16
QVQLLESGGG LVQPGGSLRL SCAASGFTFS SYTMSWVRQA PGQALEWMGT ISSRGTYTYY    60
PDSVKGRFTI SRDNAKNSLY LQMNSLRAED TAVYYCAREA IFTHWGRGTL VTVSS         115

SEQ ID NO: 17           moltype = AA   length = 107
FEATURE                 Location/Qualifiers
REGION                  1..107
                        note = Synthetic
source                  1..107
                        mol_type = protein
                        organism = synthetic construct
SEQUENCE: 17
DIQLTQSPSS LSASVGDRVT ITCKASQDIN NYHSWYQQKP GQAPRLLIYR ANRLVDGVPD    60
RFSGSGYGTD FTLTINNIES EDAAYYFCLK YNVFPYTFGQ GTKVEIK                  107

SEQ ID NO: 18           moltype = AA   length = 237
FEATURE                 Location/Qualifiers
REGION                  1..237
                        note = Synthetic
source                  1..237
                        mol_type = protein
                        organism = synthetic construct
SEQUENCE: 18
QVQLLESGGG LVQPGGSLRL SCAASGFTFS SYTMSWVRQA PGQALEWMGT ISSRGTYTYY    60
PDSVKGRFTI SRDNAKNSLY LQMNSLRAED TAVYYCAREA IFTHWGRGTL VTVSSGGGGS    120
GGGGSGGGGS DIQLTQSPSS LSASVGDRVT ITCKASQDIN NYHSWYQQKP GQAPRLLIYR    180
ANRLVDGVPD RFSGSGYGTD FTLTINNIES EDAAYYFCLK YNVFPYTFGQ GTKVEIK       237

SEQ ID NO: 19           moltype = DNA   length = 22
FEATURE                 Location/Qualifiers
misc_feature            1..22
                        note = Synthetic
source                  1..22
                        mol_type = other DNA
                        organism = synthetic construct
SEQUENCE: 19
cagagcctcg cctttgccga tc                                             22

SEQ ID NO: 20           moltype = DNA   length = 22
FEATURE                 Location/Qualifiers
misc_feature            1..22
                        note = Synthetic
source                  1..22
                        mol_type = other DNA
                        organism = synthetic construct
SEQUENCE: 20
catccatggt gagctggcgg cg                                             22

SEQ ID NO: 21           moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 21
ggggcaagat ggtaatgaag                                                20

SEQ ID NO: 22           moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 22
ccaggatact gagggcatgt                                                20

SEQ ID NO: 23           moltype = DNA   length = 20
FEATURE                 Location/Qualifiers
misc_feature            1..20
```

```
                            note = Synthetic
source                      1..20
                            mol_type = other DNA
                            organism = synthetic construct
SEQUENCE: 23
gctgcactttggagtgatcg                                                      20

SEQ ID NO: 24               moltype = DNA   length = 20
FEATURE                     Location/Qualifiers
misc_feature                1..20
                            note = Synthetic
source                      1..20
                            mol_type = other DNA
                            organism = synthetic construct
SEQUENCE: 24
tcactcggggttcgagaaga                                                      20

SEQ ID NO: 25               moltype = DNA   length = 20
FEATURE                     Location/Qualifiers
misc_feature                1..20
                            note = Synthetic
source                      1..20
                            mol_type = other DNA
                            organism = synthetic construct
SEQUENCE: 25
ataccatgtcttgggtgcga                                                      20

SEQ ID NO: 26               moltype = DNA   length = 20
FEATURE                     Location/Qualifiers
misc_feature                1..20
                            note = Synthetic
source                      1..20
                            mol_type = other DNA
                            organism = synthetic construct
SEQUENCE: 26
aatcggccctcacactgtc                                                       20

SEQ ID NO: 27               moltype = AA   length = 15
FEATURE                     Location/Qualifiers
REGION                      1..15
                            note = Synthetic
source                      1..15
                            mol_type = protein
                            organism = synthetic construct
SEQUENCE: 27
GGGGSGGGGS GGGGS                                                          15

SEQ ID NO: 28               moltype = DNA   length = 1242
FEATURE                     Location/Qualifiers
misc_feature                1..1242
                            note = Synthetic
source                      1..1242
                            mol_type = other DNA
                            organism = synthetic construct
SEQUENCE: 28
atggccttac cagtgaccgc cttgctcctg ccgctggcct tgctgctcca cgccgccagg         60
ccgcaggtgc agctgttgga gtctggggga ggcttggtac agcctggggg gtccctgaga        120
ctctcctgtg cagcctctgg attcaccttt agcagctata ccatgtcttg ggtgcgacag        180
gccccgggac aagcgcttga gtggatggga accattagta gtcgtggtac ttacacctac        240
tatccagaca gtgtgaaggg ccgattcacc atctccagag acaacgccaa gaactcactg        300
tatctgcaaa tgaacagcct gagagccgag gacacggctg tgtattactg tgcgagagaa        360
gctatctttta ctcactgggg ccgtggcacc ctggtcaccg tctcctcagg tggtggtggt       420
tctggcggcg gcggctccgg tggtggtggt tctgacatcc agttgaccca gtctccatcc        480
tccctgtctg catctgtagg agacagagtc accatcactt gcaaggcgag tcaggacatt        540
aataactatc acagctggta ccagcagaaa cctggccagg ctcccaggct ccctcatctat       600
cgtgcaaaca gattggtaga tggggtccca gacaggttca gtggcagcgg gtatggaaca        660
gatttttaccc tcacaattaa taacatgaa tctgaggatg ctgcatatta cttctgtctg        720
aaatataatg tgtttccgta cacgttcggc caagggacca aggtggagat caaaaccacg        780
acgccagcgc cgcgaccacc aacaccggcg cccaccatcg cgtcgcagcc cctgtccctg        840
cgcccagagg cgtgccggcc agcggcgggg ggcgcagtgc acacgagggg gctgactttc        900
gcctgtgata tctacatctg gcgcccctta gccgggactt gtggggtcct tctcctgtca        960
ctggttatca ccctttactg ccgctggcct ccttctgcag cttgttcggg aaaagagtca       1020
gttgttgcta taaggaccaa tagccaatct gacttccact acaaacttta tggagatgaa       1080
gatttgaatg aattagatcc tcattatgaa atgcgactga agatccaagt gcgaaaggca       1140
gctataacca gctatgagaa atcagatggt gtttacacgg gcctgagcac caggaaccag       1200
gagacttacg agactctgaa gcatgagaaa ccaccacagt aa                          1242

SEQ ID NO: 29               moltype = AA   length = 31
FEATURE                     Location/Qualifiers
```

```
REGION                  1..31
                        note = Synthetic
source                  1..31
                        mol_type = protein
                        organism = synthetic construct
SEQUENCE: 29
EDSSGNLLGR NSFEVHVCAC PGRDRRTEEE N                                    31

SEQ ID NO: 30           moltype = AA   length = 21
FEATURE                 Location/Qualifiers
REGION                  1..21
                        note = Synthetic
source                  1..21
                        mol_type = protein
                        organism = synthetic construct
SEQUENCE: 30
TEYKLVVVGA CGVGKSALTI Q                                               21

SEQ ID NO: 31           moltype = AA   length = 21
FEATURE                 Location/Qualifiers
REGION                  1..21
                        note = Synthetic
source                  1..21
                        mol_type = protein
                        organism = synthetic construct
SEQUENCE: 31
TEYKLVVVGA VGVGKSALTI Q                                               21

SEQ ID NO: 32           moltype = AA   length = 5
FEATURE                 Location/Qualifiers
REGION                  1..5
                        note = Synthetic
source                  1..5
                        mol_type = protein
                        organism = synthetic construct
SEQUENCE: 32
GYQRI                                                                  5

SEQ ID NO: 33           moltype = DNA  length = 111
FEATURE                 Location/Qualifiers
misc_feature            1..111
                        note = Synthetic
source                  1..111
                        mol_type = other DNA
                        organism = synthetic construct
SEQUENCE: 33
atgggctacc agaggatcga agactccagt ggtaatctac tgggacggaa cagctttgag     60
gtgcatgttt gtgcctgtcc tgggagagac cggcgcacag aggaagagaa t             111

SEQ ID NO: 34           moltype = DNA  length = 81
FEATURE                 Location/Qualifiers
misc_feature            1..81
                        note = Synthetic
source                  1..81
                        mol_type = other DNA
                        organism = synthetic construct
SEQUENCE: 34
atgggctacc agaggatcac tgaatataaa cttgtggtag ttggagcttg tggcgtaggc     60
aagagtgcct tgacgataca g                                               81

SEQ ID NO: 35           moltype = DNA  length = 81
FEATURE                 Location/Qualifiers
misc_feature            1..81
                        note = Synthetic
source                  1..81
                        mol_type = other DNA
                        organism = synthetic construct
SEQUENCE: 35
atgggctacc agaggatcac tgaatataaa cttgtggtag ttggagctgt tggcgtaggc     60
aagagtgcct tgacgataca g                                               81

SEQ ID NO: 36           moltype = DNA  length = 574
FEATURE                 Location/Qualifiers
misc_feature            1..574
                        note = Synthetic
source                  1..574
                        mol_type = other DNA
                        organism = synthetic construct
SEQUENCE: 36
```

```
ccctctccc tcccccccc ctaacgttac tggccgaagc cgcttggaat aaggccggtg    60
tgcgtttgtc tatatgttat tttccaccat attgccgtct tttggcaatg tgagggcccg   120
gaaacctggc cctgtcttct tgacgagcat tcctaggggt cttcccctc tcgccaaagg   180
aatgcaaggt ctgttgaatg tcgtgaagga agcagttcct ctggaagctt cttgaagaca   240
aacaacgtct gtagcgaccc tttgcaggca gcggaacccc ccacctggcg acaggtgcct   300
ctgcggccaa aagccacgtg tataagatac acctgcaaag gcggcacaac cccagtgcca   360
cgttgtgagt tggatagttg tggaaagagt caaatggctc tcctcaagcg tattcaacaa   420
ggggctgaag gatgcccaga aggtacccca ttgtatggga tctgatctgg ggcctcggtg   480
cacatgcttt acatgtgttt agtcgaggtt aaaaaaacgt ctaggccccc cgaaccacgg   540
ggacgtggtt ttcctttgaa aaacacgatg ataa                              574

SEQ ID NO: 37             moltype = AA  length = 129
FEATURE                   Location/Qualifiers
source                    1..129
                          mol_type = protein
                          organism = synthetic construct
SEQUENCE: 37
MAIYKQSQHM TEVVRHCPHH ERCSDSDGLA PPQHLIRVEG NLRVEYLDDR NTFRHSVVVP    60
YEPPEVGSDC TTIHYNYMCN SSCMGGMNQS PILTIITLED SSGNLLGRNS FEVHVCACPG   120
RDRRTEEEN                                                           129

SEQ ID NO: 38             moltype = DNA  length = 387
FEATURE                   Location/Qualifiers
misc_feature              1..387
                          note = Synthetic
source                    1..387
                          mol_type = other DNA
                          organism = synthetic construct
SEQUENCE: 38
atggccatct acaagcagtc acagcacatg acggaggttg tgaggcactg cccccaccat    60
gagcgctgct cagatagcga tggtctggcc cctcctcagc atcttatccg agtggaagga   120
aatttgcgtg tggagtattt ggatgacaga aacactttc gacatagtgt ggtggtgccc   180
tatgagccgc ctgaggttgg ctctgactgt accaccatcc actacaacta catgtgtaac   240
agttcctgca tgggcggcat gaaccagagc cccatcctca ccatcatcac actggaagac   300
tccagtggta atctactggg acggaacagc tttgaggtgc atgtttgtgc ctgtcctggg   360
agagaccggc gcacagagga agagaat                                      387
```

DENDRITIC CELL TUMOR VACCINE AND USES THEREOF

CROSS-REFERENCE TO RELATED APPLICATIONS

This is a continuation application of a PCT International Patent Application no. PCT/CN2023/071170, filed Jan. 9, 2023, which claims priority of a PCT International Patent Application no. PCT/CN2022/071239, filed Jan. 11, 2022 and a PCT International Patent Application no. PCT/CN2022/138288, filed Dec. 12, 2022, the disclosure of which is incorporated herein by reference in their entirety.

REFERENCE TO A "SEQUENCE LISTING", A TABLE, OR A COMPUTER PROGRAM LISTING APPENDIX SUBMITTED ON A COMPACT DISC AND AN INCORPORATION-BY-REFERENCE OF THE MATERIAL ON THE COMPACT DISC

The sequence listing that is contained in the file named "082971-8002US01-sequence list", which is 51,501 bytes and was created on Jan. 9, 2023, is filed herewith by electronic submission and is incorporated by reference herein.

TECHNICAL FIELD

The present disclosure generally relates to the field of cancer therapy. In particular, the present disclosure relates to dendritic cell tumor vaccine, the composition and methods of making the dendritic cell tumor vaccine, and methods of using the dendritic cell tumor vaccine to treat cancer.

BACKGROUND OF THE INVENTION

As a key link between innate and adaptive immunity, dendritic cells (DCs) play pivotal roles in the immune system (R. M. Steinman, Decisions about dendritic cells: past, present, and future. Annu. Rev. Immunol. 30, 1-22 (2012); and S. Puhr et al., Dendritic cell development-History, advances, and open questions. Semin. Immunol. 27, 388-396 (2015)). DCs are the major antigen presenting cells (APCs) to activate T cell-dependent immunity, especially in triggering tumor-specific immune responses (M. Hansen et al., The role of dendritic cells in cancer. Semin. Immunopathol. 39, 307-316 (2017)). In recent years, dendritic cell adoptive cell therapy has made great progress and become an important method of tumor immunotherapy.

Tumor vaccine is a vaccine that uses tumor-associated antigen (TAA) or tumor-specific antigen (TSA) to induce the body to produce specific anti-tumor effects through active immunization, stimulate the body's own immune protection mechanism, and achieve the effect of treating tumors or preventing recurrence. Tumor vaccines can be divided into therapeutic vaccines and preventive vaccines according to their different purposes. According to different ingredients and production methods, tumor vaccines can be divided into protein peptide vaccines, gene vaccines, virus vaccines and dendritic cell vaccines (DC vaccines). Provenge® (Sipuleucel-T) dendritic cell vaccine is the world's first and only therapeutic cancer vaccine that has been approved by the US FDA. At present, most of the DC vaccines in clinical trials are induced and differentiated in vitro from monocytes in the peripheral blood of patients. They are loaded with TAA or TSA using pulse protein peptides or gene transduction, and then injected back into the patient to stimulate tumor-specific T cells that can kill the tumor cells.

Recent studies have revealed that tumor-infiltrating dendritic cells (TIDCs) usually exhibit an immature or dysfunctional phenotype in immune suppressive tumor microenvironment or tumor immune suppressive microenvironment (TIME), which suppresses the infiltration and activation of T cells (J. M. Tran Janco et al., Tumor-infiltrating dendritic cells in cancer pathogenesis. J. Immunol. 194, 2985-2991 (2015)). As a result, DC vaccines face an obstacle to stimulate tumor-specific T cells in TIME. Therefore, need exists for developing new DC vaccines with promoted infiltration and activation effect in TIME.

SUMMARY OF THE INVENTION

In one aspect, the present disclosure provides a composition comprising one or more vectors. In some embodiments, the one or more vectors comprises: (a) a first polynucleotide encoding a chimeric antigen receptor (CAR) capable of activating a dendritic cell, wherein the CAR comprises (1) an extracellular antigen-binding domain, (2) a transmembrane domain and (3) an intracellular signaling domain, and (b) a second polynucleotide encoding a tumor antigen.

In some embodiments, the CAR and/or the tumor antigen when expressed in the dendritic cell is capable of activating the dendritic cell in an immune suppressive tumor microenvironment. In some embodiments, the immune suppressive tumor microenvironment comprises a tumor and/or tumor infiltrating immune cells that are: 1) expressing an immune inhibitory molecule, and/or 2) deficient in an immune stimulating cytokine. In some embodiments, the immune inhibitory molecule is selected from the group consisting of PD-1, TIM-3, TIGIT, LAG-3, A2AR, BTLA (CD272), CTLA-4 (CD152), IDO1, IDO2, TDO, NOX2, VISTA, SIGLEC7 (CD328), PVR(CD155) and SIGLEC9 (CD329), PD-L1, PD-L2, B7-H3 (CD276), B7-H4 (VTCN1), PVR(CD155), HLA class I, sialoglycoprotein, CD112, CD113, Galectin9, CD24, and CD47. In some embodiments, the immune inhibitory molecule is CTLA-4 and/or PD-L1. In some embodiments, the immune stimulating cytokine is selected from TNF-a, IFN-β, IFN-γ, IL-1, IL-2, IL-4, IL-6, IL-8, IL-10, IL-12, IL-18, granulocyte-macrophage colony stimulating factor and a combination thereof.

In some embodiments, the intracellular signaling domain comprises a cytoplasmic domain of a dendritic cell activating receptor selected from the group consisting of RIG-1, NLRP10, DEC-205, BDCA-2, CD86, 4-1BBL, OX40L, CD40, IFNAR, TLR4, TNFR (e.g., TNFR2), CD80, CD40L, CD367 (DCIR), CD207 (Langerin), CD371 (DCAL-2, CLEC12a), CD204, CD36, IFNγR, Dectin-1 and FcγR, or a combination thereof. In some embodiments, the intracellular signaling domain comprises the cytoplasmic domain of Dectin-1 and the cytoplasmic domain of FcγR. In some embodiments, the cytoplasmic domain of Dectin-1 comprises an amino acid sequence set forth in SEQ ID NO: 1, or any functional forms thereof. In some embodiments, the cytoplasmic domain of FcγR comprises an amino acid sequence set forth in SEQ ID NO: 2 or any functional forms thereof. In some embodiments, the intracellular signaling domain comprises an amino acid sequence set forth in SEQ ID NO: 3 or any functional forms thereof. In some embodiments, the intracellular signaling domain comprises an amino acid sequence encoded by a nucleic acid sequence set forth in SEQ ID NO: 4 or any functional forms thereof.

In some embodiments, the extracellular antigen-binding domain comprises a single-chain variable fragment (scFv). In some embodiments, the scFv is specific for a tumor surface marker. In some embodiments, the tumor surface marker is selected from the group consisting of: EphA2, CD19, CD70, CD133, CD147, CD171, DLL3, EGFRvIII, Mesothelin, ganglioside GD2, FAP (fibroblast activating protein), FBP (folate binding protein), Lewis Y, Claudin 18.2, IL13Ra2, HER2, MDC1, PMSA (prostate membrane specific antigen), ROR1, B7-H3, CAIX, CD133, CD171, CEA, GPC3, MUC1, NKG2D.

In some embodiments, the CAR further comprises a signal peptide. In some embodiments, the signal peptide comprises a signal peptide of CD8 alpha. In some embodiments, the signal peptide of CD8 alpha comprises a sequence set forth in SEQ ID NO: 5 or any functional forms thereof.

In some embodiments, the transmembrane domain comprises a transmembrane domain of CD8 alpha. In some embodiments, the transmembrane domain of CD8 alpha comprises a sequence set forth in SEQ ID NO: 6, or any functional forms thereof.

In some embodiments, the extracellular antigen-binding domain is linked to the transmembrane domain by a hinge region. In some embodiments, the hinge region comprises a hinge region of CD8 alpha. In some embodiments, the hinge region of CD8 alpha comprises a sequence set forth in SEQ ID NO: 7, or any functional forms thereof.

In some embodiments, the tumor antigen is a tumor associated antigen (TAA) or tumor specific antigen (TSA). In some embodiments, the tumor antigen is encoded by a mutated tumor gene or a fragment thereof. In some embodiments, the tumor gene is selected from p53, ras, beta-catenin, BRCA1/2, CDK4, CML66, fibronectin, MART-2, TGF-betaRII. In some embodiments, the tumor antigen is selected from CEA, immature laminin receptor, TAG-72, HPV E6, HPV E7, BING-4, calcium-activated chloride channel 2, cyclin-B1, 9D7, Ep-Cam, EphA3, GPC3, Her2/neu, telomerase, mesothelin, SAP-2, and surviving. In some embodiments, the tumor antigen is selected from a p53R273H mutated peptide, a KRAS G12V mutated peptide, and a KRAS G12C mutated peptide. In some embodiments, the p53 R273H mutated peptide has a sequence set forth in SEQ ID NO: 29, the KRAS G12V mutated peptide has a sequence set forth in SEQ ID NO: 31, and the KRAS G12C mutated peptide has a sequence set forth in SEQ ID NO: 30.

In some embodiments, the tumor antigen is linked to a DC-LAMP sorting signal. In some embodiments, the DC-LAMP sorting signal has a sequence set forth in SEQ ID NO: 32, or any functional forms thereof.

In some embodiments, the one or more vectors are DNA or RNA vectors.

In some embodiments, the first polynucleotide and/or the second polynucleotide is operatively linked to at least one regulatory polynucleotide element for expression of the CAR and/or the tumor antigen.

In some embodiments, the first polynucleotide and the second polynucleotide are comprised in a single vector. In some embodiments, the first polynucleotide is operably linked to the second polynucleotide via an IRES. In some embodiments, the IRES has a sequence set forth in SEQ ID NO: 36, or any functional forms thereof.

In some embodiments, the vector is a plasmid vector, a viral vector, a transposon, a site directed insertion vector, or a suicide expression vector. In some embodiments, the viral vector is a lentiviral vector, a retroviral vector, or an AAV vector. In some embodiments, the viral vector is a lentiviral vector.

In another aspect, the present disclosure provides an engineered cell comprising the one or more vectors as disclosed herein. In some embodiments, the engineered cell is a dendritic cell or a precursor or progenitor cell thereof. In some embodiments, the dendritic cell or a precursor or progenitor cell thereof is derived from a peripheral blood cell, a bone marrow cell, an embryonic stem cell, or an induced pluripotent stem cell.

In yet another aspect, the present disclosure provides a method of producing the engineered cells, comprising introducing to a starting cell the one or more vector as disclosed herein under conditions suitable for expression of the CAR and the tumor antigen. In some embodiments, the starting cell is a dendritic cell or a precursor or a progenitor cell thereof. In some embodiments, the dendritic cell or a precursor or a progenitor cell thereof is derived from a peripheral blood cell, a bone marrow cell, an embryonic stem cell, or an induced pluripotent stem cell.

In another aspect, the present disclosure provides a population of cells produced ex vivo by the method producing the engineered cells as disclosed herein. In some embodiments, at least 60% of the population of cells express a detectable level of the polypeptide of CAR.

In another aspect, the present disclosure provides a pharmaceutical composition comprising (i) the one or more vectors disclosed herein, or the population of the engineered cells disclosed herein or the population of cells disclosed herein, and (ii) a pharmaceutically acceptable medium.

In another aspect, the present disclosure provides a method for treating cancer in a subject in need thereof. In some embodiments, the method comprises administering to the subject the pharmaceutical composition disclosed herein. In some embodiments, the subject has a tumor cell bearing a mutated gene.

In some embodiments, the cancer is a solid cancer selected from the group consisting of adrenal cancer, bone cancer, brain cancer, breast cancer, colorectal cancer, esophageal cancer, eye cancer, gastric cancer, head and neck cancer, kidney cancer, liver cancer, lung cancer, non-small cell lung cancer, bronchioloalveolar cell lung cancer, mesothelioma, head and neck cancer, squamous cell carcinoma, melanoma, oral cancer, ovarian cancer, cervical cancer, penile cancer, prostate cancer, pancreatic cancer, skin cancer, sarcoma, testicular cancer, thyroid cancer, uterine cancer, vaginal cancer.

In some embodiments, the cancer is a hematologic malignancy selected from the group consisting of diffuse large B-cell lymphoma (DLBCL), extranodal NK/T-cell lymphoma, HHV8-associated primary effusion lymphoma, plasmablastic lymphoma, primary CNS lymphoma, primary mediastinal large B-cell lymphoma, T-cell/histiocyte-rich B-cell lymphoma, Hodgkin's lymphoma, non-Hodgkin's lymphoma, Waldenstrom's macroglobulinemia, multiple myeloma (MM).

In some embodiments, the method for treating cancer further comprises administering to the subject a population of modified immune cells. In some embodiments, the modified immune cells have expression of synthetic receptors (e.g., CARs or TCRs) on the cell surface. In some embodiments, the immune cell is a T cell, a Natural Killer (NK) cell, a NKT cell, a B cell, a macrophage cell, an eosinophil or a neutrophil. In some embodiments, the immune cell is a T cell, selected from the group consisting of CD4+ T cell, CD8+ T cell, cytotoxic T cell, terminal effector T cell, memory T cell, naïve T cell, natural killer T cell, gamma-delta T cell, cytokine-induced killer (CIK) T cell, and tumor infiltrating lymphocyte. In some embodiments, the immune cell is autologous or allogeneic.

In another aspect, the present disclosure provides a method of inducing proliferation of immune cells, prolonging the survival of immune cells, and/or increasing expression and/or secretion of immune stimulating cytokines from immune cells in an immune suppressive microenvironment. In some embodiments, the method comprises contacting the immune suppressive microenvironment with the engineered cell disclosed herein. In some embodiments, the immune cell is a T cell, a Natural Killer (NK) cell, a NKT cell, a B cell, a macrophage cell, an eosinophil or a neutrophil. In some embodiments, the immune cell is a T cell selected from the group consisting of CD4+ T cell, CD8+ T cell, cytotoxic T cell, terminal effector T cell, memory T cell, naïve T cell, natural killer T cell, gamma-delta T cell, cytokine-induced killer (CIK) T cell, and tumor infiltrating lymphocyte. In some embodiments, the immune cell is autologous or allogeneic.

In some embodiments, the immune suppressive microenvironment is an immune suppressive tumor microenvironment.

BRIEF DESCRIPTION OF DRAWINGS

The accompanying drawings, which are incorporated herein, form part of the specification. Together with this written description, the drawings further serve to explain the principles of, and to enable a person skilled in the relevant art(s), to make and use the present disclosure.

FIGS. 1A-1J show the expression of chimeric antigen receptor (CARDF) on the surface of the cells transduced with a lentiviral vector for co-expressing the CARDF and a tumor antigen. FIG. 1A shows the structural diagram of the lentiviral vector. FIG. 1B shows the expression of CARDF on the cell surface detected by flow cytometry after 293FT cells were transduced with the lentivirus. FIG. 1C shows the sequencing results of the p53 gene in H460 tumor cells. FIG. 1D shows the sequencing results of the p53 gene in SW480 tumor cell. FIG. 1E shows the sequencing of the KRAS gene in SW837 tumor cells. FIG. 1F shows the sequencing results of the KRAS gene in SW480 tumor cell. FIG. 1G shows the expression level of EphA2 on the surface of H460 tumor cells. FIG. 1H shows the expression level of EphA2 on the surface of SW480 tumor cells. FIG. 1I shows the expression level of EphA2 on the surface of SW837 tumor cells. FIG. 1J shows the mRNA level of the p53R273H mutant polypeptide expressed in the H460 tumor cell (hereinafter referred to as H460-p53R273Hov) which over-expresses p53R273H.

FIG. 2A shows the DCs differentiated from the humanized mouse bone marrow cells. FIG. 2B shows the mRNA level of p53R273H expressed in the DCs. FIG. 2C shows the DCs differentiated from the humanized mouse bone marrow cells and the expression of CARDF-KRAS G12C and KRAS G12V in the DCs. FIG. 2D shows the mRNA level of KRAS G12C and KRAS G12V expressed in the DCs.

FIG. 3A shows a schematic diagram of the treatment process using p53R273H vaccine. FIG. 3B shows a schematic diagram of KRAS G12C vaccine and the treatment process using KRAS G12C vaccine. FIG. 3C shows the growth curve of H460 tumor tissue during the treatment in different treatment groups using p53R273H vaccine. FIG. 3D shows the growth curve of H460-p53R273Hov (overexpressing R273H) tumor tissue during the treatment in different treatment groups using p53R273H vaccine. FIG. 3E shows the growth curve of SW480 tumor tissue during the treatment in different treatment groups using p53R273H vaccine. FIG. 3F shows the growth curve of SW480 tumor tissue during the treatment in different treatment groups using KRAS vaccine. FIG. 3G shows the growth curve of SW837 tumor tissue during the treatment in different treatment groups using KRAS vaccine.

FIG. 4A shows the ratio of T cells in the spleen of the different treatment groups of p53R273H vaccine. FIG. 4B shows the ratio of PD-1+ T cells in the spleen of the different treatment groups. shows the ratio of T cells in the spleen of the different treatment groups of p53R273H vaccine. FIG. 4C shows the ratio of T cells in the spleen of the different treatment groups of KRAS vaccine. FIG. 4D shows the ratio of DC cells in the spleen of the different treatment groups of KRAS vaccine. FIG. 4E shows the average fluorescence intensity of CD80 expression in DCs in the spleen of the different treatment groups of p53R273H vaccine. FIG. 4F shows the ratio of B cells in peripheral blood of different treatment groups of p53R273H vaccine. FIG. 4G shows the ratio of macrophages in peripheral blood of different treatment groups of p53R273H vaccine. FIG. 4H shows the ratio of B cells in peripheral blood of different treatment groups of KRAS vaccine.

FIG. 5A-5D shows the tumor mRNA analysis results in a humanized mouse (Hu-mice) tumor model after being treated with the dendritic cell tumor vaccine. FIG. 5A shows the TNF-α gene mRNA expression level in sw480 tumor tissues of the different treatment groups of p53R273H vaccine. FIG. 5B shows the CARDF scFv gene mRNA expression level in sw480 tumor tissues of different treatment groups of p53R273H vaccine. FIG. 5C shows the CD3 gene mRNA expression level in SW480 tumor tissues of the different treatment groups of KRAS vaccine. FIG. 5D shows the TNF-α gene mRNA expression level in SW837 tumor tissues of the different treatment groups of KRAS vaccine.

FIG. 5E shows primers sequences used in the present disclosure.

DETAILED DESCRIPTION OF THE INVENTION

Figure 1A:
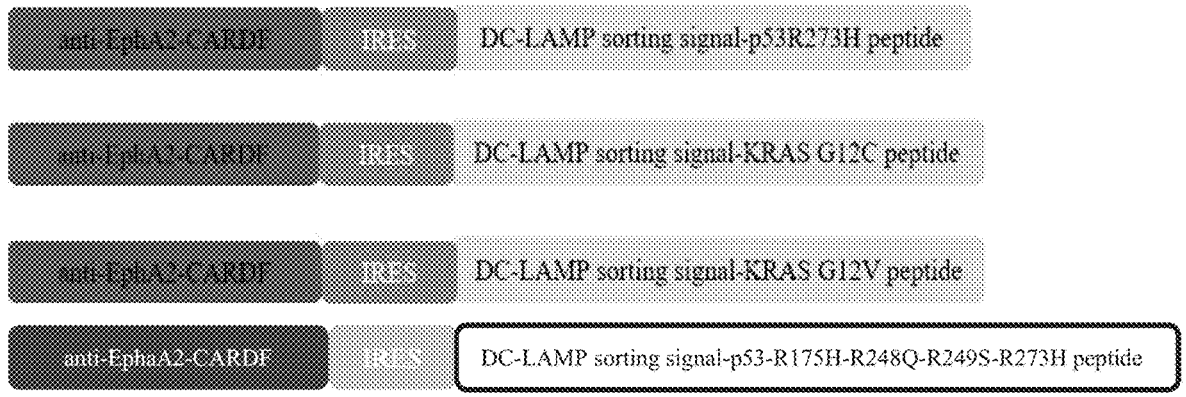

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Definition

The following definitions are provided to assist the reader. Unless otherwise defined, all terms of art, notations and other scientific or medical terms or terminology used herein are intended to have the meanings commonly understood by those of skill in the art. In some cases, terms with commonly understood meanings are defined herein for clarity and/or for ready reference, and the inclusion of such definitions herein should not necessarily be construed to represent a substantial difference over the definition of the term as generally understood in the art.

As used herein, the singular forms "a", "an" and "the" include plural references unless the context clearly dictates otherwise.

It is noted that in this disclosure, terms such as "comprises", "comprised", "comprising", "contains", "containing" and the like have the meaning attributed in United States Patent law; they are inclusive or open-ended and do not exclude additional, un-recited elements or method steps. Terms such as "consisting essentially of" and "consists essentially of" have the meaning attributed in United States Patent law; they allow for the inclusion of additional ingredients or steps that do not materially affect the basic and novel characteristics of the claimed invention. The terms "consists of" and "consisting of" have the meaning ascribed to them in United States Patent law; namely that these terms are close ended.

In all occurrences in this application where there are a series of recited numerical values, it is to be understood that any of the recited numerical values may be the upper limit or lower limit of a numerical range. It is to be further understood that the invention encompasses all such numerical ranges, i.e., a range having a combination of an upper numerical limit and a lower numerical limit, wherein the numerical value for each of the upper limit and the lower limit can be any numerical value recited herein. Ranges provided herein are understood to include all values within the range. For example, 1-10 is understood to include all of the values 1, 2, 3, 4, 5, 6, 7, 8, 9, and 10, and fractional values as appropriate. Similarly, ranges delimited by "at least" are understood to include the lower value provided and all higher numbers.

As used herein, "about" is understood to include within three standard deviations of the mean or within standard ranges of tolerance in the specific art. In certain embodiments, about is understood as a variation of no more than 0.5.

As used herein, the term "CAR" or "CARDF", which can be used interchangeably with the term "chimeric antigen receptor" refers to an engineered receptor or a synthetic receptor or polynucleotide encoding thereof. The engineered receptor or a synthetic receptor comprises an extracellular domain that comprises an antigen binding domain, a transmembrane domain, and/or an intracellular signaling domain, optionally a signal peptide, which are joined one another or operably linked to each other. The most common CARs are, for example, a single-chain variable fragment (scFv) derived from a monoclonal antibody fused to CD3-zeta transmembrane and endodomain. Such CARs result in the transmission of a zeta signal in response to specific binding of scFv to its target. Methods of preparing CARs are publicly available (see, e.g., Grupp et al., N Engl J Med., 368:1509-1518, 2013; Park et al., Trends Biotechnol., 29:550-557, 2011; Haso et al., (2013) Blood, 121, 1165-1174; Han et al., J. Hematol Oncol. 6:47, 2013; WO2012/079000; U.S. Pub.2012/0213783; and WO2013/059593, each of which is incorporated by reference herein in its entirety).

The term "chimeric antigen receptor T cell", used interchangeably with the term "CAR-T cell", refers to a T cell or population thereof that has been engineered through biological methods (e.g., genetic engineering) to express a CAR on the T cell surface. CAR-T cells can be T helper CD4+ and/or T effector CD8+ cells. CAR-T can identify surface antigens and initiate immune response.

"Antigen" refers to a molecule that provokes an immune response. This immune response may be either humoral, or cell-mediated response, or both. The skilled artisan will understand that any macromolecule, including virtually all proteins or peptides, can serve as an antigen. It is readily apparent that the present disclosure includes therapeutic antibodies acting as antigen eliciting immune response.

The term "neoantigen" as used herein refers to an antigen that has at least one alteration that makes it distinct from its corresponding wild-type parental antigen. The alteration can be made via, for example, mutation in a tumor cell or post-translational modification specific to a tumor cell. A mutation can include a splice site alteration, a splice variant, frameshift or non-frameshift indel, genomic rearrangement or gene fusion, missense or nonsense substitution, or any genomic or expression alteration giving rise to a neoORF. A post-translational modification can include aberrant phosphorylation and proteasome-generated spliced antigen. A neoantigen can include a polypeptide sequence or a nucleotide sequence.

"Antibody" refers to a polypeptide of the immunoglobulin (Ig) family that binds with an antigen. For example, a naturally occurring "antibody" of the IgG type is a tetramer comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain (abbreviated herein as CL). The VH and VL regions can be further subdivided into regions of hypervariability, termed complementarity determining regions (CDR) (light chain CDRs including LCDR1, LCDR2, and LCDR3, heavy chain CDRs including HCDR1, HCDR2, HCDR3), interspersed with regions that are more conserved, termed framework regions (FR). CDR boundaries for the antibodies disclosed herein may be defined or identified by the conventions of Kabat, IMGT, Chothia, or Al-Lazikani (Al-Lazikani, B., Chothia, C., Lesk, A. M., J. Mol. Biol., 273(4), 927 (1997); Chothia, C. et al., J Mol Biol. December 5; 186(3):651-63 (1985); Chothia, C. and Lesk, A. M., J. Mol. Biol., 196,901 (1987); Chothia, C. et al., Nature. December 21-28; 342(6252):877-83 (1989); Kabat E. A. et al., National Institutes of Health, Bethesda, Md. (1991); Marie-Paule Lefranc et al, Developmental and Comparative Immunology, 27: 55-77 (2003); Marie-Paule Lefranc et al, Immunome Research, 1(3), (2005); Marie-Paule Lefranc, Molecular Biology of B cells (second edition), chapter 26, 481-514, (2015)). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen.

"Antigen-binding domain" as used herein refers to an antibody fragment formed from a portion of an intact antibody comprising one or more CDRs, or any other antibody fragment that can bind to an antigen but does not comprise an intact native antibody structure. Examples of antigen-binding domain include, without limitation, a diabody, a Fab, a Fab', a F(ab')2, an Fv fragment, a disulfide stabilized Fv fragment (dsFv), a (dsFv)2, a bispecific dsFv (dsFv-dsFv'), a disulfide stabilized diabody (ds diabody), a single-chain antibody molecule (scFv), single-chain Fv-Fc antibody (scFv-Fc), an scFv dimer (bivalent diabody), a bispecific antibody, a multispecific antibody, a camelized single domain antibody, a nanobody, a domain antibody, and a bivalent domain antibody. An antigen-binding domain is capable of binding to the same antigen to which the parent antibody binds.

"Autologous" cells refer to any cells derived from the same subject into which they are later to be re-introduced.

"Allogeneic" cells refer to any cells derived from a different subject of the same species.

"Effector cells" used in the context of immune cells refers to cells that can be activated to carry out effector functions in response to stimulation. Effector cells may include, without limitation, NK cells, cytotoxic T cells and helper T cells.

"Effective amount" or "therapeutically effective amount" refers to an amount of a cell, composition, formulation or any material as described here effective to achieve a desirable biological result. Such results may include, without limitation, elimination of B cells expressing a specific BCR and the antibodies produced therefrom.

Percentage of "identity" or "sequence identity" in the context of polypeptide or polynucleotide is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "conservative substitution", as used herein with reference to amino acid sequence refers to replacing an amino acid residue with a different amino acid residue having a side chain with similar physiochemical properties. For example, conservative substitutions can be made among amino acid residues with hydrophobic side chains (e.g. Met, Ala, Val, Leu, and Ile), among residues with neutral hydrophilic side chains (e.g. Cys, Ser, Thr, Asn and Gln), among residues with acidic side chains (e.g. Asp, Glu), among amino acids with basic side chains (e.g. His, Lys, and Arg), or among residues with aromatic side chains (e.g. Trp, Tyr, and Phe). As known in the art, conservative substitution usually does not cause significant change in the protein conformational structure, and therefore could retain the biological activity of a protein.

The term "functional forms" as used herein, refers to different forms (such as variants, fragments, fusions, derivatives and mimetics) of the parent molecule, which, despite of having difference in amino acid sequences or in chemical structures, still retains substantial biological activity of the parent molecule. The expression "retain substantial biological activity", as used herein, means exhibiting at least part of (for example, no less than about 20%, 30%, 40%, 50%, 60%, 70%, 80%, or 90%) or all of the biological activity of the parent molecule. A functional form of a parent polypeptide may include both naturally-occurring variant forms and non-naturally occurring forms such as those obtained by recombinant methods or chemical synthesis. The functional forms may contain non-natural amino acid residues.

As used herein, the term "operably linked" refers to a functional relationship between two or more polynucleotide sequences. In the context of a polynucleotide encoding a fusion protein, such as a polypeptide chain of a CAR of the disclosure, the term means that the two or more polynucleotide sequences are joined such that the amino acid sequences encoded by these segments remain in-frame. In the context of transcriptional or translational regulation, the term refers to the functional relationship of a regulatory sequence to a coding sequence, for example, a promoter in the correct location and orientation to the coding sequence so as to modulate the transcription.

As used herein, the term "polynucleotide" or "nucleic acid" refers to a chain of nucleotides. They also refer to synthetic and/or non-naturally occurring nucleic acid molecules (e.g., comprising nucleotide analogues or modified backbone residues or linkages). The terms also refer to deoxyribonucleotide or ribonucleotide oligonucleotides in either single-stranded or double-stranded form. The terms encompass nucleic acids containing analogues of natural nucleotides. The terms also encompass nucleic acid-like structures with synthetic backbones. Unless otherwise indicated, a particular polynucleotide sequence also implicitly encompasses conservatively modified variants thereof (e.g. degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (see Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "polypeptide", "peptide" and "protein" are used interchangeably herein to refer to a polymer of amino acid residues. The terms also apply to amino acid polymers in which one or more amino acid residue is an artificial chemical mimetic of a corresponding naturally-occurring amino acid, as well as to naturally-occurring amino acid polymers and non-naturally occurring amino acid polymers. In certain embodiments, the polypeptides include natural peptides, recombinant peptides, synthetic peptides, or a combination thereof.

As used herein, the term "single-chain variable fragment" used interchangeably with the term "scFv" refers to an engineered antibody consisting of a light chain variable region and a heavy chain variable region connected to one another directly or via a peptide linker sequence (Huston J S et al. Proc Natl Acad Sci USA, 85:5879(1988)).

As used herein, the term "TCR", which can be used interchangeably with the term "T cell receptor" or the term "TCR complex" refers to a natural (or endogenous) TCR or an engineered TCR. TCR refers to a protein complex on the surface of T cells that is responsible for recognizing fragments of antigen as peptides bound to MHC molecules.

The term "vector" as used herein refers to a vehicle into which a polynucleotide encoding a protein may be operably inserted so as to bring about the expression of that protein. A vector may be used to transform, transduce, or transfect a host cell so as to bring about expression of the genetic element it carries within the host cell. Examples of vectors include plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Categories of animal viruses used as vectors include retrovirus (including lentivirus), adenovirus, adeno-associated virus, herpesvirus (e.g., herpes simplex virus), poxvirus, baculovirus, papillomavirus, and papovavirus (e.g., SV40). A vector may contain a variety of elements for controlling expression, including promoter sequences, transcription initiation sequences, enhancer sequences, selectable elements, and reporter genes. In addition, the vector may contain an origin of replication. A vector may also include materials to aid in its entry into the cell, including but not limited to a viral particle, a liposome, or a protein coating. A vector can be an expression vector or a cloning vector. The present disclosure provides vectors (e.g., expression vectors) containing the nucleic acid sequence provided herein encoding the fusion polypeptide, at least one promoter (e.g., SV40, CMV, EF-1α) operably linked to the nucleic acid sequence, and at least one selection marker. Examples of vectors include, but are not limited to, retrovirus (including lentivirus), adenovirus, adeno-associated virus, herpesvirus (e.g., herpes simplex virus), poxvirus, baculovirus, papillomavirus, papovavirus (e.g., SV40), lambda phage, and M13 phage, plasmid pcDNA3.3, pMD18-T, pOptivec, pCMV, pEGFP, pIRES, pQD-Hyg-GSeu, pALTER, pBAD, pcDNA, pCal, pL, pET, pGEMEX, pGEX, pCI, pEGFT, pSV2, pFUSE, pVITRO, pVIVO, pMAL, pMONO, pSELECT, pUNO, pDUO, Psg5L, pBABE, pWPXL, pBI, p15TV-L, pPro18, pTD, pRS10, pLexA, pACT2.2, pCMV-SCRIPT®, pCDM8, pCDNA1.1/amp, pcDNA3.1, pRc/RSV, PCR 2.1, pEF-1, pFB, pSG5, pXT1, pCDEF3, pSVSPORT, pEF-Bos etc.

The phrase "host cell" as used herein refers to a cell into which an exogenous polynucleotide and/or a vector has been introduced.

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

The term "subject" or "individual" or "animal" or "patient" as used herein refers to human or non-human animal, including a mammal or a primate, in need of diagnosis, prognosis, amelioration, prevention and/or treatment of a disease or disorder. Mammalian subjects include humans, domestic animals, farm animals, and zoo, sports, or pet animals such as dogs, cats, guinea pigs, rabbits, rats, mice, horses, swine, cows, bears, and so on.

The term "treating", or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

Dendritic Cell (DC) Tumor Vaccine

The present disclosure provides a novel DC vaccine platform that can stimulate immune response even in an immune suppressive environment. For example, the DC vaccine platform provided herein has improved anti-tumor activity compared to conventional DC vaccines, especially for solid tumors that are commonly associated with a tumor immune suppressive microenvironment. The DC vaccine platform provided herein is capable of carrying one or more (e.g., 1, 2, 3, 4, 5, or more) of a variety of known or unknown tumor or non-tumor antigens. Accordingly, the DC vaccine platform provided herein can be used to treat a wide spectrum of diseases, such as cancers bearing certain mutations or infectious diseases. It can also be used to improve the efficacy of personalized neoantigen vaccines.

While most of the conventional DC vaccines need to be used in combination with another cancer therapy to achieve desirable therapeutic effects, the DC vaccine platforms provided herein can be used as a monotherapy to treat tumors, even to treat solid tumors that are commonly associated with a tumor immune suppressive microenvironment. This makes the DC vaccine platform provided herein a promising cancer therapy to treat a large variety of cancers, especially solid tumors, which are known to be difficult to be treated by conventional cancer therapies, such as CAR-T monotherapy or DC vaccine monotherapy.

In one aspect, the present disclosure provides a dendritic cell (DC) tumor vaccine capable of stimulating tumor-specific T cells in an immune suppressive tumor microenvironment or tumor immune suppressive microenvironment (TIME). In one embodiment, the DC tumor vaccine comprises a dendritic cell or a precursor or progenitor cell thereof which express a chimeric antigen receptor (CAR or CARDF) that is capable of activating dendritic cells (DCs) and a tumor antigen.

Tumor Immune Suppressive Microenvironment

The term "immune suppressive tumor microenvironment" and the term "tumor immune suppressive microenvironment (TIME)" can be used interchangeably, and refers to a microenvironment having, for example, tumor cells, tumor infiltrating immune cells, tumor associated fibroblasts, endothelial cells, and various chemotactic and inflammatory or immune stimulating cytokines, which, together with a dense extracellular matrix, capable of suppressing tumor immune surveillance and immunotherapy (F. R. Balkwill et al., The tumor microenvironment at a glance. J. Cell Sci. 125, 5591-5596 (2012); M. Binnewies et al., Understanding the tumor immune microenvironment (TIME) for effective therapy. Nat Med. 24, 541-550 (2018); M. A.-M. Alireza Labani-Motlagh et al., The Tumor Microenvironment: A Milieu Hindering and Obstructing Antitumor Immune Responses. Front. Immunol. 11, 940 (2020) and L. Hui et al., Tumor microenvironment: Sanctuary of the devil. Cancer Lett. 368, 7-13 (2015)).

In certain embodiments, the immune suppressive tumor microenvironment or TIME comprises a solid tumor and/or tumor infiltrating immune cells expressing an immune inhibitory molecule. The immune inhibitory molecule can be selected from the group consisting of PD-1, TIM3, TIGIT, LAG3, A2AR, BTLA (CD272), CTLA-4 (CD152), IDO1, IDO2, TDO, NOX2, VISTA, SIGLEC7 (CD328), PVR(CD155) and SIGLEC9 (CD329), PD-L1, PD-L2, B7-H3 (CD276), B7-H4 (VTCN1), PVR(CD155), HLA class I, sialoglycoprotein, CD112, CD113, Galectin9, CD24, and CD47. In certain embodiments, the immune inhibitory molecule is CTLA-4 and/or PD-L1. As used herein, the term "expressing" or "express" with respect to an immune inhibitory molecule, refers to expressing an immune inhibitory molecule at a level that is at least 10%, 20%, 30%, 40%, 50%, 60%, 70%, 80%, 90% higher than a reference level. The term "reference level" with respect to the expression of an immune inhibitory molecule refers to an expression level of the immune inhibitory molecule in a tumor formed by wild-type tumor cells (e.g., wild-type A549 cells) in an immune-deficient animal model (e.g., NSG mouse).

"CTLA-4" is short for Cytotoxic T-Lymphocyte-Associated protein 4 and is also known as CD152, and more detailed description can be found in, for example, Kolar et al., (Jan. 1, 2009) CTLA-4 (CD152) controls homeostasis and suppressive capacity of regulatory T cells in mice. Arthritis Rheum. 60 (1): 123-32. "PD-L1" is short for programmed death-ligand 1 and is also known as cluster of differentiation 274 (CD274) or B7 homolog 1 (B7-H1), and more detailed description can be found in, for example, Dong H et al., B7-H1, a third member of the B7 family, co-stimulates T-cell proliferation and interleukin-10 secretion. Nature Medicine. 5 (12): 1365-9, 1999.

CTLA-4 and PD-L1 are critical immune inhibitory molecules in maintaining peripheral tolerance by restraining T cell activity. CTLA-4 binds to CD80 and CD86 with higher affinity than CD28, which are the primary co-stimulation pathways for activating T cells. PD-L1 binds to PD-1 that is expressed on T cell surface and inhibits T cell activity. PD-L1 plays a central role in maintaining T cell anergy and preventing autoimmunity (Walker L S K et al., The enemy within: keeping self-reactive T cells at bay in the periphery. Nat Rev Immunol. 2002; 2:11-19; Fife B T et al., Control of peripheral T-cell tolerance and autoimmunity via the CTLA-4 and PD-1 pathways. Immunological Reviews. 2008; 224:166-182; and Keir M E et al., PD-1 and Its Ligands in Tolerance and Immunity. Annual Review of Immunology. 2008; 26:677-704).

In certain embodiments, the tumor within TIME comprises a cell expressing CTLA-4-immunoglobulin fusion protein (CTLA4-Ig) and/or PD-L1. CTLA4-Ig has been developed to inhibit T cell-mediated immune responses (Walker L S K et al., The enemy within: keeping self-reactive T cells at bay in the periphery. Nat Rev Immunol. 2002; 2:11-19). As used herein, the term "expressing" or "express" with respect to CTLA4-Ig, refers to expressing CTLA4-Ig at a level that is at least 10%, 20%, 30%, 40%, 50%, 60%, 70%, 80%, 90% higher than a reference level. The term "reference level" with respect to the expression of CTLA4-Ig refers to an expression level of the CTLA4-Ig in a wild-type tumor cell (e.g., wild-type A549 cells). As used herein, the term "expressing" or "express" with respect to PD-L1, refers to expressing PD-L1 at a level that is at least 10%, 20%, 30%, 40%, 50%, 60%, 70%, 80%, 90% higher than a reference level. The term "reference level" with respect the expression of PD-L1 refers to an expression level of the PD-L1 in a wild-type tumor cell (e.g., wild-type A549 cells).

In certain embodiments, the CTLA-4-Ig comprises an amino acid sequence set forth in SEQ ID NO:8 or a sequence having at least 75%, 80%, 85%, 90%, 95%, or 99% identity thereto while retaining substantial biological activity of SEQ ID NO:8, or a sequence having 1, 2, 3, 4, 5, 6, 7, 8, 9 or 10 conservative substitutions thereof, or any functional forms thereof. In certain embodiments, the PD-L1 comprises an amino acid sequence set forth in SEQ ID NO: 9 or a sequence having at least 75%, 80%, 85%, 90%, 95%, or 99% identity thereto while retaining substantial biological activity of SEQ ID NO: 9, or a sequence having 1, 2, 3, 4, 5, 6, 7, 8, 9 or 10 conservative substitutions thereof, or any functional forms thereof.

In certain embodiments, the immune suppressive tumor microenvironment comprises a tumor that has poor responsiveness to monotherapy of adoptive cell therapy (e.g., CAR-T monotherapy). As used herein and throughout the specification, the term "poor responsiveness" refers to absence or reduced of responsiveness, which can be detected by a comparable (for example, less than 20%, less than 15%, less than 10%, less than 5%, less than 4%, less than 3% or less than 2% better therapeutical effect) therapeutical effect of a therapy (e.g., CAR-T therapy) as compared to a control treatment that is known to have no therapeutical effect.

Dendritic Cell Activating Chimeric Antigen Receptor

Dendritic cells are professional antigen-presenting cells that can prime naïve T cells and reactivate memory responses. In cancer, dendritic cells can activate T cells (e.g., cytotoxic CD8+ T cells) through cross-presentation of tumor associated antigens (TAAs) or neoantigens to elicit a stronger anti-tumor response. The activation of a DC can be assayed by measuring various parameters, including, without limitation, the activation status of DC and/or the activation status of immune cells (e.g., T cells, microphages), which can be indicated by the expression level of DC activating markers (such as CD80, CD86 and MHC-II, CD83, CD54, CMRF-44, CMRF-56), the survival and/or cytotoxicity of the immune cells (e.g., T cells), the expression (and/or secretion) of immune stimulating cytokines (e.g., TNF-a, IFN-β, IFN-γ, IL-1, IL-2, IL-4, IL-6, IL-8, IL-10, IL-12, IL-18 and granulocyte-macrophage colony stimulating factor) from the immune cells (e.g., T cells), the expression level of immune inhibitory molecules (e.g., PD-1, TIM-3, TIGIT, LAG3, A2AR, BTLA (CD272), CTLA-4 (CD152), IDO1, IDO2, TDO, KIR, NOX2, VISTA, SIGLEC7 (CD328), PVR(CD155), and SIGLEC9 (CD329)) from the immune cells (e.g., T cells), and/or the expression level of markers for anti-inflammatory macrophages (e.g., M2 macrophages), such as CD206 and CD163.

In certain embodiments, the activation of dendritic cells comprises increased expression level of DC activating markers (such as CD80, CD86 and/or MHC-II, CD83, CD54, CMRF-44, CMRF-56), increased survival of the immune cells (e.g., T cells (such as CD8+ T cells), DCs), increased expression (and/or secretion) of immune stimulating cytokines (e.g., TNF-a, IFN-β, IFN-γ, IL-1, IL-2, IL-4, IL-6, IL-8, IL-10, IL-12, IL-18 and/or granulocyte-macrophage colony stimulating factor) from the immune cells (e.g., T cells), decreased expression of immune inhibitory molecules (e.g., PD-1, TIM-3, TIGIT, LAG3, A2AR, BTLA (CD272), CTLA-4 (CD152), IDO1, IDO2, TDO, KIR, NOX2, VISTA, SIGLEC7 (CD328), PVR(CD155), and SIGLEC9 (CD329)) from the immune cells (e.g., T cells), and/or decreased expression level of markers (such as CD206 and CD163) for anti-inflammatory macrophages (e.g., M2 macrophages), when compared to a reference status (e.g., inactivated status) of dendritic cells.

In certain embodiments, the DC-activating CAR provided herein comprises: (1) an extracellular antigen-binding domain, (2) a transmembrane domain and (3) an intracellular signaling domain.

(1) Extracellular Antigen-Binding Domain

The extracellular antigen-binding domain can be any domain that is capable of recognizing and binding to a marker specifically expressed on a target cell, such that the CAR-DC vaccine provided herein comprising the DC-activating CAR is brought in proximity to the target cell. In certain embodiments, the extracellular antigen-binding domain is an antigen, such as a tumor marker expressed on surface of a cancer cell (i.e., tumor surface marker), or an antigen expressed on an infected cell. The design of an extracellular antigen-binding domain is well-known in the art. In certain embodiments, the extracellular antigen-binding domain is the antigen-binding domain of an antibody. In some embodiments, the antigen binding domain comprises a human or humanized antibody or an antibody fragment thereof. The term "human antibody" refers to an antibody where the whole molecule is of human origin or consists of an amino acid sequence identical to a human form of the antibody or immunoglobulin. The term "humanized antibody" refers to an antibody which contains sequence (e.g., CDR sequences) derived from non-human immunoglobulin. Human or humanized antibodies or fragments thereof may be prepared in a variety of ways, for example through recombinant methodologies or through immunization with an antigen of interest of a mouse that is genetically modified to express antibodies derived from human heavy and/or light chain-encoding genes.

In some embodiments, the extracellular antigen-binding domain of the CAR provided herein comprises a single-chain variable fragment (scFv), a Fv, a Fab, a (Fab)2, an scFv, a nanobody, ligand/receptor domain or any alternative scaffold known in the art to function as antigen binding domain. In some embodiments, the extracellular antigen-binding domain of the CAR provided herein is a scFv. The scFv can be specific to a tumor surface marker, for example a solid tumor surface marker. The term "tumor surface marker" as used herein refers to a molecule differentially expressed on surface of a tumor cell to be used as a target for recognizing a tumor cell. In certain embodiments, the tumor surface marker is selected from the group consisting of: EphA2, CD19, CD70, CD117, CD133, CD147, CD171, DLL3, EGFRvIII, VGFR2, Mesothelin, ganglioside GD2, FAP (fibroblast activating protein), FBP (folate binding protein), LMP1, Lewis Y, Claudin 18.2, IL13R☐2, HER2, MDC1, PMSA (prostate membrane specific antigen), ROR1, ROR2, B7-H3, CAIX, CD133, CD171, CEA, GPC3, MUC1, MUC16, MAGE-A1, MAGE-A4, TROP2, EpCAM, NKG2D, other proteins found to be more highly enriched on the surface of tumor cells than critical normal tissues, and combination thereof. The extracellular antigen-binding domain can also be specific to non-tumor markers for diseases that can benefit from converting TIME towards a pro-inflammatory state, for example, markers for infectious diseases.

In some embodiments, the scFv is specific for EphA2. In some embodiments, the scFv comprises a variable heavy (VH) and variable light (VL) region. In some embodiments, the VH comprises a heavy chain CDR1 (HCDR1) having a sequence set forth in SEQ ID NO:10, or a sequence having at least 75%, 80%, 85%, 90%, 95%, or 99% identity thereto while retaining substantial biological activity thereof, or a sequence having 1, 2, 3, 4, 5, 6, 7, 8, 9 or 10 conservative substitutions thereof, or any functional forms thereof, a CDR2 having a sequence set forth in SEQ ID NO:11, or a sequence having at least 75%, 80%, 85%, 90%, 95%, or 99% identity thereto while retaining substantial biological activity thereof, or a sequence having 1, 2, 3, 4, 5, 6, 7, 8, 9 or 10 conservative substitutions thereof, or any functional forms thereof, and a CDR3 having a sequence set forth in SEQ ID NO: 12, or a sequence having at least 75%, 80%, 85%, 90%, 95%, or 99% identity thereto while retaining substantial biological activity thereof, or a sequence having 1, 2, 3, 4, 5, 6, 7, 8, 9 or 10 conservative substitutions thereof, or any functional forms thereof. In some embodiments, the VL region comprises a light chain CDR1 (LCDR1) having a sequence set forth in SEQ ID NO:13, or a sequence having at least 75%, 80%, 85%, 90%, 95%, or 99% identity thereto while retaining substantial biological activity thereof, or a sequence having 1, 2, 3, 4, 5, 6, 7, 8, 9 or 10 conservative substitutions thereof, or any functional forms thereof, a CDR2 having a sequence set forth in SEQ ID NO: 14, or a sequence having at least 75%, 80%, 85%, 90%, 95%, or 99% identity thereto while retaining substantial biological activity thereof, or a sequence having 1, 2, 3, 4, 5, 6, 7, 8, 9 or 10 conservative substitutions thereof, or any functional forms thereof, and a CDR3 having a sequence set forth in SEQ ID NO:15, or a sequence having at least 75%, 80%, 85%, 90%, 95%, or 99% identity thereto while retaining substantial biological activity thereof, or a sequence having 1, 2, 3, 4, 5, 6, 7, 8, 9 or 10 conservative substitutions thereof, or any functional forms thereof.

In certain embodiments, the scFv comprises 1) a VH comprising a HCDR1 comprising a sequence set forth in SEQ ID NO:10, a HCDR2 comprising a sequence set forth in SEQ ID NO:11, a HCDR3 comprising a sequence set forth in SEQ ID NO: 12; and 2) a VL comprising a LCDR1 comprising a sequence set forth in SEQ ID NO:13, a LCDR2 comprising a sequence set forth in SEQ ID NO: 14, a LCDR3 comprising a sequence set forth in SEQ ID NO: 15.

In some embodiments, the scFv comprises a VH and a VL. In certain embodiments, the VH comprises an amino acid sequence set forth in SEQ ID NO: 16, or a sequence having at least 75%, 80%, 85%, 90%, 95%, or 99% identity thereto while retaining substantial biological activity thereof, or a sequence having 1, 2, 3, 4, 5, 6, 7, 8, 9 or 10 conservative substitutions thereof, or any functional forms thereof. In certain embodiments, the VL comprises an amino acid sequence set forth in SEQ ID NO:17, or a sequence having at least 75%, 80%, 85%, 90%, 95%, or 99% identity thereto while retaining substantial biological activity thereof, or a sequence having 1, 2, 3, 4, 5, 6, 7, 8, 9 or 10 conservative substitutions thereof, or any functional forms thereof. In some embodiments, the scFv comprises a VH comprising a sequence set forth in SEQ ID NO: 16, and a VL comprising a sequence set forth in SEQ ID NO: 17.

In certain embodiments, the scFv comprises a peptide linker of at least 0, 1, 2, 3, 6, 7, 8, 9, 10, 11, 12, 13, 14, 15, 16, 17, 18, 19, 20, 25, 30, 35, 40, 45, 50, or more amino acid residues between its VL and VH regions. The linker sequence may comprise any naturally occurring amino acid. In certain embodiments, the peptide linker comprises an amino acid sequence comprising SEQ ID NO:27 (GGGGSGGGGSGGGGS).

In some embodiments, the scFv comprises an amino acid sequence set forth in SEQ ID NO:18.

The skilled person in the art will appreciate that an appropriate extracellular antigen-binding domain specific for any disease marker may be selected to construct a CAR provided herein, depending on the disease of interest, in view of the existing knowledge of the identified markers for various diseases, such as cancer, infectious diseases, or immune diseases. The various disease markers include but not limited to those as described above.

(2) Transmembrane Domain

The transmembrane domain of the CAR described herein may be derived from any membrane-bound or transmembrane protein including, but are not limited to, BAFFR, BLAME (SLAMF8), CD2, CD3 epsilon, CD4, CD5, CD8, CD9, CD11a (CD18, ITGAL, LFA-1), CD11b, CD11c, CD11d, CD16, CD19, CD22, CD27, CD28, CD29, CD33, CD37, CD40, CD45, CD49a, CD49d, CD49f, CD64, CD80, CD84, CD86, CD96 (Tactile), CD100 (SEMA4D), CD103, CD134, CD137 (4-1BB), CD150 (IPO-3, SLAMF1, SLAM), CD154, CD160 (BY55), CD162 (SELPLG), CD226 (DNAM1), CD229 (Ly9), CD244 (2B4, SLAMF4), CD278 (ICOS), CEACAM1, CRT AM, GITR, HYEM (LIGHTR), IA4, IL2R beta, IL2R gamma, IL7R a, ITGA1, ITGA4, ITGA6, ITGAD, ITGAE, ITGAM, ITGAX, ITGB1, ITGB2, ITGB7, KIR, LTBR, OX40, NKG2C, NKG2D, NKp30, NKp44, NKp46, NKp80 (KLRF1), PAG/Cbp, PSGL1, SLAMF6 (NTB-A, Ly108), SLAMF7, an alpha, beta or zeta chain of a T-cell receptor, TNFR2, VLA1, and VLA-6.

In one embodiment, the CAR described herein comprises a transmembrane domain of CD8 alpha. In certain embodiments, the transmembrane domain of CD8 alpha has a sequence of SEQ ID NO:6, or a sequence having at least 75%, 80%, 85%, 90%, 95%, or 99% identity thereto while retaining substantial biological activity thereof, or a sequence having 1, 2, 3, 4, 5, 6, 7, 8, 9 or 10 conservative substitutions thereof, or any functional forms thereof.

In certain embodiments, the transmembrane domain of the CAR described herein is synthetic, e.g., comprising predominantly hydrophobic residues such as leucine and valine. In certain embodiment, the transmembrane domain of the CAR described herein is modified or designed to avoid binding to the transmembrane domains of the same or different surface membrane proteins in order to minimize interactions with other members of the receptor complex.

In some embodiments, the CAR described herein further comprises a hinge region, which forms the linkage between the extracellular domain and transmembrane domain of the CAR. The hinge and/or transmembrane domain provides cell surface presentation of the extracellular antigen-binding domain of the CAR.

The hinge region may be derived from any membrane-bound or transmembrane protein including, but are not limited to, BAFFR, BLAME (SLAMF8), CD2, CD3 epsilon, CD4, CD5, CD8, CD9, CD11a (CD18, ITGAL, LFA-1), CD11b, CD11c, CD11 d, CD16, CD19, CD22, CD27, CD28, CD29, CD33, CD37, CD40, CD45, CD49a, CD49d, CD49f, CD64, CD80, CD84, CD86, CD96 (Tactile), CD100 (SEMA4D), CD134, CD137 (4-1BB), CD150 (IPO-3, SLAMF1, SLAM), CD154, CD160 (BY55), CD162 (SELPLG), CD226 (DNAM1), CD229 (Ly9), CD244 (2B4, SLAMF4), CD278 (ICOS), CEACAM1, CRT AM, GITR, HYEM (LIGHTR), IA4, IL2R beta, IL2R gamma, IL7Ra, ITGA1, ITGA4, ITGA6, ITGAD, ITGAE, ITGAM, ITGAX, ITGB1, ITGB2, ITGB7, KIR, LTBR, OX40, NKG2C, NKG2D, NKp30, NKp44, NKp46, NKp80 (KLRF1), PAG/Cbp, PSGL1, SLAMF6 (NTB-A, Ly108), SLAMF7, an alpha, beta or zeta chain of a T-cell receptor, TNFR2, VLA1, and VLA-6.

In some embodiments, the hinge region comprises a hinge region of CD8 alpha, a hinge region of human immunoglobulin (Ig), or a glycine-serine rich sequence.

In some embodiments, the CAR comprises a hinge region of CD8 alpha. In certain embodiments, the hinge region has a sequence of SEQ ID NO:7, or a sequence having at least 75%, 80%, 85%, 90%, 95%, or 99% identity thereto while retaining substantial biological activity thereof, or a sequence having 1, 2, 3, 4, 5, 6, 7, 8, 9 or 10 conservative substitutions thereof, or any functional forms thereof.

(3) Intracellular Signaling Domain

The intracellular signaling domain of the CAR described herein is responsible for activation of at least one of the normal effector functions of the immune cell (e.g., dendritic cell) in which the CAR has been placed in. The term "effector function" used in the context of an immune cell refers to a specialized function of the cell, for example, the phagocytic activity, cytolytic activity or helper activity. In certain embodiments, the intracellular signaling domain of the CAR described herein is capable of activating (including maturation) dendritic cells in an immune suppressive tumor microenvironment. Activation of DCs can be induced by many cell surface receptors, such as TLR4 (A. Iwasaki et al., Toll-like receptor control of the adaptive immune responses. Nat. Immunol. 5, 987-995 (2004).), TNFR (L. M. Sedger et al., From mediators of cell death and inflammation to therapeutic giants—past, present and future. Cytokine Growth Factor Rev. 25, 453-472 (2014).), IFNγR (M. Z. Jianping Pan et al., Interferon-γ is an autocrine mediator for dendritic cell maturation. Immunol. Lett. 94, 141-151 (2004).), Dectin-1 (T. S. Helen S. et al., Differential utilization of CARD9 by Dectin-1 in macrophages and dendritic cells. J Immunol. 182, 1146-1154 (2009)) and FcγR (M. Guilliams et al., The function of Fcγ receptors in dendritic cells and macrophages. Nat. Rev. Immunol. 14, 94-108 (2014)., T. H. Flinsenberg, Fc receptor antigen targeting potentiates cross-presentation by human blood and lymphoid tissue BDCA-3 dendritic cells. Blood 120, 26 (2012).) in response to various stimuli. These DC activating receptors have an immune-receptor tyrosine-based activation motif (ITAM) in their cytoplasmic domains, which triggers activating signal cascades to activate DCs. As used herein, the term "cytoplasmic domain" refers to a fully length domain of a protein residing inside cytoplasm, or any fragment thereof, for example, a fragment having a length that is at least 1%, at least 2%, at least 3%, at least 4%, at least 5%, at least 10%, at least 20%, at least 30%, at least 40%, at least 50%, at least 60%, at least 70%, at least 80%, at least 90%, or at least 95% of the full length domain.

The intracellular signaling domain of the CAR described herein may comprise a cytoplasmic domain of a dendritic cell activating receptor selected from the group consisting of RIG-1, NLRP10, DEC-205, BDCA-2, CD86, 4-1BBL, OX40L, CD40, IFNAR, TLR4, TNFR (e.g., TNFR2), IFNγR, Dectin-1 and FcγR, or a combination thereof. In certain embodiments, the intracellular signaling domain of the CAR described herein comprises the cytoplasmic domain of Dectin-1 and the cytoplasmic domain of FcγR.

In certain embodiments, the cytoplasmic domain of Dectin-1 and the cytoplasmic domain of FcγR are connected in tandem. In certain embodiments, the polynucleotide encoding the cytoplasmic domain of Dectin-1 is upstream the polynucleotide encoding the cytoplasmic domain of FcγR. In certain embodiments, the polynucleotide encoding the cytoplasmic domain of Dectin-1 is downstream the polynucleotide encoding the cytoplasmic domain of FcγR.

The cytoplasmic domain of Dectin-1 may comprise an amino acid sequence set forth in SEQ ID NO:1, or a sequence having at least 75%, 80%, 85%, 90%, 95%, or 99% identity thereto while retaining substantial biological activity thereof, or a sequence having 1, 2, 3, 4, 5, 6, 7, 8, 9 or 10 conservative substitutions thereof, or any functional forms thereof.

The cytoplasmic domain of FcγR may comprise an amino acid sequence set forth in SEQ ID NO:2, or a sequence having at least 75%, 80%, 85%, 90%, 95%, or 99% identity thereto while retaining substantial biological activity thereof, or a sequence having 1, 2, 3, 4, 5, 6, 7, 8, 9 or 10 conservative substitutions thereof, or any functional forms thereof.

In certain embodiments, the intracellular signaling domain of the CAR described herein comprises an amino acid sequence set forth in SEQ ID NO:3, or a sequence having at least 75%, 80%, 85%, 90%, 95%, or 99% identity thereto while retaining substantial biological activity thereof, or a sequence having 1, 2, 3, 4, 5, 6, 7, 8, 9 or 10 conservative substitutions thereof, or any functional forms thereof.

In certain embodiments, the intracellular signaling domain of the CAR described herein comprises an amino acid sequence encoded by a nucleic acid sequence set forth in SEQ ID NO:4, or a sequence having at least 75%, 80%, 85%, 90%, 95%, or 99% identity thereto while retaining substantial biological activity thereof.

(4) Co-Stimulatory Signaling Domain

In some embodiments, the intracellular signaling domain further comprises a co-stimulatory signaling domain.

In some embodiments, the co-stimulatory signaling domain is derived from an intracellular domain of a co-stimulatory molecule.

Examples of co-stimulatory molecules include B7-H3, BAFFR, BLAME (SLAMF8), CD2, CD4, CD8 alpha, CD8 beta, CD7, CD11a, CD11b, CD11c, CD11d, CD18, CD 19, CD27, CD28, CD29, CD30, CD40, CD49a, CD49D, CD49f, CD69, CD83, CD84, CD96 (Tactile), CD100 (SEMA4D), CD103, CD 127, CD137(4-1BB), CD150 (SLAM, SLAMF1, IPO-3), CD160 (BY55), CD162 (SELPLG), CD226 (DNAM1), CD229 (Ly9), CD244 (SLAMF4, 2B4), CEACAM1, CRTAM, CDS, OX40, PD-1, ICOS, GADS, GITR, HVEM (LIGHTR), IA4, ICAM-1, IL2R beta, IL2R gamma, IL7R alpha, ITGA4, ITGA4, ITGA6, ITGAD, ITGAE, ITGAL, ITGAM, ITGAX, ITGB1, ITGB2, ITGB7, LAT, LFA-1, LIGHT, LTBR, NKG2C, NKG2D, NKp44, NKp30, NKp46, NKp80 (KLRF1), PAG/Cbp, PSGL1, SLAMF6 (NTB-A, Lyl08), SLAMF7, SLP-76, TNFR2, TRANCE/RANKL, VLA1, VLA-6, any derivative, variant, or fragment thereof, any synthetic sequence of a co-stimulatory molecule that has the same functional capability, and any combination thereof.

In some embodiment, the co-stimulatory signaling domain of the CAR described herein comprises an intracellular domain of co-stimulatory molecule CD137 (4-1BB), CD28, OX40 or ICOS. In some embodiments, the co-stimulatory signaling domain of the CAR described herein has a sequence of SEQ ID NO: 58. or a sequence having at least 80%, 85%, 90%, 91%, 92%, 93%, 94%, 95%, 96%, 97%, 98%, 99% sequence identity thereto.

Other Regions

In some embodiments, the CAR further comprises a signal peptide. In some embodiments, the signal peptide comprises a signal peptide of CD8 alpha. In some embodiments, the signal peptide of CD8 alpha comprises the sequence of SEQ ID NO: 5, or a sequence having at least 75%, 80%, 85%, 90%, 95%, or 99% identity thereto while retaining substantial biological activity thereof, or a sequence having 1, 2, 3, 4, 5, 6, 7, 8, 9 or 10 conservative substitutions thereof, or any functional forms thereof.

Tumor Antigen

Tumor antigen is an antigenic substance produced in tumor cells, i.e., it triggers an immune response in the host. Normal proteins in the body are not antigenic because of self-tolerance, a process in which self-reacting cytotoxic T lymphocytes (CTLs) and autoantibody-producing B lymphocytes are called "centrally" in primary lymphatic tissue (BM) and "peripherally" in secondary lymphatic tissue (mostly thymus for T-cells and spleen/lymph nodes for B cells). Thus, any protein that is not exposed to the immune system triggers an immune response. This may include normal proteins that are well sequestered from the immune system, proteins that are normally produced in extremely small quantities, proteins that are normally produced only in certain stages of development, or proteins whose structure is modified due to mutation.

Tumor antigens can be broadly classified into two categories based on their pattern of expression: Tumor-Specific Antigens (TSA), which are present only on tumor cells and not on any other cell and Tumor-Associated Antigens (TAA), which are present on some tumor cells and also some normal cells. More precisely, tumor antigens include products of mutated oncogenes and tumor suppressor genes; products of other mutated genes; overexpressed or aberrantly expressed cellular proteins; tumor antigens produced by oncogenic viruses; oncofetal antigens; altered cell surface glycolipids and glycoproteins; and cell type-specific differentiation Antigens.

Any protein produced in a tumor cell that has an abnormal structure due to mutation can act as a tumor antigen. Such abnormal proteins are produced due to mutation of the concerned gene. Mutation of protooncogenes and tumor suppressors which lead to abnormal protein production are the cause of the tumor and thus such abnormal proteins are called tumor-specific antigens. Examples of tumor-specific antigens include the abnormal products of ras and p53 genes. In contrast, mutation of other genes unrelated to the tumor formation may lead to synthesis of abnormal proteins which are tumor-associated antigens. Therefore, in some embodiments, the tumor antigen described herein is a peptide or polypeptide encoded by a mutated gene, i.e., a tumor gene, or a fragment thereof. In some embodiments, the tumor gene is selected from p53, ras, beta-catenin, BRCA1/2, CDK4, CML66, fibronectin, MART-2, TGF-betaRII.

In human tumors, p53 and RAS are the most frequently mutated genes. More than 50% of aggressive tumors have p53 mutations. p53 mutations can trigger the body to produce specific cytotoxic T cells for the mutation site, making it an ideal target for tumor vaccines. Among the multiple mutation types of p53, R175H, R248W, R273H are the three most common hotspot mutations. Other mutations include but are not limited to R248Q and R249S. Among KRAS gene mutations, 97% are mutations in the 12th or 13th amino acid. The most important ones are G12D, G12C, G12V and G13D. Structural studies have shown that most of these gene mutations interfere with the ability of KRAS to hydrolyze GTP.

Other examples of tumor antigens include tissue differentiation antigens, mutant protein antigens, oncogenic viral antigens, cancer-testis antigens and vascular or stromal specific antigens. Tissue differentiation antigens are those that are specific to a certain type of tissue. Mutant protein antigens are likely to be much more specific to cancer cells because normal cells shouldn't contain these proteins. Normal cells will display the normal protein antigen on their MHC molecules, whereas cancer cells will display the mutant version. Some viral proteins are implicated in forming cancer (oncogenesis), and some viral antigens are also cancer antigens. Cancer-testis antigens are antigens expressed primarily in the germ cells of the testes, but also in fetal ovaries and the trophoblast. Some cancer cells aberrantly express these proteins and therefore present these antigens, allowing attack by T-cells specific to these antigens. Example antigens of this type are CTAG1B and MAGEA1.

Proteins that are normally produced in very low quantities but whose production is dramatically increased in tumor cells, trigger an immune response. An example of such a protein is the enzyme tyrosinase, which is required for melanin production. Normally tyrosinase is produced in minute quantities but its levels are very much elevated in melanoma cells.

Oncofetal antigens are another important class of tumor antigens. Examples are alphafetoprotein (AFP) and carcinoembryonic antigen (CEA). These proteins are normally produced in the early stages of embryonic development and disappear by the time the immune system is fully developed. Thus self-tolerance does not develop against these antigens.

Abnormal proteins are also produced by cells infected with oncoviruses, e.g. EBV and HPV. Cells infected by these viruses contain latent viral DNA which is transcribed and the resulting protein produces an immune response.

Thus, in some embodiments, the tumor antigen used in the DC vaccine disclosed herein is selected from CEA, immature laminin receptor, TAG-72, HPV E6, HPV E7, BING-4, calcium-activated chloride channel 2, cyclin-B1, 9D7, Ep-Cam, EphA3, GPC3, Her2/neu, telomerase, mesothelin, SAP-2, and surviving.

In addition to proteins, other substances like cell surface glycolipids and glycoproteins may also have an abnormal structure in tumor cells and could thus be targets of the immune system.

p53

Tumor protein p53, also known as p53, cellular tumor antigen p53, phosphoprotein p53, tumor suppressor p53, antigen NY-CO-13, or transformation-related protein 53 (TRP53), is any isoform of a protein encoded by homologous genes in various organisms, such as TP53 (humans) and Trp53 (mice). This homolog (originally thought to be, and often spoken of as, a single protein) is crucial in multicellular organisms, where it prevents cancer formation, and thus functions as a tumor suppressor. As such, p53 has been described as "the guardian of the genome" because of its role in conserving stability by preventing genome mutation. Hence, TP53 is classified as a tumor suppressor gene.

The name p53 was given in 1979 describing the apparent molecular mass; SDS-PAGE analysis indicates that it is a 53-kilodalton (kDa) protein. However, the actual mass of the full-length p53 protein (p53a) based on the sum of masses of the amino acid residues is only 43.7 kDa. This difference is due to the high number of proline residues in the protein, which slow its migration on SDS-PAGE, thus making it appear heavier than it actually is. In addition to the full-length protein, the human TP53 gene encodes at least 15 protein isoforms, ranging in size from 3.5 to 43.7 kDa. All these p53 proteins are called the p53 isoforms. The TP53 gene is the most frequently mutated gene (>50%) in human cancer, indicating that the TP53 gene plays a crucial role in preventing cancer formation. TP53 gene encodes proteins that bind to DNA and regulate gene expression to prevent mutations of the genome.

In humans, the TP53 gene is located on the short arm of chromosome 17 (17p13.1). The gene spans 20 kb, with a non-coding exon 1 and a very long first intron of 10 kb. The coding sequence contains five regions showing a high degree of conservation in vertebrates, predominantly in exons 2, 5, 6, 7 and 8, but the sequences found in invertebrates show only distant resemblance to mammalian TP53. TP53 orthologs have been identified in most mammals for which complete genome data are available.

In humans, a common polymorphism involves the substitution of an arginine for a proline at codon position 72. Many studies have investigated a genetic link between this variation and cancer susceptibility; however, the results have been controversial. For instance, a meta-analysis from 2009 failed to show a link for cervical cancer. A 2011 study found that the TP53 proline mutation did have a profound effect on pancreatic cancer risk among males. A study of Arab women found that proline homozygosity at TP53 codon 72 is associated with a decreased risk for breast cancer. One study suggested that TP53 codon 72 polymorphisms, MDM2 SNP309, and A2164G may collectively be associated with non-oropharyngeal cancer susceptibility and that MDM2 SNP309 in combination with TP53 codon 72 may accelerate the development of non-oropharyngeal cancer in women. A 2011 study found that TP53 codon 72 polymorphism was associated with an increased risk of lung cancer.

Meta-analyses from 2011 found no significant associations between TP53 codon 72 polymorphisms and both colorectal cancer risk and endometrial cancer risk. A 2011 study of a Brazilian birth cohort found an association between the non-mutant arginine TP53 and individuals without a family history of cancer. Another 2011 study found that the p53 homozygous (Pro/Pro) genotype was associated with a significantly increased risk for renal cell carcinoma.

KRAS

KRAS (Kirsten rat sarcoma virus), or K-Ras, is a protein in the RAS/MAPK pathway, which relays signals from outside the cell to the cell's nucleus. These signals instruct the cell to grow and divide (proliferate) or to mature and take on specialized functions (differentiate). The K-Ras protein is a GTPase, which means it converts a molecule called GTP into another molecule called GDP. In this way the K-Ras protein acts like a switch that is turned on and off by the GTP and GDP molecules. To transmit signals, it must be turned on by attaching (binding) to a molecule of GTP. The K-Ras protein is turned off (inactivated) when it converts the GTP to GDP. When the protein is bound to GDP, it does not relay signals to the cell's nucleus. It is called KRAS because it was first identified as an oncogene in Kirsten Rat Sarcoma virus. The viral oncogene was derived from cellular genome. Thus, KRAS gene in cellular genome is called a proto-oncogene.

The gene product of KRAS was first found as a p21 GTPase. Like other members of the ras subfamily, the KRAS protein is a GTPase and is an early player in many signal transduction pathways. KRAS is usually tethered to cell membranes because of the presence of an isoprene group on its C-terminus. There are two protein products of the KRAS gene in mammalian cells that result from the use of alternative exon 4 (exon 4A and 4B respectively): K-Ras4A and K-Ras4B; these proteins have different structure in their C-terminal region and use different mechanisms to localize to cellular membranes including the plasma membrane.

Single amino acid substitutions, and in particular single nucleotide substitutions, of KRAS, may result in an activating mutation. The transforming protein that results is implicated in various malignancies, including lung adenocarcinoma, mucinous adenoma, ductal carcinoma of the pancreas and colorectal cancer. Several germline KRAS mutations have been found to be associated with Noonan syndrome and cardio-facio-cutaneous syndrome. Somatic KRAS mutations are found at high rates in leukemias, colorectal cancer, pancreatic cancer and lung cancer.

MUC1

Mucin 1, cell surface associated (MUC1), also called polymorphic epithelial mucin (PEM) or epithelial membrane antigen or EMA, is a mucin encoded by the MUC1 gene in humans. MUC1 is a glycoprotein with extensive O-linked glycosylation of its extracellular domain. Mucins line the apical surface of epithelial cells in the lungs, stomach, intestines, eyes and several other organs. Mucins protect the body from infection by pathogen binding to oligosaccharides in the extracellular domain, preventing the pathogen from reaching the cell surface. Overexpression of MUC1 is often associated with colon, breast, ovarian, lung and pancreatic cancers. Joyce Taylor-Papadimitriou identified and characterized the antigen during her work with breast and ovarian tumors. MUC1 is a member of the mucin family and encodes a membrane bound, glycosylated phosphoprotein. MUC1 has a core protein mass of 120-225 kDa which increases to 250-500 kDa with glycosylation. It extends 200-500 nm beyond the surface of the cell.

The protein is anchored to the apical surface of many epithelia by a transmembrane domain. Beyond the transmembrane domain is a SEA domain that contains a cleavage site for release of the large extracellular domain. The release of mucins is performed by sheddases. The extracellular domain includes a 20 amino acid variable number tandem repeat (VNTR) domain, with the number of repeats varying from 20 to 120 in different individuals. These repeats are rich in serine, threonine and proline residues which permits heavy o-glycosylation.

Multiple alternatively spliced transcript variants that encode different isoforms of this gene have been reported, but the full-length nature of only some has been determined.

MUC1 is cleaved in the endoplasmic reticulum into two pieces, the cytoplasmic tail including the transmembrane domain and the extracellular domain. These domains tightly associate in a non-covalent fashion. This tight, non-covalent association is not broken by treatment with urea, low pH, high salt or boiling. Treatment with sodium dodecyl sulfate triggers dissociation of the subunits. The cytoplasmic tail of MUC1 is 72 amino acids long and contains several phosphorylation sites.

The protein serves a protective function by binding to pathogens and also functions in a cell signaling capacity.

Overexpression, aberrant intracellular localization, and changes in glycosylation of this protein have been associated with carcinomas. e.g., the CanAg tumor antigen is a novel glycoform of MUC1. In the cell nucleus, the protein MUC1 regulates the activity of transcription factor complexes that have a documented role in tumor-induced changes of host immunity.

PSMA

Prostate-specific membrane antigen (PSMA), glutamate carboxypeptidase II (GCPII), also known as N-acetyl-L-aspartyl-L-glutamate peptidase I (NAALADase I) or NAAG peptidase, is an enzyme that in humans is encoded by the FOLH1 (folate hydrolase 1) gene. Human PSMA contains 750 amino acids and weighs approximately 84 kDa. PSMA is a zinc metalloenzyme that resides in membranes. Most of the enzyme resides in the extracellular space. PSMA is a class II membrane glycoprotein. It catalyzes the hydrolysis of N-acetylaspartylglutamate (NAAG) to glutamate and N-acetylaspartate (NAA) according to the reaction scheme to the right.

Neuroscientists primarily use the term NAALADase in their studies, while those studying folate metabolism use folate hydrolase, and those studying prostate cancer or oncology, PSMA, all of which refer to the same protein.

PSMA is mainly expressed in four tissues of the body, including prostate epithelium, the proximal tubules of the kidney, the jejunal brush border of the small intestine and ganglia of the nervous system.

Indeed, the initial cloning of the cDNA encoding the gene expressing PSMA was accomplished with RNA from a prostate tumor cell line, LNCaP. PSMA shares homology with the transferrin receptor and undergoes endocytosis but the ligand for inducing internalization has not been identified. It was found that PSMA was the same as the membrane protein in the small intestine responsible for removal of gamma-linked glutamates from polygammaglutamate folate. This enables the freeing of folic acid, which then can be transported into the body for use as a vitamin. This resulted in the cloned genomic designation of PSMA as FOLH1 for folate hydrolase.

The three domains of the extracellular portion of PSMA—the protease, apical and C-terminal domains—collaborate in substrate recognition. The protease domain is a central seven-stranded mixed β-sheet. The β-sheet is flanked by 10 α-helices. The apical domain is located between the first and the second strands of the central β-sheet of the protease domain. The apical domain creates a pocket that facilitates substrate binding. The C-terminal domain is an Up-Down-Up-Down four-helix bundle.

The central pocket is approximately 2 nanometers in depth and opens from the extracellular space to the active site. This active site contains two zinc ions. During inhibition, each acts as a ligand to an oxygen in 2-PMPA or phosphate. There is also one calcium ion coordinated in PSMA, far from the active site. It has been proposed that calcium holds together the protease and apical domains. In addition, human PSMA has ten sites of potential glycosylation, and many of these sites (including some far from the catalytic domain) affect the ability of PSMA to hydrolyze NAAG.

The FOLH1 gene has multiple potential start sites and splice forms, giving rise to differences in membrane protein structure, localization, and carboxypeptidase activity based on the parent tissue.

Human PSMA is highly expressed in the prostate, roughly a hundred times greater than in most other tissues. In some prostate cancers, PSMA is the second-most upregulated gene product, with an 8- to 12-fold increase over levels in noncancerous prostate cells. Because of this high expression, PSMA is being developed as potential biomarker for therapy and imaging of some cancers. In human prostate cancer, the higher expressing tumors are associated with quicker time to progression and a greater percentage of patients suffering relapse. In vitro studies using prostate and breast cancer cell lines with decreased PSMA levels showed a significant decrease in the proliferation, migration, invasion, adhesion and survival of the cells.

PSMA is the target of several nuclear medicine imaging agents for prostate cancer. Capromabpentide (marketed as PROSTASCINT) is bound to indium-111 for detection by a gamma camera. Second-generation antibodies and low-molecular-weight ligands for imaging and therapy are under development. PSMA can also be used experimentally to target treatment.

Lutetium-177 is a beta emitter, bound to PSMA to deliver treat prostate tumors. In addition to the human prostate and prostate cancer, PSMA is highly expressed in tumor neovasculature, but not corresponding normal vasculature of all types of solid tumors including the kidney, breast and colon.

S100P

S100 calcium-binding protein P (S100P) is a protein that in humans is encoded by the S100P gene. The protein encoded by this gene is a member of the S100 family of proteins containing 2 EF-hand calcium-binding motifs. S100 proteins are localized in the cytoplasm and/or nucleus of a wide range of cells and involved in the regulation of a number of cellular processes such as cell cycle progression and differentiation. S100 genes include at least 13 members which are located as a cluster on chromosome 1q21; however, this gene is located at 4p16. This protein, in addition to binding Ca2+, also binds Zn2+ and Mg2+. This protein may play a role in the etiology of prostate cancer. S100P has been shown to interact with EZR and RAGE. The interactions between S100P and RAGE are disrupted by cromolyn and pentamidine.

Neoantigen

Neoantigens can be identified using conventional techniques known in the art, such as whole genome/exome sequencing, and RNA sequencing. In particular, neoantigens can be identified by sequencing the tumor and normal DNA of each patient to identify tumor-specific mutations, and determining the patient's HLA allotype. The population of tumor specific neoantigens and their cognate native antigens may then be subject to bioinformatic analysis using validated algorithms to predict which tumor-specific mutations create epitopes that could bind to the patient's HLA allotype (e.g., which tumor-specific mutations create epitopes that could bind to the patient's HLA allotype more effectively than the cognate native antigen). Detailed discerption of the identification of neoantigens for cancer therapy can be found in, e.g., US 2016/0101170 A1, disclosure of which is incorporated by reference herein by its entirety. Based on this analysis, polynucleotides encoding one or more peptides corresponding to a subset of these mutations may be loaded onto the CAR-DC vaccine platform provided herein to form a personalized cancer vaccine.

Vector

In another aspect, the present disclosure provides one or more vector comprising a first polynucleotide encoding the CAR as described herein and a second polynucleotide encoding the tumor antigen as described herein. The polynucleotides encoding the CAR and/or tumor antigen can be inserted into different types of vectors known in the art, for example, a plasmid, a phagemid, a phage derivative, a viral vector derived from animal virus, a cosmid, transposon, a site directed insertion vector (e.g., CRISPR, Zinc finger nucleases, TALEN), an in vitro transcribed RNA, or a suicide expression vector. In some embodiments, the vector is a DNA or RNA.

In some embodiments, the vector is an expression DNA vector (e.g., plasmid, virus). When the expression DNA vector introduced into the cell transiently, mRNA of the CAR will be transcribed in host cell. As the DNA vector and the mRNA would dilute out with cell division, the expression of the CAR would not be permanent. In one embodiment, the DNA vector can be introduced to a cell as a form of transient expression of the CAR.

In some embodiments, the vector is a viral vector. Viral vectors may be derived from, for example, retroviruses, adenoviruses, adeno-associated viruses (AAV), herpes viruses, and lentiviruses. Useful viral vectors generally contain an origin of replication functional in at least one organism, a promoter, restriction endonuclease sites, and one or more selectable markers. In some embodiments, the vector is a lentiviral vector. Lentiviral vector is particular useful for long-term, stable integration of the polynucleotide encoding the CAR into the genome of non-proliferating cells that result in stable expression of the CAR in the host cell, e.g., host T cell. In some embodiments, the vector is a lenti-Cas9 vector from Addgene.

In some embodiments, the vector is RNA (e.g., mRNA). As the RNA would dilute out with cell division, the expression of the RNA would not be permanent. In one embodiment, the in vitro transcribed RNA CAR can be introduced to a cell as a form of transient expression.

In some embodiments, the vector is a transposon-based expression vector. A transposon is a DNA sequence that can change its position within a genome. In a transposon system, the polynucleotide encoding the CAR is flanked by terminal repeat sequences recognizable by a transposase which mediates the movement of the transposon. A transposase can be co-delivered as a protein, encoded on the same vector as the CAR, or encoded on a separate vector. Non-limiting examples of transposon systems include Sleeping Beauty, Piggyback, Frog Prince, and Prince Charming.

In some embodiment, the polynucleotide is operably linked to at least one regulatory polynucleotide element in the vector for expression of the CAR. Typical vectors contain various regulatory polynucleotide elements, for example, elements (e.g., transcription and translation terminators, initiation sequences, and promoters) regulating the expression of the inserted polynucleotides, elements (e.g., origin of replication) regulating the replication of the vector in a host cell, and elements (e.g., terminal repeat sequence of a transposon) regulating the integration of the vector into a host genome. The expression of the CAR can be achieved by operably linking the polynucleotides encoding a CAR to a promoter and incorporating the construct into a vector. Both constitutive promoters (such as a CMV promoter, a SV40 promoter, and a MMTV promoter), or inducible promoters (such as a metallothionine promoter, a glucocorticoid promoter, and a progesterone promoter) are contemplated for the disclosure. In some embodiment, the vector is an expression vector, an expression vector comprises sufficient cis-acting elements for expression; other elements for expression can be supplied by the host cell or in an in vitro expression system.

In order to assess the expression of a CAR, the vector can also comprise a selectable marker gene or a reporter gene or both for identification and selection of the cells to which the vector is introduced. Useful selectable markers include, for example, antibiotic-resistance genes, such as neo and the like. Useful reporters include, for example, luciferase, betagalactosidase, chloramphenicol acetyl transferase, secreted alkaline phosphatase, or the green fluorescent protein gene.

Chemical structures with the ability to promote stability and/or translation efficiency may also be used in an RNA. A method for generating RNA for use in transfection can involve in vitro transcription (IVT) of a template with specially designed primers, followed by polyA addition, to produce a construct containing 3' and 5' untranslated sequence ("UTR"), a 5' cap and/or Internal Ribosome Entry Site (IRES), the nucleic acid to be expressed, and a polyA tail typically 50-2000 bases in length. RNA so produced can efficiently transfect different kinds of cells.

RNA can be introduced into target cells using any of a number of different methods, for instance, available methods which include, but are not limited to, electroporation or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns".

A vector can be introduced into a host cell, e.g., mammalian cell by any method known in the art, for example, by physical, chemical or biological means. Physical methods for introducing a polynucleotide into a host cell include calcium phosphate precipitation, lipofection, particle bombardment, microinjection, electroporation, and the like. Biological methods include the use of viral vectors, and especially retroviral vectors, for inserting genes into mammalian, e.g., human cells. Chemical means include colloidal dispersion systems, such as macromolecule complexes, nanocapsules, microspheres, beads, and lipid-based systems including oil-in-water emulsions, micelles, mixed micelles, and liposomes.

Method of Producing DC Tumor Vaccines

In another aspect, the disclosure provides a method of making a DC tumor vaccine as described herein. Numerous means of generating CAR-T cells known in the art can also be applied to generating DC tumor vaccines. Methods for generating CAR-T cells have been described in, for example, Zhang et al., Engineering CAR-T cells, Biomarker Research (2017) 5:22. In some embodiments, the method comprises introducing to a starting cell the vector comprising the first polynucleotide encoding the CAR and the second polynucleotide encoding the tumor antigen under conditions suitable for expression of the CAR and the tumor antigen. The method provided herein may comprise one of more steps selected from: obtaining a starting cell (i.e., a cell from a source), culturing (including expanding, optionally including maturating) the starting cell, and genetically modifying the cells. The starting cell can be a dendritic cell or a precursor or a progenitor cell thereof as described above.

Sources of Cells

The DC tumor vaccine provided herein may be obtained from any source. In certain embodiments, the DC tumor vaccine provided herein is derived from immune cells isolated from subjects, e.g., human subjects. In some embodiments, the immune cells are obtained from a subject of interest, such as a subject suspected of having a particular disease or condition, a subject suspected of having a predisposition to a particular disease or condition, a subject who will undergo, is undergoing, or have undergone treatment for a particular disease or condition, a subject who is a healthy volunteer or healthy donor, or from blood bank. In some embodiments, the immune cells are obtained from a cancer subject who has poor responsiveness to an immunotherapy, such as CAR-T therapy.

The cells can be autologous or allogeneic to the subject of interest. Allogeneic donor cells may not be human-leukocyte-antigen (HLA)-compatible, and thus allogeneic cells can be treated to reduce immunogenicity.

Immune cells can be collected from any location in which they reside in the subject including, but not limited to, blood, cord blood, spleen, thymus, lymph nodes, pleural effusion, spleen tissue, tumor and bone marrow. The isolated immune cells may be used directly, or they can be stored for a period of time, such as by freezing.

In some embodiments, the engineered cells are obtained by engineering a dendritic cell or a precursor or progenitor cell thereof. A dendritic cell or a precursor or progenitor cell thereof can be obtained from blood collected from a subject using any number of techniques known to the skilled artisan, such as apheresis. In some embodiments, the dendritic cell or a precursor or progenitor cell thereof is derived from peripheral blood cells (e.g., peripheral blood mononuclear cells, such as a monocyte), a bone marrow cell, an embryonic stem cell, or an induced pluripotent stem cell (iPSC).

The presence of a dendritic cell can be checked using the previously described method. For example, a dendritic cell may be identified by measuring expression of CD11c, CD80, CD86, MHC/HLA molecules, and/or CCR7 molecules, which can be detected using techniques, such as immune chemistry, immunophenotyping, flow cytometry, Elispots assays, classical tetramer staining, and intracellular cytokine staining.

Genetic Modification

Genetically modifying a DC or a precursor or progenitor cell thereof can be accomplished by transducing a population of substantially homogeneous DCs with a vector provided herein. In certain embodiments, a retroviral vector (e.g., a lentiviral vector) is employed for the introduction of the polynucleotides into the DCs. For example, the polynucleotide provided herein can be cloned into a lentiviral vector and expression can be driven from its endogenous promoter, from the lentiviral long terminal repeat, or from a promoter specific for a target cell type of interest. Common delivery methods for delivering viral vectors include but is not limited to, electroporation, microinjection, gene gun, and magnetofection. Placement of a presently disclosed CAR and tumor antigen can be made at any endogenous gene locus.

Non-viral approaches can also be employed for genetic modification of a DC or a precursor or progenitor cell thereof. For example, a nucleic acid molecule can be introduced into a DC or a precursor or progenitor cell thereof by administering the nucleic acid in the presence of lipofection (Ono et al., Neuroscience Letters 17:259, 1990; Feigner et al., Proc. Natl. Acad. Sci. U.S.A. 84:7413, 1987; Staubinger et al., Methods in Enzymology 101:512, 1983; Brigham et al., Am. J. Med. Sci. 298:278, 1989), sialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Other non-viral means for gene transfer include transfection in vitro using calcium phosphate, DEAE dextran, electroporation, and protoplast fusion. Liposomes can also be potentially beneficial for delivery of DNA into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue or are injected systemically. Recombinant receptors can also be derived or obtained using transposases or targeted nucleases (e.g. Zinc finger nucleases, meganucleases, or TALE nucleases, CRISPR).

In certain embodiment, the DC tumor vaccine provided herein are prepared by transfecting the vector comprising the polynucleotides encoding the CAR and tumor antigen provided herein into a DC prior to administration. In certain embodiments, the DC tumor vaccine provided herein can be made by transfecting a precursor or progenitor cell of DC with, for example, a viral vector, followed by differentiating the transfected cell into a DC. The DC tumor vaccine provided herein exhibit improved expression of CARs on the cell surface and tumor antigen. The precursor or progenitor cell of a DC can be derived from peripheral blood cells (e.g., peripheral blood mononuclear cells, such as a monocyte, e.g., THP-1 cell, peripheral monocytes), a bone marrow cell. The precursor or progenitor cell of a DC can also be an embryonic stem cell, or an induced pluripotent stem cell (iPSC).

In another aspect, the present disclosure also provides a population of cells produced ex vivo by the method as described above. In certain embodiments, at least 70%, at least 75%, at least 80%, at least 85%, at least 90% or at least 95% of the population of cells express a detectable level of the CAR polypeptide and tumor antigen provided herein. In certain embodiments, at least 85% of the population of cells express a detectable level of the CAR polypeptide and tumor antigen provided herein.

Pharmaceutical Composition

In another aspect, the present disclosure also provides a pharmaceutical composition comprising the population of the DC tumor vaccines provided herein and a pharmaceutically acceptable medium. As used herein, the term "pharmaceutical composition" refers to a composition formulated for pharmaceutical use.

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

A "pharmaceutically acceptable medium" refers to an ingredient in a pharmaceutical formulation, other than an active ingredient, which is biologically acceptable and non-toxic to a subject. Pharmaceutical acceptable medium for use in the pharmaceutical compositions disclosed herein may include, for example, pharmaceutically acceptable liquid, gel, or solid carriers, aqueous or nonaqueous vehicles, antimicrobial agents, buffers, antioxidants, isotonic agents, suspending/dispending agents, sequestering or chelating agents, diluents, adjuvants, excipients, or non-toxic auxiliary substances, or various combinations thereof.

The pharmaceutical compositions of the present disclosure can be prepared using various techniques known in the art, see, for example, Remington, The Science And Practice of Pharmacy (21st ed. 2005). Briefly, the DC tumor vaccine or a population thereof is admixed with a suitable medium prior to use or storage. Suitable pharmaceutically acceptable medium generally comprise inert substances that help in: 1) administering the pharmaceutical composition to a subject, 2) processing the pharmaceutical compositions into deliverable preparations, and/or 3) storing the pharmaceutical composition prior to administration. In certain embodiments, the pharmaceutically acceptable medium comprises agents that can stabilize, optimize or alter the form, consistency, viscosity, pH, pharmacokinetics, and/or solubility of the formulation. Such agents include, without limitation, buffering agents, wetting agents, emulsifying agents, diluents, encapsulating agents, and skin penetration enhancers, for example, saline, buffered saline, dextrose, arginine, sucrose, water, glycerol, ethanol, sorbitol, dextran, sodium carboxymethyl cellulose, and combinations thereof.

Exemplary pharmaceutically acceptable medium include sugars (e.g., lactose, glucose and sucrose), starches (e.g., corn starch and potato starch), cellulose and derivatives thereof (e.g., sodium carboxymethyl cellulose, methylcellulose, ethyl cellulose, microcrystalline cellulose and cellulose acetate), powdered tragacanth, malt, gelatin, lubricating agents (e.g., magnesium stearate, sodium lauryl sulfate and talc), excipients (e.g., cocoa butter and suppository waxes), oils (e.g., peanut oil, cottonseed oil, safflower oil, sesame oil, olive oil, corn oil and soybean oil, glycols (e.g., propylene glycol), polyols (e.g., glycerin, sorbitol, mannitol and polyethylene glycol (PEG)), esters (e.g., ethyl oleate and ethyl laurate), agar, buffering agents (e.g., magnesiums hydroxide and aluminum hydroxide), alginic acid, pyrogen-free water, isotonic saline, Ringer's solution, ethyl alcohol, pH buffered solutions, polyesters, polycarbonates, polyanhydrides, bulking agents (e.g., polypeptides and amino acids, serum alcohols (e.g., ethanol), (sterile) phosphate-buffered saline, Ringer's solution, dextrose solution and other non-toxic compatible substances used in pharmaceutical formulations.

The pharmaceutical compositions provided herein can be administered systemically or directly to a subject for inducing and/or enhancing an immune response to an antigen and/or treating and/or preventing a neoplasm, pathogen infection, or infectious disease. In certain embodiments, the pharmaceutical compositions provided herein are directly injected into a tumor or organ of interest. In other embodiments, the pharmaceutical compositions provided herein are administered indirectly to the organ of interest, for example, by administration into the circulatory system (e.g., the tumor vasculature).

The pharmaceutical compositions provided herein may comprise at least a population of about $1\times10^5$, about $2\times10^5$, about $3\times10^5$, about $4\times10^5$ or about $5\times10^5$ DC tumor vaccines (i.e., engineered cells). Those skilled in the art can readily determine the percentage of the DC tumor vaccines provided herein in a population using various well-known methods, for example, fluorescence activated cell sorting (FACS). Suitable ranges of the percentage of the DC tumor vaccines provided herein in a population (also referred as "purity") may be about 50% to about 55%, about 55% to about 60%, and about 65% to about 70%, about 70% to about 75%, about 75% to about 80%, about 80% to about 85%, about 85% to about 90%, about 90% to about 95%, or about 95% to about 100%.

In certain embodiment, the recipient is administered at least $1\times10^3$ cells/kg of bodyweight, at least $5\times10^3$ cells/kg of bodyweight, at least $1\times10^4$ cells/kg of bodyweight, at least $5\times10^4$ cells/kg of bodyweight, at least $1\times10^5$ cells/kg of bodyweight, at least $5\times10^5$ cells/kg of bodyweight, at least $1\times10^6$ cells/kg of bodyweight, at least $5\times10^6$ cells/kg of bodyweight, at least $1\times10^7$ cells/kg of bodyweight, at least $5\times10^7$ cells/kg of bodyweight, at least $1\times10^8$ cells/kg of bodyweight, at least $2\times10^8$ cells/kg of bodyweight, at least $3\times10^8$ cells/kg of bodyweight, at least $4\times10^8$ cells/kg of bodyweight, at least $5\times10^8$ cells/kg of bodyweight, or at least $6\times10^8$ cells/kg of bodyweight. A person skilled in the art would understand that dosage of the pharmaceutical compositions provided herein may be determined based on various factors of the recipient, such as size, age, sex, weight, and condition. Dosages can be readily determined by a person skilled in the art from this disclosure and the knowledge in the art. The person skilled in the art can readily determine the number of the DC tumor vaccine provided herein and the amount of optional additives, vehicles, medium and/or carriers in compositions and to be administered in methods of the present disclosure. Typically, additives, if any, are present in an amount of 0.001 to 50% (weight) solution in phosphate buffered saline, and the active ingredient (e.g., the modified/recombinant cells provided herein) is present in the order of micrograms to milligrams, such as about 0.0001 to about 5 wt %, preferably about 0.0001 to about 1 wt %, still more preferably about 0.0001 to about 0.05 wt % or about 0.001 to about 20 wt %, preferably about 0.01 to about 10 wt %, and still more preferably about 0.05 to about 5 wt %. It would be preferred to determine the toxicity of a certain dosage, such as by determining the lethal dose (LD) and LD50 in a suitable animal model (e.g., a mouse). It would also be preferred to determine the timing of administering the composition(s), which elicit a suitable response. Such determinations do not require undue experimentation from the knowledge of the person skilled in the art and the present disclosure.

The pharmaceutical compositions provided herein can be administered by, for example, injection (e.g., systemic injection, localized injection, intravenous injection, intralymphatic injection) or catheter. In certain embodiments, the pharmaceutical compositions provided herein can be administered subcutaneously, intradermally, intratumorally, intramedullary, or intraperitoneally. In one embodiment, the cell compositions of the present disclosure are preferably administered by intravenous injection. The administration can be autologous or heterologous. For example, the DC tumor vaccine can be obtained by modifying the starting cells from one subject and administered to the same subject or a different subject. The pharmaceutical compositions provided herein can be formulated in a unit dosage injectable form (e.g., solution, suspension, emulsion) for administration. The administration of the pharmaceutical compositions provided herein can occur as a single event or over a time course of treatment, such as daily, weekly, bi-weekly, or monthly. The pharmaceutical compositions provided herein can be administered in combination with (e.g., before, after, or simultaneously with) another agent, such as a chemotherapeutic agent, another form of immune therapy (e.g., CAR-T therapy), or radiation therapy. Simultaneous administration can occur through the administration of separate compositions, each containing the DC tumor vaccine provided herein and another agent, such as a chemotherapeutic agent, another form of immune therapy (e.g., CAR-T therapy), or radiation therapy. Simultaneous administration can occur through the administration of one composition containing the DC tumor vaccine provided herein and another agent, such as a chemotherapeutic agent, another form of immune therapy (e.g., CAR-T therapy), or radiation therapy.

Method of Uses

The present disclosure also provides various uses of the DC tumor vaccines provided herein.

General Uses

In one aspect, the present disclosure provides a method for treating cancer in a patient comprising administering a therapeutically effective amount of the DC tumor vaccine provided herein to the patient. In some embodiments, the method for treating a disease or pathological condition comprises providing DCs isolated from or derived from the cells (e.g., a peripheral blood cell, a bone marrow cell, an embryonic stem cell) isolated from a subject or derived from an iPSC, engineering the DCs to express the CAR and tumor antigen as provided herein to generate a DC tumor vaccine, and transfuse the DC tumor vaccine back into the subject. In some embodiments, the method for treating cancer comprises providing a precursor or progenitor cell of a DC (e.g., a peripheral blood cell, a bone marrow cell, an embryonic stem cell, or an iPSC), engineering the precursor or progenitor cell to express the CAR and tumor antigen as provided herein, differentiating the engineered precursor or progenitor cell into a DC expressing the CAR and tumor antigen as provided herein, and transfuse the DC expressing CAR and tumor antigen as provided herein (e.g., DC tumor vaccine) back into the subject.

In some embodiments, the cancer is a solid cancer selected from the group consisting of adrenal cancer, bone cancer, brain cancer, breast cancer, colorectal cancer, esophageal cancer, eye cancer, gastric cancer, head and neck cancer, kidney cancer, liver cancer, lung cancer, non-small cell lung cancer, bronchioloalveolar cell lung cancer, mesothelioma, head and neck cancer, squamous cell carcinoma, melanoma, oral cancer, ovarian cancer, cervical cancer, penile cancer, prostate cancer, pancreatic cancer, skin cancer, sarcoma, testicular cancer, thyroid cancer, uterine cancer, vaginal cancer. In some embodiments, the cancer is a hematologic malignancy selected from the group consisting of diffuse large B-cell lymphoma (DLBCL), extranodal NK/T-cell lymphoma, HHV8-associated primary effusion lymphoma, plasmablastic lymphoma, primary CNS lymphoma, primary mediastinal large B-cell lymphoma, T-cell/histiocyte-rich B-cell lymphoma, Hodgkin's lymphoma, non-Hodgkin's lymphoma, Waldenstrom's macroglobulinemia, multiple myeloma (MM).

In some embodiments, the subject having cancer is poorly responsive to a cancer therapy (e.g., immunotherapy).

The term "immunotherapy" as used herein, refers to a type of therapy that stimulates immune system to fight against disease such as cancer or that boosts immune system in a general way. Immunotherapy includes passive immunotherapy by delivering agents with established tumor-immune reactivity (such as effector cells) that can directly or indirectly mediate anti-tumor effects and does not necessarily depend on an intact host immune system (such as an antibody therapy or CAR-T cell therapy). Immunotherapy can further include active immunotherapy, in which treatment relies on the in vivo stimulation of the endogenous host immune system to react against diseased cells with the administration of immune response-modifying agents.

Examples of immunotherapy include, without limitation, checkpoint modulators, adoptive cell transfer, cytokines, oncolytic virus and therapeutic vaccines.

Checkpoint modulators can interfere with the ability of cancer cells to avoid immune system attack, and help the immune system respond more strongly to a tumor. Immune checkpoint molecule can mediate co-stimulatory signal to augment immune response or can mediate co-inhibitory signals to suppress immune response. Examples of checkpoint modulators include, without limitation, modulators of PD-1, PD-L1, PD-L2, CTLA-4, TIM-3, LAG3, A2AR, CD160, 2B4, TGF R, VISTA, BTLA, TIGIT, LAIR1, OX40, CD2, CD27, CD28, CD30, CD40, CD47, CD122, ICAM-1, IDO, NKG2C, SLAMF7, SIGLEC7, NKp80, CD160, B7-H3, LFA-1, 1COS, 4-1BB, GITR, BAFFR, HVEM, CD7, LIGHT, IL-2, IL-7, IL-15, IL-21, CD3, CD16 and CD83. In certain embodiments, the immune checkpoint modulator comprises a PD-1/PD-L1 axis inhibitor.

Adoptive cell transfer, which is a treatment that attempts to boost the natural ability of the T cells to fight cancer. In this treatment, T cells are taken from the patient, and are expanded and activated in vitro. In certain embodiments, the T cells are modified in vitro to CAR-T cells. T cells or CAR-T cells that are most active against the cancer are cultured in large batches in vitro for 2 to 8 weeks. During this period, the patients will receive treatments such as chemotherapy and radiation therapy to reduce the body's immunity. After these treatments, the in vitro cultured T cells or CAR-T cells will be given back to the patient. In certain embodiments, the immunotherapy is CAR-T therapy.

Disruption of TIME

In one aspect, the present disclosure provides a method of disrupting TIME (for example, converting TIME into an inflammatory state) using the DC tumor vaccine provided herein.

In another aspect, the present disclosure also provides a method of inducing proliferation of immune cells, prolonging the survival of immune cells, and/or increasing expression and/or secretion of immune stimulating cytokines from immune cells in an immune suppressive microenvironment. The immune stimulating cytokines can be one or more of TNF-a, IFN-β, IFN-γ, IL-1, IL-2, IL-4, IL-6, IL-8, IL-10, IL-12, IL-18 and granulocyte-macrophage colony stimulating factor. The method comprises contacting the immune suppressive microenvironment with the DC tumor vaccine provided herein. The immune cell can be a T cell, a Natural Killer (NK) cell, a NKT cell, a B cell, a macrophage cell, an eosinophil or a neutrophil. In certain embodiments, the immune cell is a T cell, selected from the group consisting of CD4+ T cell, CD8+ T cell, cytotoxic T cell, terminal effector T cell, memory T cell, naïve T cell, natural killer T cell, gamma-delta T cell, cytokine-induced killer (CTK) T cell, and tumor infiltrating lymphocyte. In certain embodiments, the immune cell is an unmodified immune cell. In certain embodiments, the immune cell is a modified immune cell. The unmodified or modified immune cell can be autologous or allogeneic. In certain embodiments, the modified immune cell is a CAR-T cell. In certain embodiments, the CAR-T cell is derived from the same source (e.g., peripheral blood of a subject) as the DC tumor vaccine provided herein.

In certain embodiments, the immune suppressive microenvironment is an immune suppressive tumor microenvironment. The immune suppressive tumor microenvironment has been described supra. In certain embodiments, the immune suppressive tumor microenvironment comprises a tumor and/or a tumor infiltrating immune cell expressing an immune inhibitory molecule, for example, selected from the group consisting of PD-1, TIM3, TIGIT, LAG3, A2AR, BTLA (CD272), CTLA-4 (CD152), IDO1, IDO2, TDO, NOX2, VISTA, SIGLEC7 (CD328), PVR (CD155) and SIGLEC9 (CD329), PD-L1, PD-L2, B7-H3 (CD276), B7-H4 (VTCN1), PVR(CD155), sialoglycoprotein, CD112, CD113, Galectin9, CD24, and CD47. In certain embodiments, the immune inhibitory molecule is CTLA-4 and/or PD-L1. In certain embodiments, the tumor comprises a cell expressing CTLA4-Ig and/or PD-L1.

Combination Therapy

In another aspect, the present disclosure provides a combination therapy using the DC tumor vaccine provided herein and a second agent.

In certain embodiments, the second agent is a population of modified immune cells as described above, such as CAR-T cells. In certain embodiments, the CAR-T cell is derived from the same source (e.g., peripheral blood of a subject) as the DC tumor vaccine provided herein. In certain embodiments, the ratio of DC tumor vaccine and CAR-T cells provided in the combination therapy is in a range of about 1:1 to 1:10.

In certain embodiments, the DC tumor vaccine provided herein and the CAR-T cells are in the same pharmaceutical composition. In certain embodiments, the DC tumor vaccine provided herein and the CAR-T cells are in two separate pharmaceutical compositions. In certain embodiments, the DC tumor vaccine provided herein are administered to a subject in need thereof before, simultaneously or after administration of CAR-T cells.

In certain embodiments, the second agent is an agent that inhibits immunosuppressive pathways, including but not limited to, inhibitors of TGF-□, interleukin 10 (IL-10), adenosine, VEGF, indoleamine 2,3 dioxygenase 1 (IDO1), indoleamine 2,3-dioxygenase 2 (IDO2), tryptophan 2-3-dioxygenase (TDO), lactate, hypoxia, arginase, and prostaglandin E2. The second agent can also be a T-cell checkpoint inhibitor, including but not limited to, anti-CTLA4 antibody (e.g., Ipilimumab) anti-PD1 antibody (e.g., Nivolumab, Pembrolizumab, Cemiplimab), anti-PD-L1 antibody (e.g., Atezolizumab, Avelumab, Durvalumab), anti-PD-L2 antibody, anti-BTLA antibody, anti-LAG3 antibody, anti-TIM3 antibody, anti-VISTA antibody, anti-TIGIT antibody, and anti-KIR antibody.

In certain embodiments, the second agent is a T cell agonist, including but not limited to, antibodies that stimulate CD28, ICOS, OX-40, CD27, 4-1BB, CD137, GITR, and HVEM. In certain embodiment, the second agent is a therapeutic oncolytic virus, including but not limited to, rhabdoviruses, retroviruses, paramyxoviruses, picornaviruses, reoviruses, parvoviruses, adenoviruses, herpesviruses, and poxviruses.

In certain embodiments, the second agent is an immunostimulatory agent, such as toll-like receptors agonists, including but not limited to, TLR3, TLR4, TLR7 and TLR9 agonists. In certain embodiments, the second agent is a stimulator of interferon gene (STING) agonists, such as cyclic GMP-AMP synthase (cGAS).

In certain embodiments, the DC tumor vaccine provided herein are administered to a subject in need thereof in conjunction with, e.g., before, simultaneously or following, any number of relevant treatment modalities, including but not limited to, treatment with cytokines, or expression of cytokines from within the DC tumor vaccine, that enhance dendritic cell or T-cell proliferation and persistence and, include but not limited to, Flt3L, IL-2, IL-7, and IL-15 or analogues thereof.

In some embodiments, the treatment method further comprises administering an agent that reduces of ameliorates a side effect associated with the administration of the DC tumor vaccine. Exemplary side effects include cytokine release syndrome (CRS), and hemophagocytic lymphohistiocytosis (HLH, also termed macrophage activation syndrome (MAS)). In certain embodiments, the agent administered to treat the side effects comprises an agent that neutralizes soluble factors such as IFN-gamma, IFN-alpha, IL-2 and IL-6. Exemplary agents include, without limitation, an inhibitor of TNF-alpha (e.g., entanercept) and an inhibitor of IL-6 (e.g., tocilizumab).

EXAMPLES

While the disclosure has been particularly shown and described with reference to specific embodiments (some of which are preferred embodiments), it should be understood by those having skill in the art that various changes in form

Example 1

This example illustrates the construction of a lentiviral vector expressing both CAR and a tumor gene mutant peptide and the expression of the vector in 293FT cells:

Construction of Lentiviral Vector

All sequences are optimized and synthesized by GUANGZHOU IGE BIOTECHNOLOGY. The CAR gene (SEQ ID NO: 28) and p53 R273H vaccine gene (SEQ ID NO:33), CAR-DC vaccine combo gene (SEQ ID NO:38), KRAS G12C vaccine gene (SEQ ID NO:34) or KRAS G12V vaccine gene (SEQ ID NO:35) were cloned into lenti-Cas9 (Addgene) vector to replace Cas9. The structure diagram of the vector is shown in FIG. 1A.

Preparation of Lentivirus

All plasmid DNA used for packaging lentiviruses are extracted and purified using NucleoBond Xtra Midi EF kit (Takara Bio). The lentivirus was produced according to the commonly used methods described on the Addgene website and packaged using polyethylenimine (PEI) (Sigma Aldrich). The day before packaging the virus, 293FT cells (ATCC) were passaged at a ratio of 1:3 and split into 15 cm petri dishes. The next day when the cell confluence reached 90%, the virus was packaged. The medium was changed to fresh medium 1 h before transfection. The two packaging plasmids pSPAX2 (Addgene, Cat. No. 12260) and pMD2.G (Addgene Cat. No. 12259), the target lentiviral vector and 1 mg/ml PEI were diluted in Opti-MEM (purchased from Gibco) at the ratio of DNA:PEI of 1:3~1:4. After incubating for 20 minutes at room temperature, the plasmid mixture was gently dropped into the cell culture medium, and the medium was replaced with DMEM complete medium (Gibco) 8 hours after transfection. The lentiviral particles were collected at 48~72 h after transfection. The supernatant of the culture medium containing the virus was concentrated using Lenti-X virus concentrate (Takara Bio). The collected media containing virus particles was centrifuged at 1500 g for 15 minutes, 1/3 volume of Lenti-X virus concentrate was added to the separated supernatant, mixed well and then standed overnight at 4° C. The next day, the mixture was centrifuged at 4° C., 3000 rpm for 45 min. The virus particles at the bottom of the centrifuge tube were resuspended in 0.6~0.8 ml of pre-cooled PBS buffer and stored in aliquots in a refrigerator at −80° C. for subsequent use.

Figure 1B:
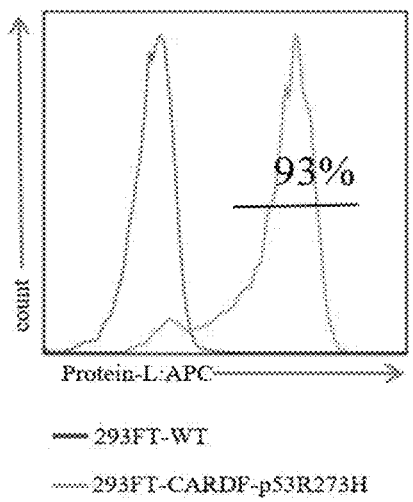

The results of the 293FT cells infected with the lentivirus is shown in FIG. 1B. As shown in FIG. 1B, after the lentivirus infection, 93% of the 293FT cells expressed CAR on the cell surface as detected by protein-L, indicating that the constructed lentiviral vector expressing both CAR and tumor gene mutant peptides can effectively transduce cells and express CAR structure on the cell surface after being packaged into lentivirus.

As shown in FIG. 1C and FIG. 1D, H460 has the wild-type p53 gene, while the SW480 cells has a mutated p53 gene that contains a G>A mutation, resulting a R273H mutation in the p53 protein. Therefore, SW480 is a tumor cell line containing a p53R273H mutation.

As shown in FIG. 1E and FIG. 1F, the nucleotide encoding the 12th amino acid residue of KRAS in SW837 cells has a mutation GGT>TGT, which makes the encoded amino acid mutated to G12C. The nucleotide encoding the 12th amino acid residue of KRAS in SW480 cells has a mutation GGT>GTT, which makes the encoded amino acid mutated to G12V. Therefore, SW480 is a tumor cell line with KRAS G12V mutation, and SW837 is a tumor cell line with KRAS G12C mutation.

Figure 1G:
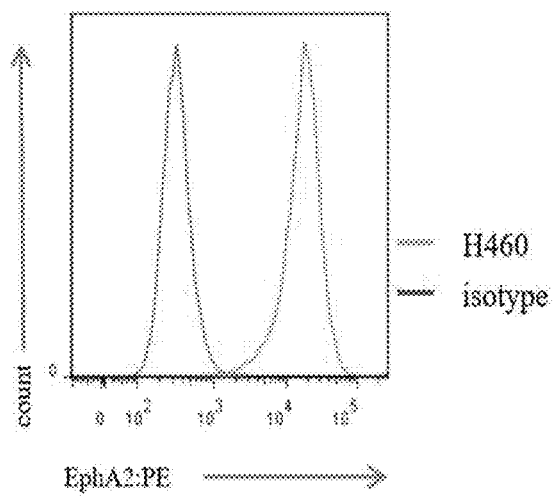
Figure 1H:
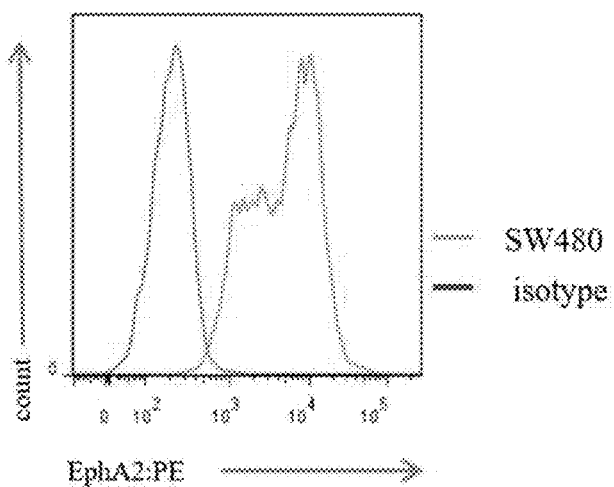
Figure 1I:
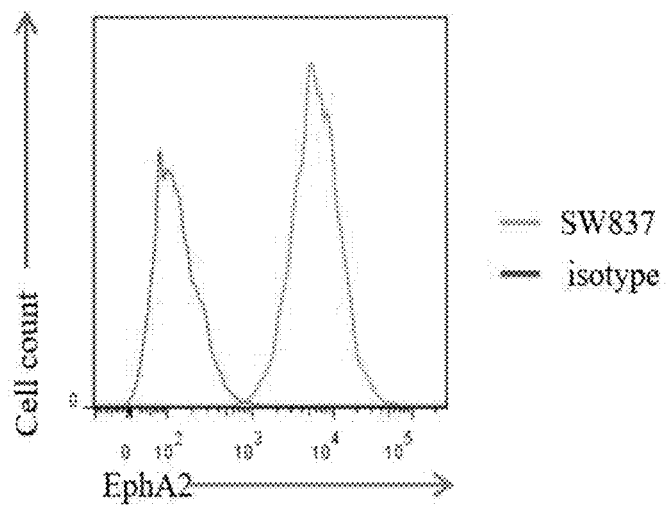

As shown in FIG. 1G-1I, H460, SW480 and SW837 cells express high level of EphA2 on the cell surface.

Figure 1J:
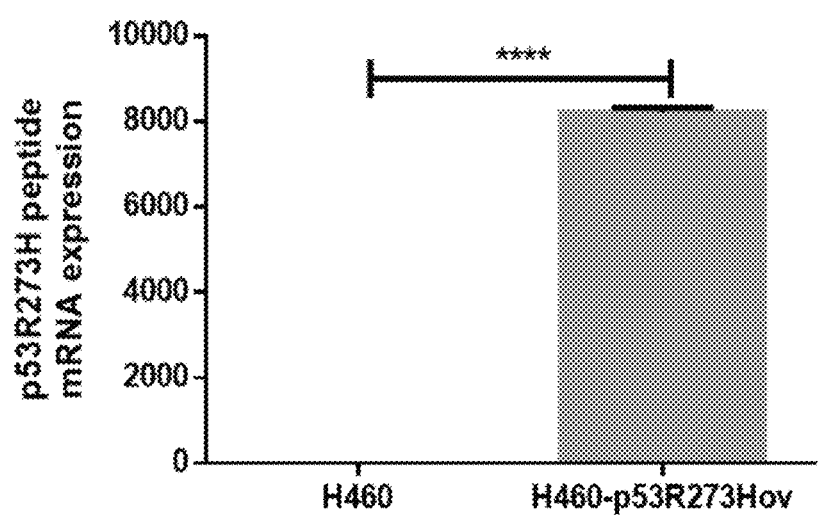

As shown in FIG. 1J, the constructed H460-p53R273Hov cell expressed the p53R273H mutant polypeptide at a high level.

Example 2

This example illustrates the preparation of DCs from humanized mouse bone marrow cells.

The femur and tibia of a humanized mouse were taken out using sterile scissors, soaked in 70% alcohol for 3 minutes, and rinsed twice with ice-cold PBS. The PBS was then aspirated with a sterile syringe (26-gauge needle). The bone marrow cells were flushed out by rinsing from one end of the bone marrow cavity. The bone marrow cells were dispersed by repeated blow and suck using a 1 ml pipette tip and then filtered through a 70 m nylon mesh. The filtered cells were collected and centrifuged. The red blood cells were then dissolved with lysis buffer (BD Biosciences). The remaining cells were washed twice with PBS and counted. The cells were cultured at 1×106/ml in differentiation medium (RPMI-1640 complete medium with 20 ng/ml recombinant human GM-CSF and 5 ng/ml recombinant human IL-4), supplemented with fresh differentiation medium every two days.

On the 8th day of differentiation, immature DCs were infected with lentivirus with an MOI of 100. The concentrated lentiviral stock solution with appropriate titer was slowly thawed at 37° C. An appropriate amount of virus stock solution was mixed with 6 ug/ml protamine sulfate and added into the differentiation medium. After incubating for 12 hours at 37° C., 1 ml of differentiation medium was added to each well. After 24 hours of transduction, the cells were collected for centrifugation, the virus-containing medium was carefully discarded, the cells were washed twice with PBS, and further cultured in fresh differentiation medium until use on the 10th day.

Figure 2A:
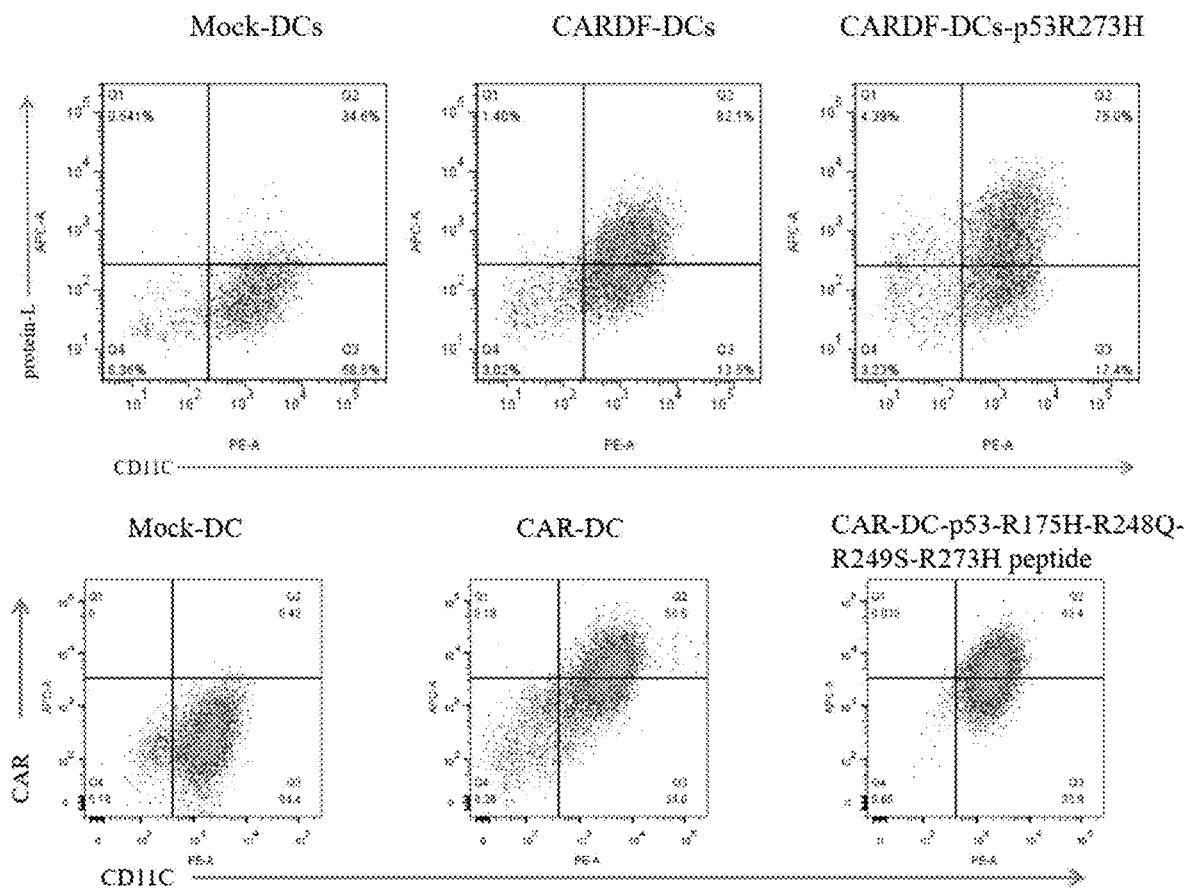
FIGS. 2A-2D show the human DCs differentiated from the humanized mouse bone marrow cells and the expression of CARDF-p53R273H in the DCs after transduction.

As shown in FIG. 2A and Tables 1 and 1A below, Hu-mice bone marrow cells can be induced into human DCs with an efficiency of over 90%. After transduction, the efficiency of CARDF expression on the surface of CARDF-DC and p53R273H vaccine is 82.1% and 75%, respectively. For the CARDC vaccine combo experiment, the efficiency of CARDF expression of the surface of CARDF-DC and CARDC vaccine combo is 56.5% and 63.4% respectively.

TABLE 1

| The efficiency of differentiation into DC | | |
|---|---|---|
| Mock-DCs | CARDF-DCs | p53R273H vaccine |
| 34.6 + 58.5 = 93.1 | 82.1 + 13.5 = 95.6 | 75 + 17.4 = 92.4 |

TABLE 1A

| The efficiency of differentiation into DC | | |
|---|---|---|
| Mock-DCs | CARDF-DCs | CARDC vaccine combo |
| 0.42 + 94.4 = 94.82 | 56.5 + 34 = 90.5 | 63.4 + 35.9 = 99.3 |

Figure 2B:
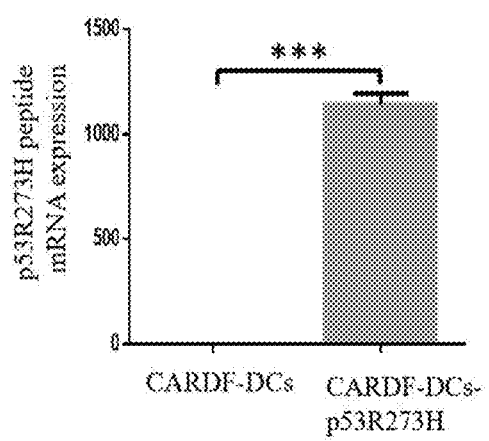

As shown in FIG. 2B, the qPCR analysis of the CARDF-DC and p53R273H vaccine showed that the mRNA expression level of p53R273H in the p53R273H vaccine was significantly increased.

Figure 2C:
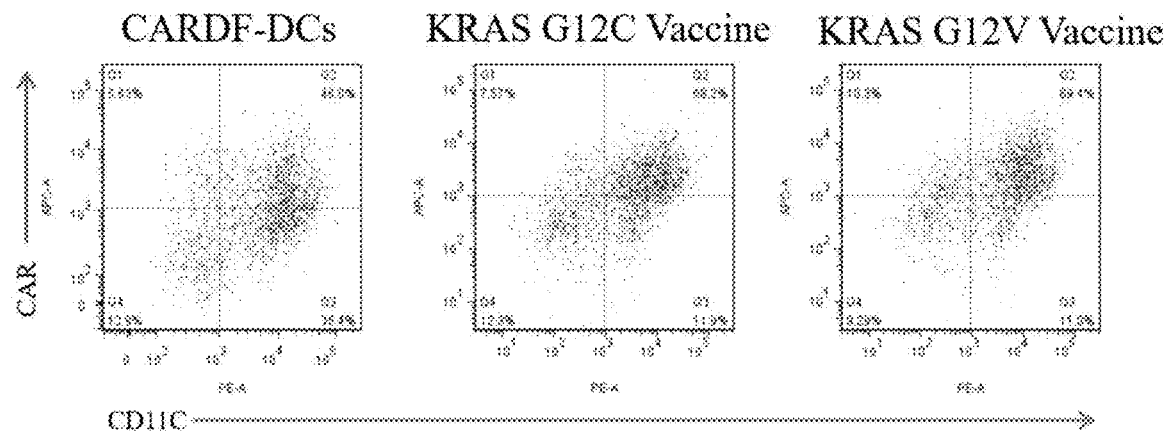

As shown in FIG. 2C and Table 2 below, Hu-mice bone marrow cells can be induced into human DCs with an efficiency of over 80%. After transduction, the efficiency of CARDF expression on the surface of CARDF-DC, KRAS G12C vaccine and KRAS G12V vaccine is 46%, 68.2% and 69.4%, respectively.

TABLE 2

The efficiency of differentiation into DC

| CARDF-DCs | KRAS G12C vaccine | KRAS G12V vaccine |
| --- | --- | --- |
| 46 + 35.4 = 81.4 | 68.2 + 11.9 = 80.1 | 69.4 + 10.9 = 80.3 |

Figure 2D:
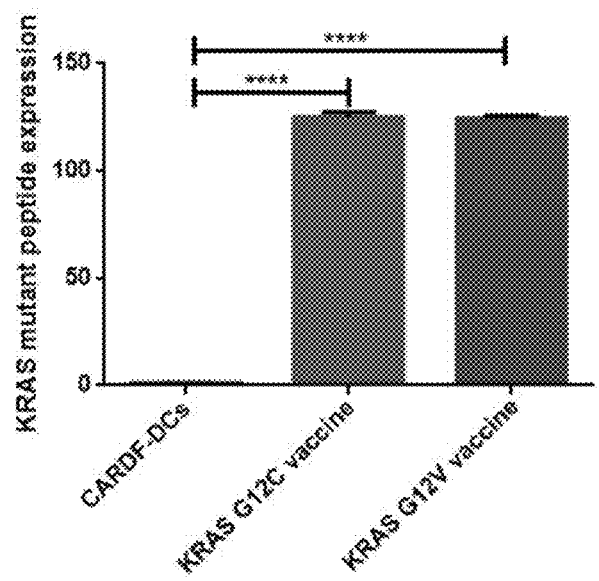

As shown in FIG. 2D, the qPCR analysis of the CARDF-DC, KRAS G12C vaccine and KRAS G12V vaccine showed that the mRNA expression level of the mutated peptide in the KRAS G12C vaccine and KRAS G12V vaccine was significantly increased.

The above data shows that humanized mouse bone marrow cells can effectively differentiate into human DCs, CARDF can be expressed at a high level on the surface of DCs through lentiviral transduction, and p53R273H can also be expressed at a high level in DC cells.

Example 3

This example illustrates the use of the DC tumor vaccine derived from humanized mouse bone marrow cells in treating the tumors in a Hu-mice xenograft model.

Figure 3A:
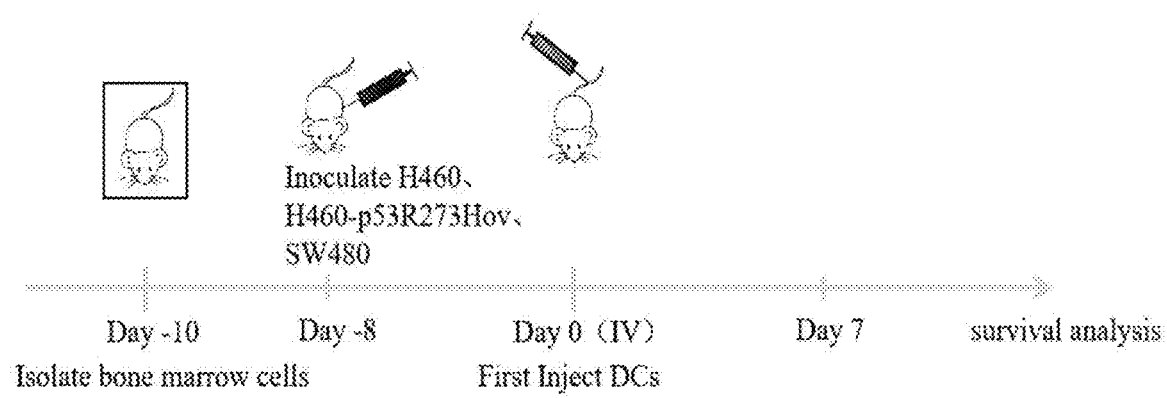
FIG. 3A-3G show the tumor growth in a humanized mouse (Hu-mice) tumor model after being treated with the dendritic cell tumor vaccine (hereinafter referred to as CARDF-DC vaccine).

2×106 H460 cells, 2×106 H460-p53R273Hov cells, and 2×106 SW480 cells were resuspended with 100 μL PBS, and subcutaneously injected into both sides of Hu-mice's back to prepare the xenograft Hu-mice tumor models. The tumor-bearing Hu-mice was randomly divided into three groups, namely: (1) Mock-DCs treatment group, (2) CARDF-DCs treatment group, (3) p53R273H vaccine treatment group The treatment process is shown in FIG. 3A. 2×106 SW480 cells and 2×106 SW837 cells were resuspended in 100 μL PBS and injected subcutaneously into the back of Hu-mice to prepare a xenograft Hu-mice animal tumor model. The tumor-bearing Hu-mice was randomly divided into three groups, namely: (1) CARDF-DCs treatment group, (2) KRAS G12C vaccine treatment group, (3) KRAS G12V vaccine treatment group.

Figure 3B:
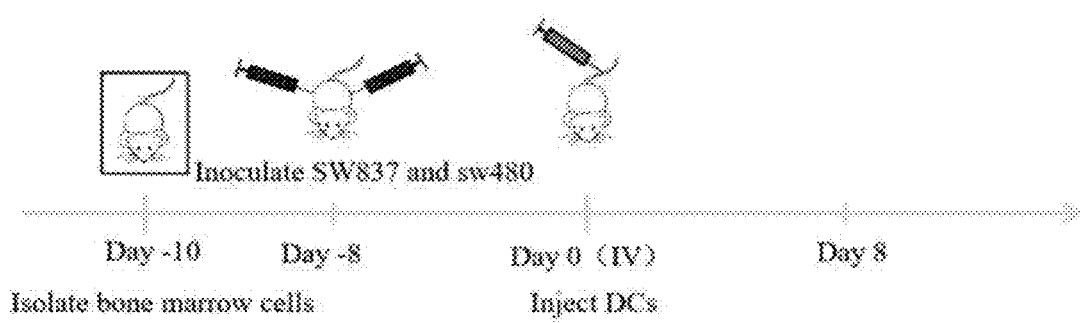

The treatment process is shown in FIG. 3B. The cell therapy was injected into mice through the tail vein, and the cells were resuspended in 400 μL PBS. The dose of the first injection in FIG. 3A during the treatment was 6×106 DCs/mouse, and the dose of the second injection was 2×106 DCs/mouse. The injection dose during the treatment of FIG. 3B is 5×106 DCs/mouse. During the cell therapy, the size of the tumor was measured with a vernier caliper every other day and statistics were made. When the mice were euthanized, all tumors were collected, weighed and photographed. In addition, mouse spleen, blood and bone marrow were collected, separated and processed into single cells, stained with fluorescent-labeled flow cytometry antibody, and analyzed by flow cytometry. RNA extracted from tumor tissue was analyzed by qPCR. The results are shown in FIG. 3-FIG. 5. Primers sequences are shown in FIG. 5E.

Figure 3C:
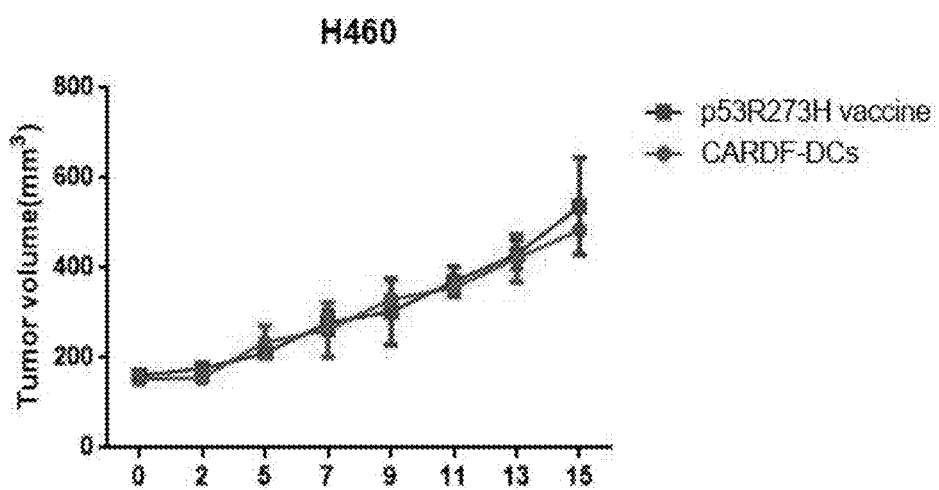

As shown in FIG. 3C, the tumor tissue formed by H460 had no significant difference in tumor tissue growth after different treatments. This suggests that CAR-DC alone does not have anti-tumor activity and that CAR-DC vaccine does not work on tumors in absence of the antigen loaded onto the CAR-DC vaccine.

Figure 3D:
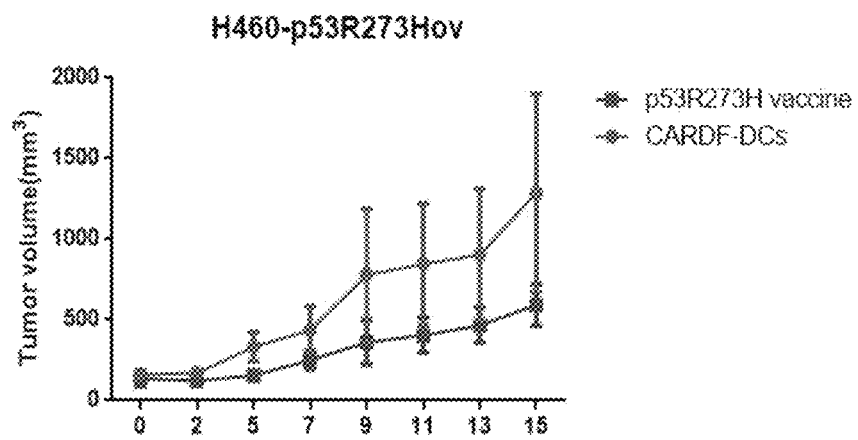

As shown in FIG. 3D and Table 3, the growth of tumor tissue formed by H460-p53R273Hov was inhibited after being treated with p53R273H vaccine. On day 15, the average tumor volume of H460-p53R273Hov tumor tissue in the CARDF-DCs treatment group was 1286.64 mm3, and the average tumor volume in the p53R273H vaccine treatment group was 591.789 mm3.

TABLE 3

Average volume of H460-p53R273Hov tumor tissue in each group on day 15 (mm3). This suggests that the CAR-DC vaccine provided herein has significantly improved anti-tumor activity on tumors having corresponding mutations.

| CARDF-DCs | p53R273H vaccine |
| --- | --- |
| 1286.64 | 591.789 |

Figure 3E:
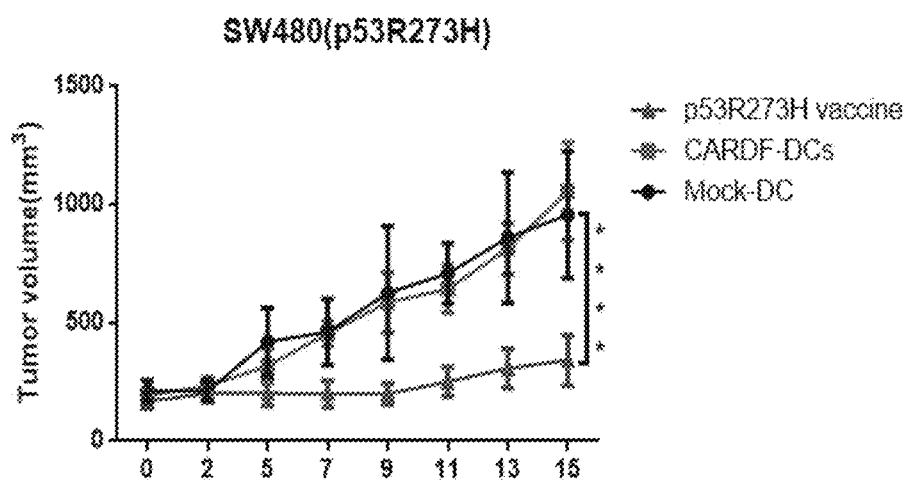

As shown in FIG. 3E and Table 4, the growth of tumor tissue formed by SW480 was inhibited after being treated with p53R273H vaccine. On day 15, the average tumor volume of SW480 tumor tissue in the CARDF-DCs treatment group was 1055.52 mm3, and the average tumor volume in the p53R273H vaccine treatment group was 342.587 mm3.

TABLE 4

Average volume of SW480 tumor tissue in each group on day 15 (mm3)

| Mock-DCs | CARDF-DCs | p53R273H vaccine |
| --- | --- | --- |
| 957.522 | 1055.52 | 342.587 |

Figure 3F:
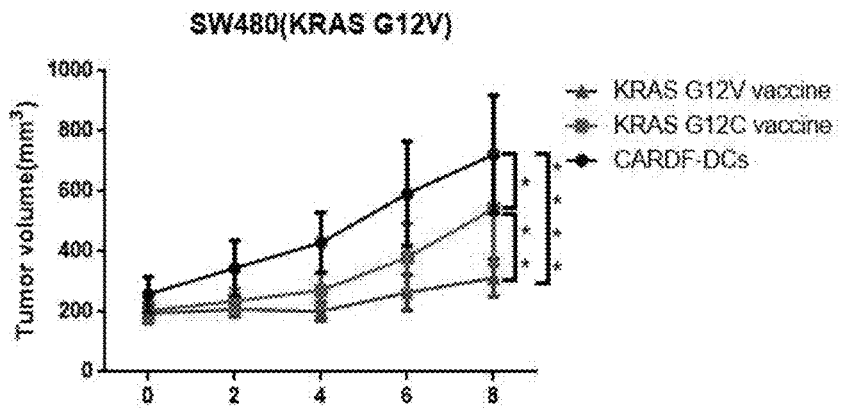

As shown in FIG. 3F and Table 5, the growth of tumor tissue formed by SW480 was inhibited after being treated with KRAS G12V vaccine. On day 15, the average tumor volume of SW480 tumor tissue in the CARDF-DCs treatment group was 723.254 mm3, the average tumor volume of SW480 tumor tissue in the KRAS G12C treatment group was 542.616 mm3, and the average tumor volume in the KRAS G12V vaccine treatment group was 312.747 mm3.

TABLE 5

Average volume of SW480 tumor tissue in each group on day 15 (mm3)

| CARDF-DCs | KRAS G12C vaccine | KRAS G12V vaccine |
| --- | --- | --- |
| 723.254 | 542.616 | 312.747 |

Figure 3G:
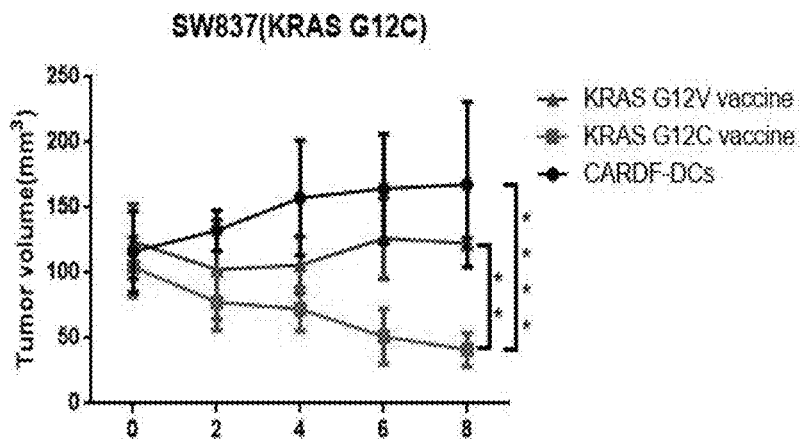

As shown in FIG. 3G and Table 6, the growth of tumor tissue formed by SW837 was inhibited after being treated with KRAS G12C vaccine. On day 8, the average tumor volume of SW837 tumor tissue in the CARDF-DCs treatment group was 167.727 mm3, the average tumor volume of SW837 tumor tissue in the KRAS G12C treatment group was 41.3374 mm3, and the average tumor volume in the KRAS G12V vaccine treatment group was 122.71 mm3.

TABLE 6

Average volume of SW837 tumor tissue in each group on day 8 (mm3)

| CARDF-DCs | KRAS G12C vaccine | KRAS G12V vaccine |
|---|---|---|
| 167.727 | 41.3374 | 122.71 |

Figure 4A:
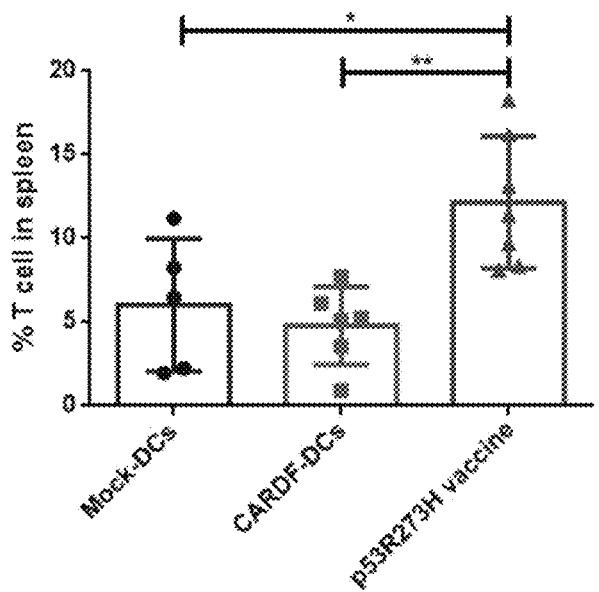
FIG. 4A-4H shows the flow cytometry analysis results in a humanized mouse (Hu-mice) tumor model after being treated with the dendritic cell tumor vaccine.

As shown in FIG. 4A and Table 7, the proportion of T cells in the p53R273H vaccine treatment group (12.163%) was higher than the CARDF-DCs treatment group (4.786%) and the Mock-DCs treatment group (6.024%), indicating that the DC vaccine stimulated the proliferation of T cells in the body.

TABLE 7

Average percentage of T cells in each group (%)

| Mock-DCs | CARDF-DCs | p53R273H vaccine |
|---|---|---|
| 6.024 | 4.786 | 12.163 |

Figure 4B:
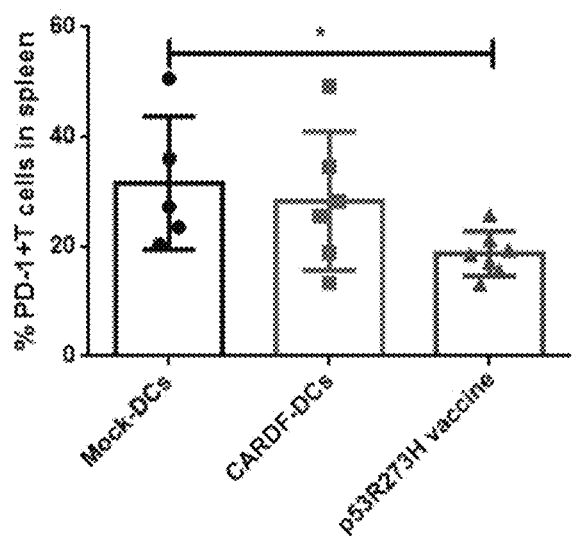

As shown in FIG. 4B and Table 8, the proportion of PD-1+ T cells in the p53R273H vaccine treatment group (18.7%) was lower than that in the Mock-DCs treatment group (31.6%), indicating that the DC vaccine reversed the depletion of T cells in the tumor microenvironment state.

TABLE 8

Average percentage of PD-1+ T cells in each group (%)

| Mock-DCs | CARDF-DCs | p53R273H vaccine |
|---|---|---|
| 31.6 | 28.3 | 18.7 |

Figure 4C:
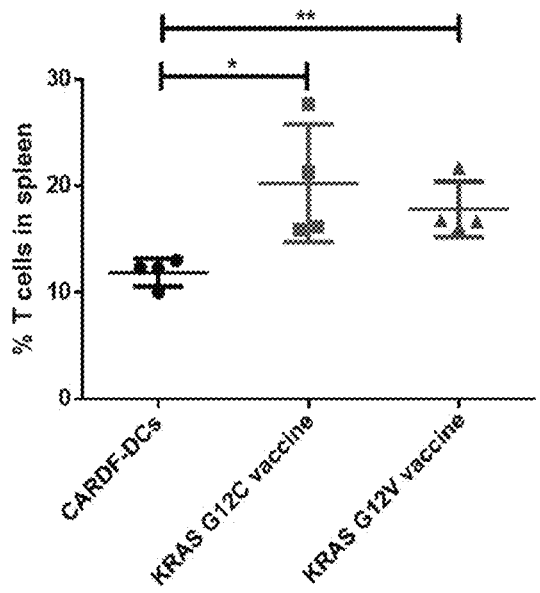

As shown in FIG. 4C and Table 9, the proportion of T cells in the KRAS G12C vaccine treatment group (27.3%) and the proportion of T cells in the KRAS G12V vaccine treatment group (17.825%) were higher than the CARDF-DCs treatment group (12.3%), indicating that the DC vaccine stimulated the proliferation of T cells in the body.

TABLE 9

Average percentage of T cells in each group (%)

| CARDF-DCs | KRAS G12C vaccine | KRAS G12V vaccine |
|---|---|---|
| 12.3 | 27.3 | 17.825 |

Figure 4D:
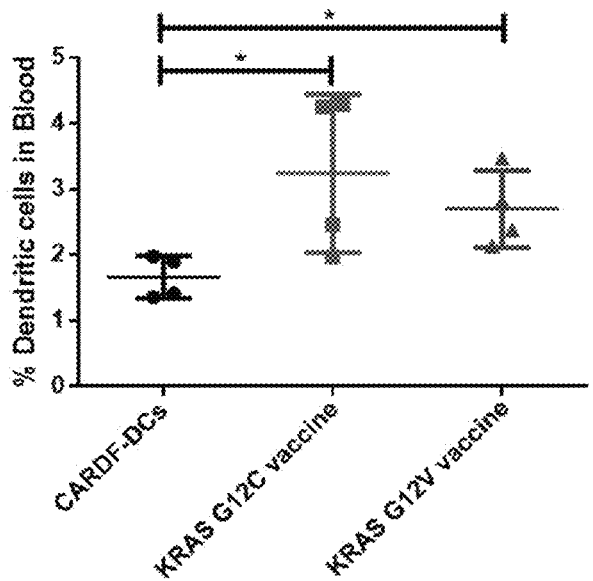

As shown in FIG. 4D and Table 10, the proportion of DC cells in the KRAS G12C vaccine treatment group (3.2425%) and the proportion of DC cells in the KRAS G12V vaccine treatment group (2.7%) increased compared to the CARDF-DCs treatment group (1.665%), indicating that the survival time of the DC vaccine in the body was prolonged.

TABLE 10

Average percentage of DC cells in each group (%)

| CARDF-DCs | KRAS G12C vaccine | KRAS G12V vaccine |
|---|---|---|
| 1.665 | 3.2425 | 2.7 |

Figure 4E:
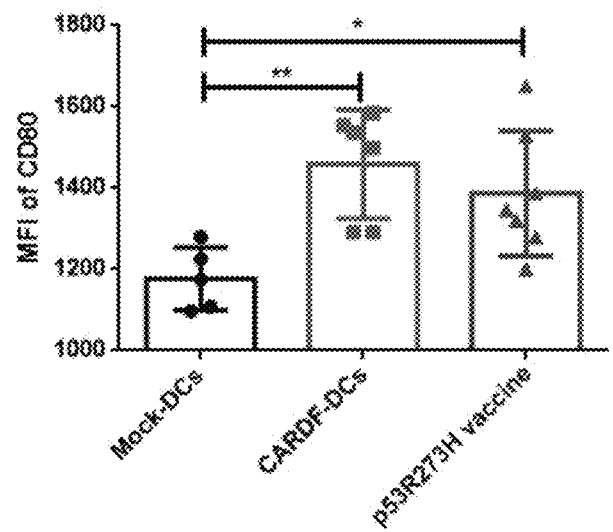

As shown in FIG. 4E and Table 11, the average fluorescence intensity of CD80 expression in DC cells of the CARDF-DCs treatment group and the p53R273H vaccine treatment group was significantly increased compared with the Mock-DCs treatment group, which indicates that the presence of CARDF renders the DCs being effectively activated after contacting the tumor target.

TABLE 11

Average fluorescence intensity of CD80 expression in DCs in each group

| Mock-DCs | CARDF-DCs | p53R273H vaccine |
|---|---|---|
| 1177 | 1459 | 1387 |

Figure 4F:
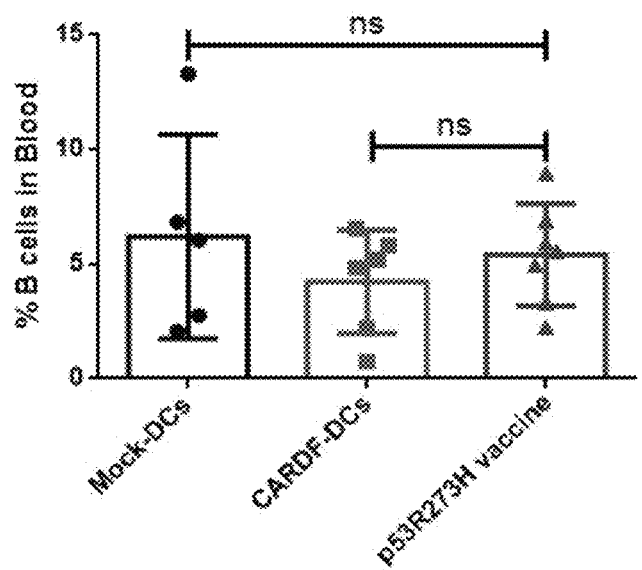
Figure 4G:
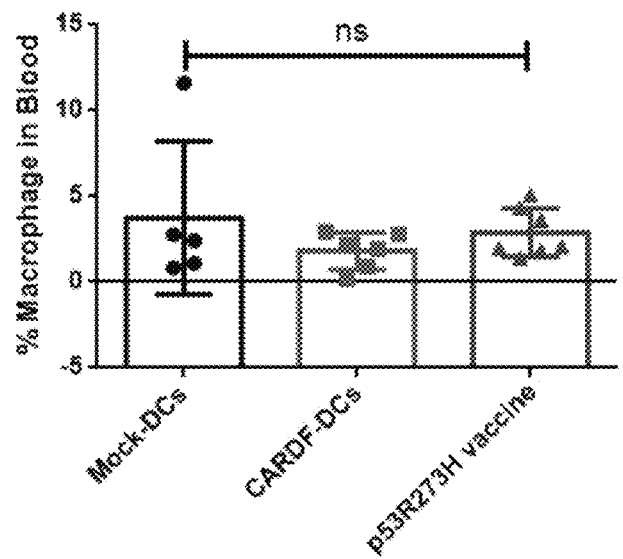
Figure 4H:
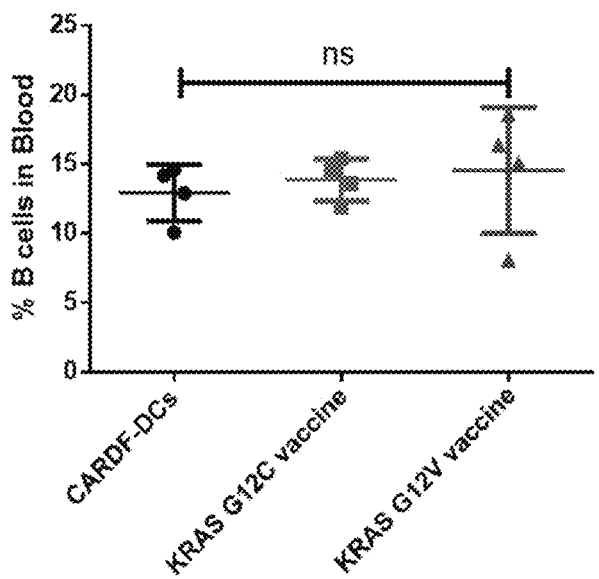

As shown in FIG. 4F-4H and Tables 12-14, the proportions of B cells and macrophages in the peripheral blood of different treatment groups have no significant difference, which indicates that there is no immune cytotoxic reaction after DC vaccine treatment.

TABLE 12

Average percentage of B cells in each group (%)

| Mock-DCs | CARDF-DCs | p53R273H vaccine |
|---|---|---|
| 6.2 | 4.23 | 5.4 |

TABLE 13

Average percentage of macrophage cells in each group (%)

| Mock-DCs | CARDF-DCs | p53R273H vaccine |
|---|---|---|
| 3.74 | 1.82 | 2.89 |

TABLE 14

Average percentage of B cells in each group (%)

| CARDF-DCs | KRAS G12C vaccine | KRAS G12V vaccine |
|---|---|---|
| 3.74 | 1.82 | 2.89 |

Figure 5A:
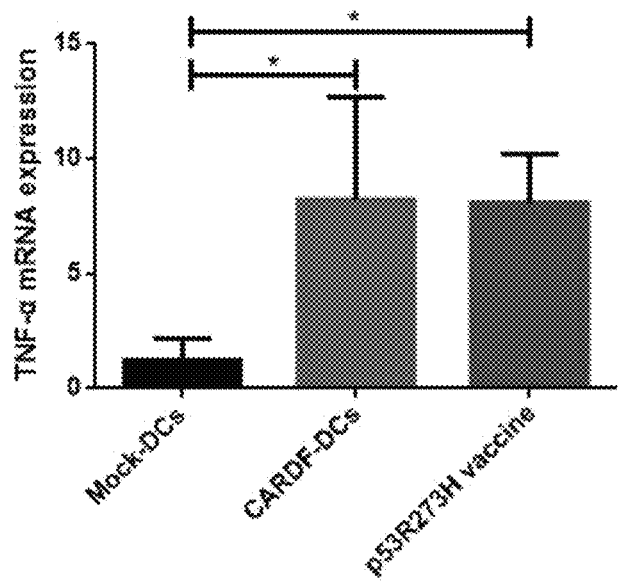

As shown in FIG. 5A and Table 15, the expression level of TNF-α gene in the SW480 tumor tissue was significantly increased in the CARDF-DCs treatment group and the p53R273H vaccine treatment group compared with the Mock-DCs treatment group, which indicates that the presence of CARDF promotes the activation of DC, thereby enhancing the expression of pro-inflammatory genes in the tumor.

TABLE 15

Average relative expression level of TNF-α mRNA in each group

| Mock-DCs | CARDF-DCs | p53R273H vaccine |
|---|---|---|
| 1.21 | 8.20 | 8.09 |

Figure 5B:
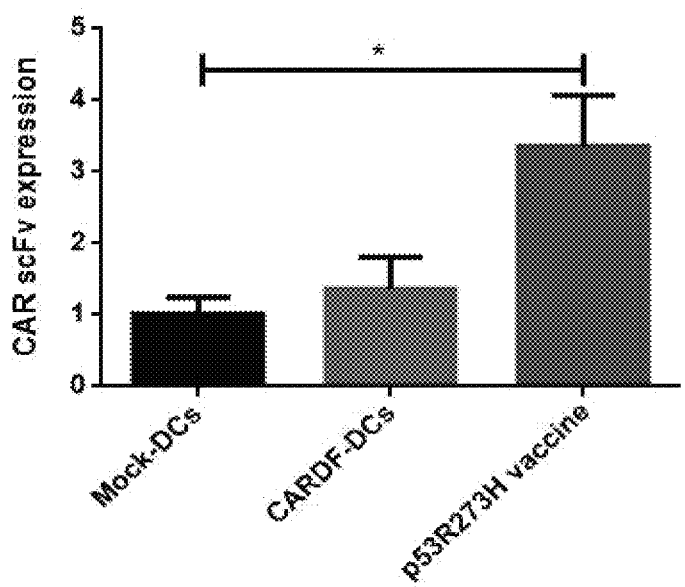

As shown in FIG. 5B and Table 16, compared with the Mock-DCs and CARDF-DCs treatment groups, the CARDF scFv gene expression in the SW480 tumor tissue in the p53R273H vaccine treatment group was significantly increased, which indicates that the infiltration of the DC vaccine increased in the tumor tissue.

TABLE 16

Average relative expression level of
CARDF scFv mRNA in each group

| Mock-DCs | CARDF-DCs | p53R273H vaccine |
|---|---|---|
| 1.01 | 1.35 | 3.36 |

As shown in FIG. 5C and Table 17, the expression of CD3 gene in SW480 tumor tissue was significantly increased in the KRAS G12V vaccine treatment group compared with the CARDF-DCs treatment group and the KRAS G12C vaccine treatment group, indicating that the infiltration of T cells in the SW480 tumor tissue increased after treated with KRAS G12V vaccine.

TABLE 17

Average relative expression level of CD3 mRNA in each group

| CARDF-DCs | KRAS G12C vaccine | KRAS G12V vaccine |
|---|---|---|
| 1.01 | 2.12 | 6.05 |

As shown in FIG. 5D and Table 18, compared with the CARDF-DCs treatment group and the KRAS G12V vaccine treatment group, the gene expression of TNF-α in the SW837 tumor tissue in the KRAS G12C vaccine treatment group was significantly increased, which indicates that that the infiltration of T cells in the SW837 tumor tissue increased after treated with KRAS G12C vaccine.

TABLE 18

Average relative expression level of TNF-α mRNA in each group

| CARDF-DCs | KRAS G12C vaccine | KRAS G12V vaccine |
|---|---|---|
| 1.02 | 2.24 | 1.47 |

The above data shows that the DC vaccine stimulated effector T cell responses in Hu-mice, effectively inhibited the growth of tumor tissues expressing the mutant gene, and had no immune cytotoxic side effects.

Example 4

This example illustrates the use of the DC tumor vaccine derived from humanized mouse bone marrow cells in treating a variety of cancers having different mutations in a Hu-mice xenograft model. CAR-DC vaccine combo can be loaded with various kinds of tumor antigens in one. In this example, the CAR-DC vaccine combo was loaded with multiple short peptides represented by P53R175H, P53R248Q, P53R249S and P53R273H, which were combined to make a functional fusion.

0.5×106 SK-BR-3 cells (breast cancer cells carrying p53 R175H mutant), 1×106 SW480 cells (colorectal cancer cells carrying p53 R273H mutant), and 1×106 OVCAR3 cells (ovarian cancer cells carrying p53 R248Q mutant) were subcutaneously injected into Hu-mice to prepare the xenograft Hu-mice tumor models. The tumor-bearing Hu-mice was randomly divided into two groups, namely: (1) CARDF-DCs treatment group; and (2) CARDC vaccine combo treatment group.

Figure 3H:
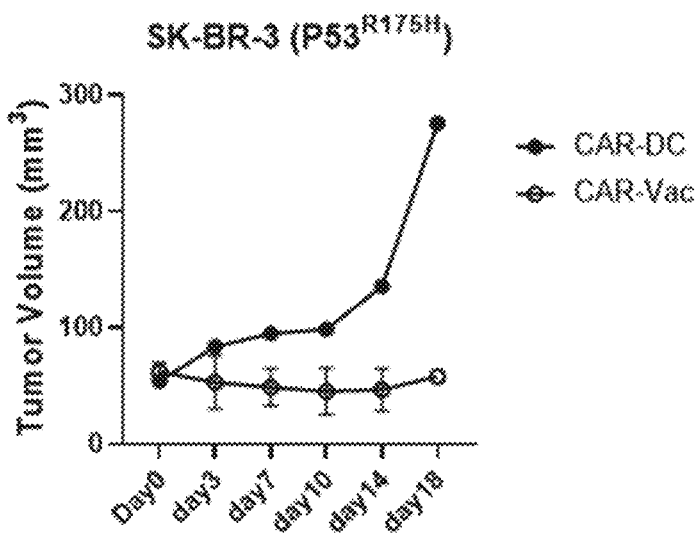
FIG. 3H shows the growth curve of SK-BR-3 tumor (expressing p53 R175H mutant) tissue during the treatment in different treatment groups using the CAR-DC vaccine combo (p53-R175H-R248Q-R249S-R273H vaccine).
Figure 3I:
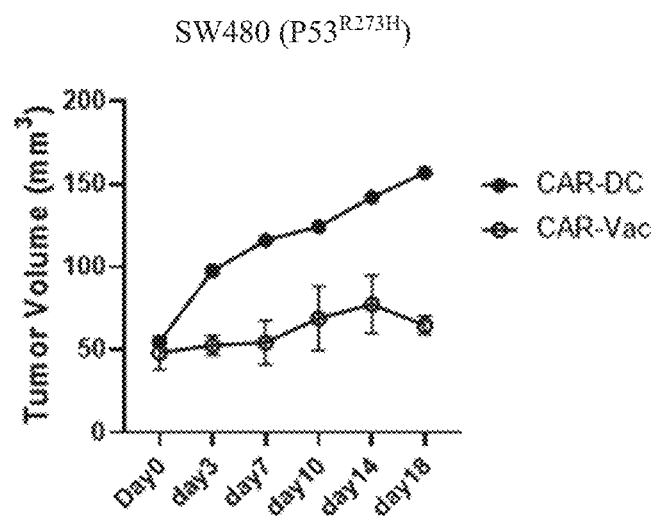
FIG. 3I shows the growth curve of SW480 tumor (expressing p53 R273H mutant) tissue during the treatment in different treatment groups using the CAR-DC vaccine combo.
Figure 3J:
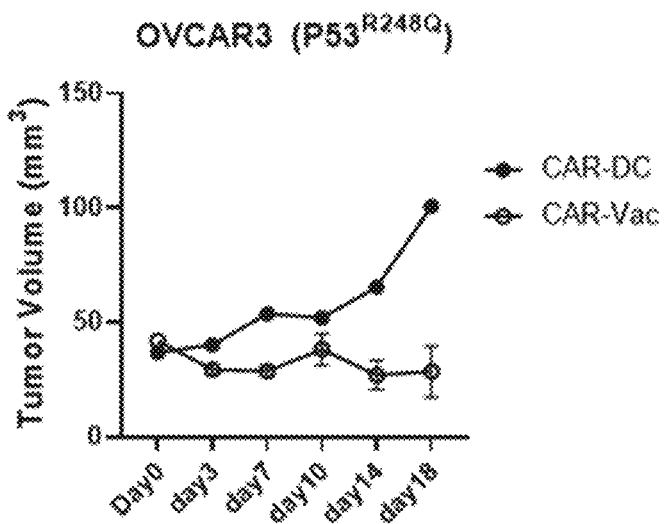
FIG. 3J shows the growth curve of OVCAR3 tumor (expressing p53 R248Q mutant) tissue during the treatment in different treatment groups using the CAR-DC vaccine combo.

The treatment process is similar to that shown in FIG. 3A. 3×106 CARDF-DC cells or CARDF-DC vaccine cells were resuspended in 500 μL DPBS, which were injected into mice through the tail vein. During the cell therapy, the size of the tumor was measured with a vernier caliper twice a week and statistics were made. When the mice were euthanized, all tumors were collected, weighed, and photographed. As shown in FIGS. 3H-3J, the CARDF-DC vaccine carrying Vaccine combo successfully inhibited tumors expressing various p53 mutants, including breast cancer carrying p53 R175H mutant, colorectal cancer carrying p53 R273H mutant and ovary cancer carrying p53 R248Q mutant. This suggests that the CARDF-DC vaccine provided herein can be used as a monotherapy to treat various tumors having different mutations.

TABLE 19

Sequences mentioned in the present disclosure

| SEQ ID NO | Name | Amino acid sequence/Nucleic acid sequence |
|---|---|---|
| 1 | ITAM of Dectin1 | RWPPSAACSGKESVVAIRTNSQSDFHLQTYGDEDLNELDPHYEM |
| 2 | ITAM of FcγR | RLKIQVRKAAITSYEKSDGVYTGLSTRNQETYETLKHEKPPQ |
| 3 | tandem amino acid sequence of the ITAMs of Dectin1 and FcγR | RWPPSAACSGKESVVAIRTNSQSDFHLQTYGDEDLNELDPHYEMRLKIQVRKAAITSYEKSDGVYTGLSTRNQETYETLKHEKPPQ |
| 4 | tandem nucleic acid sequence of the ITAMs of Dectin1 and FcγR | CGCTGGCCTCCTTCTGCAGCTTGTTCGGGAAAAGAGTCAGTTGTTGCT ATAAGGACCAATAGCCAATCTGACTTCCACTTACAAACTTATGGAGAT GAAGATTTGAATGAATTAGATCCTCATTATGAAATGCGACTGAAGATC CAAGTGCGAAAGGCAGCTATAACCAGCTATGAGAAATCAGATGGTGT TTACACGGGCCTGAGCACCAGGAACCAGGAGACTTACGAGACTCTGA AGCATGAGAAACCACCACAG |
| 5 | signal peptide of CD8 alpha | MALPVTALLLPLALLLHAARP |
| 6 | transmembrane domain of CD8 alpha | IYIWAPLAGTCGVLLLSLVITLYC |

TABLE 19-continued

Sequences mentioned in the present disclosure

| SEQ ID NO | Name | Amino acid sequence/Nucleic acid sequence |
|---|---|---|
| 7 | hinge region of CD8 alpha | TTTPAPRPPTPAPTIASQPLSLRPEACRPAAGGAVHTRGLDFACD |
| 8 | CTLA-4-Ig | MGVLLTQRTLLSLVLALLFPSMASMAMHVAQPAVVLASSRGIASFVCEYA SPGKATEVRVTVLRQADSQVTEVCAATYMMGNELTFLDDSICTGTSSGN QVNLTIQGLRAMDTGLYICKVELMYPPPYYLGIGNGTQIYVIDPEPCPDSD QEPKSSDKTHTSPPSPAPELLGGSSVFLFPPKPKDTLMISRTPEVTCVVVDV SHEDPEVKFNWYVDGVEVHNAKTKPREEQYNSTYRVVSVLTVLHQDWL NGKEYKCKVSNKALPAPIEKTISKAKGQPREPQVYTLPPSRDELTKNQVSLT CLVKGFYPSDIAVEWESNGQPENNYKTTPPVLDSDGSFFLYSKLTVDKSR WQQGNVFSCSVMHEALHNHYTQKSLSLSPGK |
| 9 | PD-L1 | MRIFAVFIFMTYWHLLNAFTVTVPKDLYVVEYGSNMTIECKFPVEKQLDL AALIVYWEMEDKNIIQFVHGEEDLKVQHSSYRQRARLLKDQLSLGNAALQ ITDVKLQDAGVYRCMISYGGADYKRITVKVNAPYNKINQRILVVDPVTSEH ELTCQAEGYPKAEVIWTSSDHQVLSGKTTTTNSKREEKLFNVTSTLRINTTT NEIFYCTFRRLDPEENHTAELVIPELPLAHPPNERTHLVILGAILLCLGVALTF IFRLRKGRMMDVKKCGIQDTNSKKQSDTHLEET |
| 10 | HCDR1 of scFv for EphA2 | GFTFSSYTMS |
| 11 | HCDR2 of scFv for EphA2 | TISSRGTYTYY PDSVKG |
| 12 | HCDR3 of scFv for EphA2 | EAIFTH |
| 13 | LCDR1 of scFv for EphA2 | KASQDINNYHS |
| 14 | LCDR2 of scFv for EphA2 | RANRLVD |
| 15 | LCDR3 of scFv for EphA2 | LKYNVFPYT |
| 16 | VH of scFv for EphA2 | QVQLLESGGGLVQPGGSLRLSCAASGFTFSSYTMSWVRQAPGQALEWM GTISSRGTYTYYPDSVKGRFTISRDNAKNSLYLQMNSLRAEDTAVYYCARE AIFTHWGRGTLVTVSS |
| 17 | VL of scFv for EphA2 | DIQLTQSPSSLSASVGDRVTITCKASQDINNYHSWYQQKPGQAPRLLIYRA NRLVDGVPDRFSGSGYGTDFTLTINNIESEDAAYYFCLKYNVFPYTFGQGT KVEIK |
| 18 | full length of scFv for EphA2 | QVQLLESGGGLVQPGGSLRLSCAASGFTFSSYTMSWVRQAPGQALEWM GTISSRGTYTYYPDSVKGRFTISRDNAKNSLYLQMNSLRAEDTAVYYCARE AIFTHWGRGTLVTVSSGGGGSGGGGSGGGGSDIQLTQSPSSLSASVGDR VTITCKASQDINNYHSWYQQKPGQAPRLLIYRANRLVDGVPDRFSGSGY GTDFTLTINNIESEDAAYYFCLKYNVFPYTFGQGTKVEIK |
| 19 | hActin-F | CAGAGCCTCGCCTTTGCCGATC |
| 20 | hActin-R | CATCCATGGTGAGCTGGCGGCG |
| 21 | hCD3-F | GGGGCAAGATGGTAATGAAG |
| 22 | hCD3-R | CCAGGATACTGAGGGCATGT |
| 23 | hTNFα-F | GCTGCACTTTGGAGTGATCG |
| 24 | hTNFα-R | TCACTCGGGGTTCGAGAAGA |
| 25 | CAR scfv-F | ATACCATGTCTTGGGTGCGA |
| 26 | CAR scfv-R | AATCGGCCCTTCACACTGTC |
| 27 | linker | GGGGSGGGGSGGGGS |
| 28 | CAR gene | Atggccttaccagtgaccgccttgctcctgccgctggccttgctgctccacgccgccaggccg caggtgcagctgttggagtctggggaggcttggtacagcctgggggtccctgagactctcc tgtgcagcctctggattcacctttagcagctataccatgtcttgggtgcgacaggcccctggac aagcgcttgagtggatgggaaccattagtagtcgtggtacttacacctactatccagacagtg tgaaggccgattcaccatctccagagacaacgccaagaactcactgtatctgcaaatgaac agcctgagagccgaggacacggctgtgtattactgtgcgagagaagctatctttactcactgg |

TABLE 19-continued

Sequences mentioned in the present disclosure

| SEQ ID NO | Name | Amino acid sequence/Nucleic acid sequence |
|---|---|---|
| | | ggccgtggcaccctggtcaccgtctcctcaggtggtggtggttctggcggcggcggctccggt<br>ggtggtggttctgacatccagttgacccagtctccatcctcccctgtctgcatctgtaggagaca<br>gagtcaccatcacttgcaaggcgagtcaggacattaataactatcacagctggtaccagcag<br>aaacctggccaggctcccaggctcctcatctatcgtgcaaacagattggtagatggggtccca<br>gacaggttcagtggcagcgggtatggaacagattttaccctcacaattaataacatagaatct<br>gaggatgctgcatattacttctgtctgaaatataatgtgtttccgtacacgttcggccaaggga<br>ccaaggtggagatcaaaaccacgacgccagcgccgcgaccaccaacaccggcgcccacca<br>tcgcgtcgcagcccctgtcctgcgcccagaggcgtgccggccagcggggggggcgcagt<br>gcacacgaggggctggacttcgcctgtgatatctacatctgggcgcccttggccgggacttg<br>tggggtccttctcctgtcactggttatcacccttactgccgctggcctccttctgcagcttgttc<br>gggaaaagagtcagttgttgctataaggaccaatagccaatctgacttccacttacaaactta<br>tggagatgaagatttgaatgaattagatcctcattatgaaatgcgactgaagatccaagtgc<br>gaaaggcagctataaccagctatgagaaatcagatggtgtttacacgggcctgagcaccag<br>gaaccaggagacttacgagactctgaagcatgagaaaccaccacagtaa |
| 29 | p53R273H<br>mutant<br>peptide | EDSSGNLLGRNSFEVHVCACPGRDRRTEEEN |
| 30 | KRAS G12C<br>mutant<br>peptide | TEYKLVVVGACGVGKSALTIQ |
| 31 | KRAS G12V<br>mutant<br>peptide | TEYKLVVVGAVGVGKSALTIQ |
| 32 | DC-LAMP<br>sorting signal | GYQRI |
| 33 | p53R273H<br>vaccine | Atgggctaccagaggatcgaagactccagtggtaatctactgggacggaacagctttgaggt<br>gcatgtttgtgcctgtcctgggagagaccggcgcacagaggaagagaat |
| 34 | KRAS G12C<br>vaccine | Atgggctaccagaggatcactgaatataaacttgtggtagttggagcttgtggcgtaggcaa<br>gagtgccttgacgatacag |
| 35 | KRAS G12V<br>vaccine | Atgggctaccagaggatcactgaatataaacttgtggtagttggagctgttggcgtaggcaa<br>gagtgccttgacgatacag |
| 36 | IRES | cccctctccctcccccccccctaacgttactggccgaagccgcttggaataaggccggtgtgc<br>gtttgtctatatgttattttccaccatattgccgtcttttggcaatgtgagggcccggaaacctg<br>gccctgtcttcttgacgagcattcctaggggtctttcccctctcgccaaaggaatgcaaggtct<br>gttgaatgtcgtgaaggaagcagttcctctggaagcttcttgaagacaaacaacgtctgtagc<br>gaccctttgcaggcagcggaaccccccacctggcgacaggtgcctctgcggccaaaagcca<br>cgtgtataagatacacctgcaaaggcggcacaaccccagtgccacgttgtgagttggatagt<br>tgtggaaagagtcaaatggctctcctcaagcgtattcaacaaggggctgaaggatgcccaga<br>aggtaccccattgtatgggatctgatctggggcctcggtgcacatgctttacatgtgtttagtc<br>gaggttaaaaaaacgtctaggccccccgaaccacggggacgtggttttcctttgaaaaacac<br>gatgataa |
| 37 | p53-R175H-<br>R248Q-R249S-<br>R273H peptide | MAIYKQSQHMTEVVRHCPHHERCSDSDGLAPPQHLIRVEGNLRVEYLDD<br>RNTFRHSVVVPYEPPEVGSDCTTIHYNYMCNSSCMGGMNQSPILTIITLE<br>DSSGNLLGRNSFEVHVCACPGRDRRTEEEN |
| 38 | p53-R175H-<br>R248Q-R249S-<br>R273H<br>polynucleotide | atggccatctacaagcagtcacagcacatgacggaggttgtgaggcactgccccccaccatga<br>gcgctgctcagatagcgatggtctggccccctcctcagcatccttatccgagtgaaggaaattt<br>gcgtgtggagtatttggatgacagaaacactttcgacatagtgtggtggtgcccatgagcc<br>gcctgaggttggctctgactgtaccaccatccactacaactacatgtgtaacagttcctgcatg<br>ggcggcatgaaccagagccccatcctcaccatcatcacactggaagactccagtggtaatct<br>actgggacggaacagctttgaggtgcatgtttgtgcctgtcctgggagagaccggcgcacag<br>aggaagagaat |

The invention claimed is:

1. A vector for preparing a dendritic cell (DC) tumor vaccine, comprising:
   (a) a polynucleotide encoding a chimeric antigen receptor (CAR) capable of activating a dendritic cell, wherein the CAR comprises (1) an extracellular antigen-binding domain comprising a single-chain variable fragment (scFv) specific for a tumor surface marker, (2) a transmembrane domain of CD8 alpha, and (3) an intracellular signaling domain comprising a cytoplasmic domain of Dectin-1 and a cytoplasmic domain of FcγR, wherein the intracellular signaling domain comprises the amino acid sequence set forth in SEQ ID NO: 3, and
   (b) a polynucleotide encoding a tumor antigen.

2. The vector of claim 1, wherein the intracellular signaling domain comprises an amino acid sequence encoded by a nucleic acid sequence set forth in SEQ ID NO: 4.

3. The vector of claim 1, wherein the tumor surface marker is selected from the group consisting of: EphA2, CD19, CD70, CD147, DLL3, EGFRvIII, Mesothelin, ganglioside GD2, FAP (fibroblast activating protein), FBP (folate binding protein), Lewis Y, Claudin 18.2, IL13Ra2, HER2, MDC1, PMSA (prostate membrane specific antigen), ROR1, B7-H3, CAIX, CD133, CD171, CEA, GPC3, MUC1, and NKG2D.

4. The vector of claim 1, wherein the CAR further comprises a signal peptide.

5. The vector of claim 4, wherein the signal peptide comprises a signal peptide of CD8 alpha.

6. The vector of claim 5, wherein the signal peptide of CD8 alpha comprises a sequence set forth in SEQ ID NO: 5.

7. The vector of claim 1, wherein the transmembrane domain of CD8 alpha comprises a sequence set forth in SEQ ID NO: 6.

8. The vector of claim 1, wherein the extracellular antigen-binding domain is linked to the transmembrane domain by a hinge region.

9. The vector of claim 8, wherein the hinge region comprises a hinge region of CD8 alpha.

10. The vector of claim 9, wherein the hinge region of CD8 alpha comprises a sequence set forth in SEQ ID NO: 7.

11. The vector of claim 1, wherein the tumor antigen is selected from the group consisting of a p53 R273H mutated peptide, a p53 R175H mutated peptide, a p53 R248Q mutated peptide, a p53 R249S mutated peptide, a p53-R175H-R248Q-R249S-R273H mutated peptide, a KRAS G12V mutated peptide, a KRAS G12C mutated peptide and a combination thereof.

12. The vector of claim 11, wherein the p53 R273H mutated peptide has a sequence set forth in SEQ ID NO: 29, the p53-R175H-R248Q-R249S-R273H mutated peptide has a sequence set forth in SEQ ID NO: 37, the KRAS G12V mutated peptide has a sequence set forth in SEQ ID NO: 31, and the KRAS G12C mutated peptide has a sequence set forth in SEQ ID NO: 30.

13. The vector of claim 1, wherein the tumor antigen is linked to a DC-LAMP sorting signal having a sequence set forth in SEQ ID NO: 32.

14. The vector of claim 1, which is a DNA or RNA.

15. The vector of claim 14, wherein the polynucleotide encoding the CAR and/or the polynucleotide encoding the tumor antigen is operatively linked to at least one regulatory polynucleotide element for expression of the CAR and/or the tumor antigen.

16. The vector of claim 15, wherein the polynucleotide encoding the CAR is operably linked to the polynucleotide encoding the tumor antigen via an IRES having a sequence set forth in SEQ ID NO: 36.

17. The vector of claim 14, wherein the vector is a plasmid vector, a viral vector, a transposon, a site directed insertion vector, or a suicide expression vector.

18. The vector of claim 17, wherein the viral vector is a lentiviral vector, a retroviral vector, or an AAV vector.

19. An engineered cell comprising the vector of claim 1.

20. The engineered cell of claim 19, wherein the engineered cell is a dendritic cell or a precursor or progenitor cell thereof.

21. A pharmaceutical composition comprising (i) a population of the engineered cells of claim 19, and (ii) a pharmaceutically acceptable medium.

* * * * *